US011547373B2

(12) United States Patent
Konno et al.

(10) Patent No.: US 11,547,373 B2
(45) Date of Patent: Jan. 10, 2023

(54) TOMOSYNTHESIS IMAGING APPARATUS

(71) Applicant: FUJIFILM Corporation, Tokyo (JP)

(72) Inventors: Shinichiro Konno, Kanagawa (JP); Yoshie Fujimoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/987,595

(22) Filed: Aug. 7, 2020

(65) Prior Publication Data
US 2021/0068769 A1    Mar. 11, 2021

(30) Foreign Application Priority Data

Sep. 6, 2019    (JP) .............................. JP2019-162949

(51) Int. Cl.
*A61B 6/02* (2006.01)
*A61B 6/00* (2006.01)
*G01N 23/046* (2018.01)

(52) U.S. Cl.
CPC .............. *A61B 6/025* (2013.01); *A61B 6/502* (2013.01); *G01N 23/046* (2013.01)

(58) Field of Classification Search
CPC ........ A61B 6/025; A61B 6/502; G01N 23/046
See application file for complete search history.

(56) References Cited

U.S. PATENT DOCUMENTS

| 3,023,314 A | * | 2/1962 | Hura | ........................ G21K 1/04 |
| | | | | 976/DIG. 430 |
| 4,232,226 A | | 11/1980 | Huettner et al. | |
| 5,459,320 A | * | 10/1995 | Danet | .................... G01T 1/1644 |
| | | | | 250/363.04 |
| 6,175,609 B1 | * | 1/2001 | Edic | ..................... G01N 23/046 |
| | | | | 378/155 |

(Continued)

FOREIGN PATENT DOCUMENTS

| EP | 3 078 328 A2 | 10/2016 |
| JP | S55-029396 A | 3/1980 |

(Continued)

OTHER PUBLICATIONS

The extended European search report issued by the European Patent Office dated Feb. 1, 2021, which corresponds to European Patent Application No. 20194174.7-1122 and is related to U.S. Appl. No. 16/987,595.

(Continued)

*Primary Examiner* — Blake C Riddick
(74) *Attorney, Agent, or Firm* — Studebaker & Brackett PC

(57) ABSTRACT

Fifteen radiation tubes are arranged in a radiation source of the mammography apparatus. An irradiation field limiter includes a plate-like member having a plurality of through holes that function as irradiation openings. Adjacent through holes are arranged at an interval of one radiation tube. In the plate-like member, the position of the through holes which (Continued)

are irradiation openings are moved to a first set position in a case in which radiation is emitted from first radiation tubes which are some of three or more radiation tubes and a second set position in a case in which the radiation is emitted from second radiation tubes different from the first radiation tubes among the three or more radiation tubes. Therefore, one through hole is shared by two radiation tubes.

16 Claims, 52 Drawing Sheets

(56) References Cited

U.S. PATENT DOCUMENTS

| | | | |
|---|---|---|---|
| 6,424,693 B1* | 7/2002 | Weisenberger | A61B 6/0414 250/363.04 |
| 2002/0015474 A1* | 2/2002 | Tybinkowski | G21K 1/025 378/147 |
| 2003/0058984 A1* | 3/2003 | Susami | A61B 6/037 378/19 |
| 2005/0169431 A1 | 8/2005 | Groh et al. | |
| 2006/0067481 A1 | 3/2006 | Morton | |
| 2006/0182223 A1* | 8/2006 | Heuscher | H01J 35/103 378/137 |
| 2007/0098141 A1* | 5/2007 | Hjarn | A61B 6/4441 378/37 |
| 2008/0198966 A1* | 8/2008 | Hjarn | A61B 6/502 378/37 |
| 2009/0304150 A1* | 12/2009 | Metzler | G01T 1/1648 378/150 |
| 2010/0091939 A1 | 4/2010 | Fadler | |
| 2010/0091940 A1 | 4/2010 | Ludwig et al. | |
| 2012/0257715 A1* | 10/2012 | Kobayashi | A61B 6/5282 250/366 |
| 2013/0163715 A1* | 6/2013 | Kurochi | A61B 6/035 378/19 |
| 2014/0016742 A1* | 1/2014 | Sall | A61B 6/06 378/37 |
| 2014/0314198 A1* | 10/2014 | Ren | A61B 6/502 378/4 |
| 2015/0055759 A1* | 2/2015 | Schmidt | G21K 1/04 378/147 |
| 2015/0162107 A1* | 6/2015 | Kato | G21K 1/025 156/60 |
| 2015/0238153 A1* | 8/2015 | Kim | A61B 6/035 378/19 |
| 2015/0320371 A1 | 11/2015 | Heath et al. | |
| 2016/0249872 A1 | 9/2016 | Grass et al. | |
| 2016/0270745 A1 | 9/2016 | Heath et al. | |
| 2016/0379794 A1 | 12/2016 | Shiozawa et al. | |
| 2017/0172525 A1* | 6/2017 | Proksa | A61B 6/4429 |
| 2018/0168523 A1* | 6/2018 | Vancamberg | A61B 6/461 |
| 2018/0192978 A1* | 7/2018 | Naylor | G02B 30/54 |
| 2018/0263578 A1* | 9/2018 | Abramovich | A61B 6/06 |
| 2019/0219714 A1* | 7/2019 | Vecchio | G01T 7/005 |
| 2020/0312478 A1* | 10/2020 | Sutter | A61B 5/70 |

FOREIGN PATENT DOCUMENTS

| | | |
|---|---|---|
| JP | H08-508431 A | 9/1996 |
| JP | 2000-005330 A | 1/2000 |
| JP | 2004-089699 A | 3/2004 |
| JP | 2009-131656 A | 6/2009 |
| JP | 2014-087697 A | 5/2014 |
| JP | 2015-104459 A | 6/2015 |
| WO | 94/23458 A2 | 10/1994 |
| WO | 2014/116665 A2 | 7/2014 |
| WO | 2015/058980 A1 | 4/2015 |

OTHER PUBLICATIONS

The extended European search report issued by the European Patent Office dated Jan. 4, 2022, which corresponds to European Patent Application No. 21195988.7-1126 and is related to U.S. Appl. No. 16/987,595.

The extended European search report issued by the European Patent Office dated Jan. 4, 2022, which corresponds to European Patent Application No. 21195994.5-1126 and is related to U.S. Appl. No. 16/987,595.

The extended European search report issued by the European Patent Office dated Jan. 4, 2022, which corresponds to European Patent Application No. 21196000.0-1126 and is related to U.S. Appl. No. 16/987,595.

An Office Action; "Notice of Reasons for Refusal," mailed by the Japanese Patent Office dated Jun. 28, 2022, which corresponds to Japanese Patent Application No. 2019-162949 and is related to U.S. Appl. No. 16/987,595; with English language translation.

* cited by examiner

FIG. 17

| SETTING TABLE | | |
|---|---|---|
| COMPRESSION PLATE USED | IMAGING MODE | RADIATION TUBE USED |
| COMPRESSION PLATE A | IMAGE QUALITY PRIORITY MODE | RT01 TO RT15 (SP1 TO SP15) |
| COMPRESSION PLATE A | EXPOSURE REDUCTION MODE | RT01, RT03, RT04, RT06, RT08, RT10, RT12, RT13, RT15 (SP1, SP3, SP4, SP6, SP8, SP10, SP12, SP13, SP15) |
| COMPRESSION PLATE B | IMAGE QUALITY PRIORITY MODE | RT02 TO RT14 (SP2 TO SP14) |
| COMPRESSION PLATE B | EXPOSURE REDUCTION MODE | RT02, RT04, RT06, RT08, RT10, RT12, RT14 (SP2, SP4, SP6, SP8, SP10, SP12, SP14) |
| ... | | |

FIG. 18

| OPERATING CONDITIONS | | | |
|---|---|---|---|
| IRRADIATION NUMBER | RADIATION TUBE | SET POSITION OF PLATE-LIKE MEMBER | |
| 1 | RT03 (SP3) | FIRST SET POSITION | |
| 2 | RT05 (SP5) | FIRST SET POSITION | |
| 3 | RT07 (SP7) | FIRST SET POSITION | |
| 4 | RT09 (SP9) | FIRST SET POSITION | |
| 5 | RT11 (SP11) | FIRST SET POSITION | |
| 6 | RT13 (SP13) | FIRST SET POSITION | |
| 7 | RT02 (SP2) | SECOND SET POSITION | MOVEMENT |
| 8 | RT04 (SP4) | SECOND SET POSITION | |
| 9 | RT06 (SP6) | SECOND SET POSITION | |
| 10 | RT08 (SP8) | SECOND SET POSITION | |
| 11 | RT10 (SP10) | SECOND SET POSITION | |
| 12 | RT12 (SP12) | SECOND SET POSITION | |
| 13 | RT14 (SP14) | SECOND SET POSITION | |

88

FIG. 33
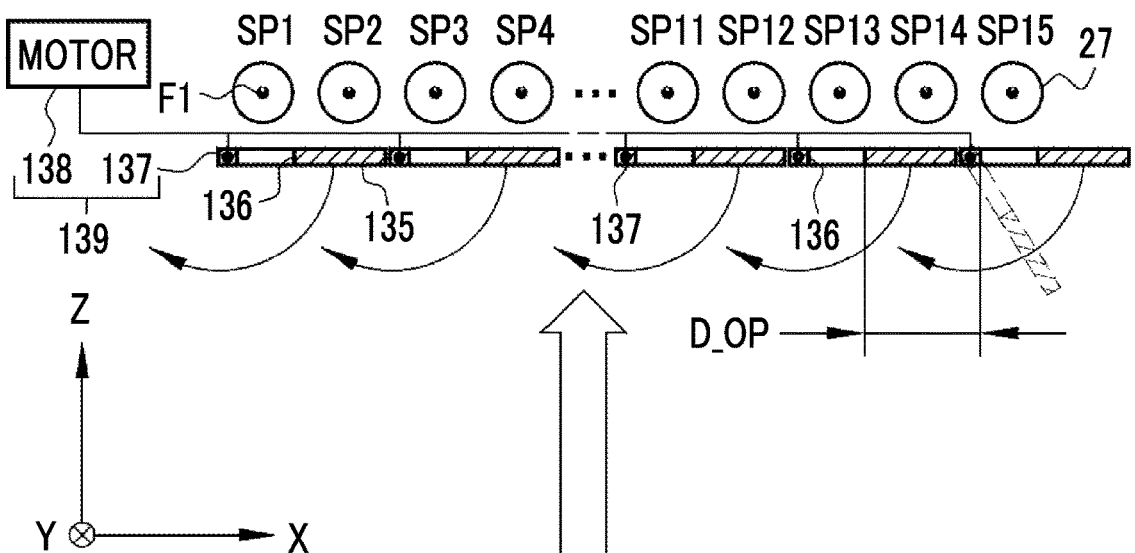
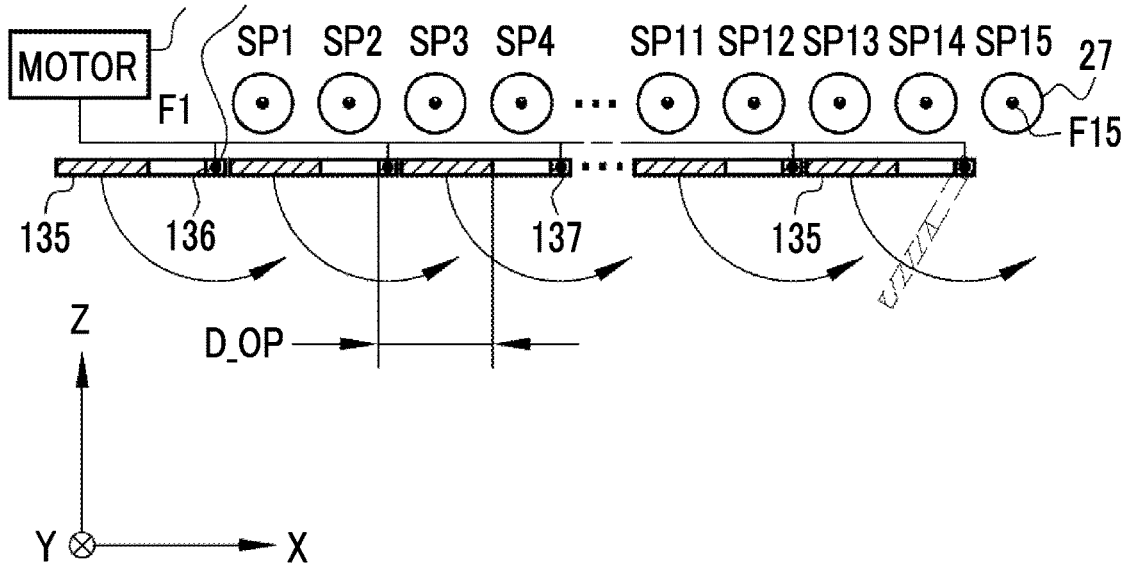

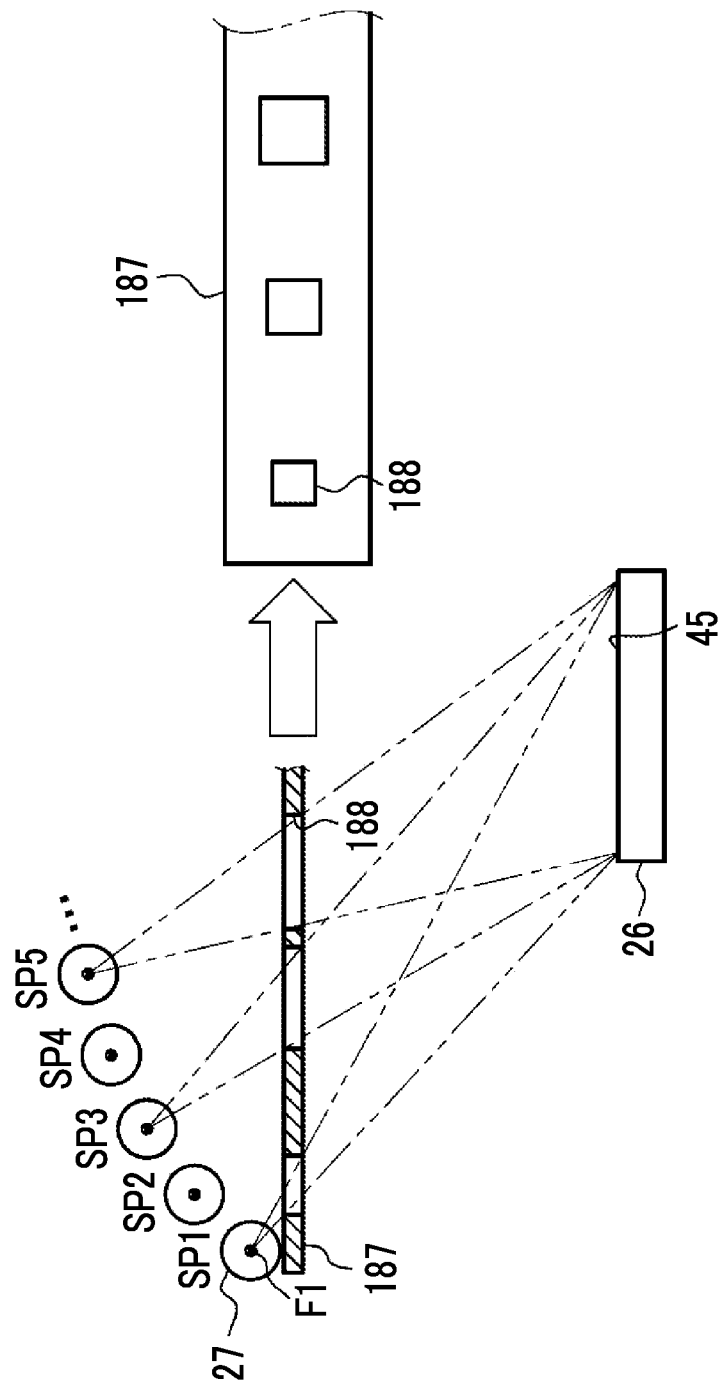

FIG. 52

| | PATTERN 1 | PATTERN 2 | PATTERN 3 | PATTERN 4 | PATTERN 5 |
|---|---|---|---|---|---|
| ARRANGEMENT OF RADIATION TUBES | LINEAR SHAPE | LINEAR SHAPE | LINEAR SHAPE | ARC SHAPE | ARC SHAPE |
| POSITIONAL RELATIONSHIP BETWEEN PLATE-LIKE MEMBER AND IMAGING SURFACE | PARALLELISM | ANGLE α | ANGLE α | EQUAL DISTANCE | PARALLELISM |
| POSITIONAL RELATIONSHIP BETWEEN PLATE-LIKE MEMBER AND RADIATION TUBE | PARALLELISM | PARALLELISM | ANGLE β | PARALLELISM | ANGLE γ |
| SIZE OF THROUGH HOLE | SAME | DIFFERENT | SAME | DIFFERENT | DIFFERENT |
| SHAPE OF THROUGH HOLE | RECTANGULAR SHAPE | TRAPEZOIDAL SHAPE | TRAPEZOIDAL SHAPE | TRAPEZOIDAL SHAPE | RECTANGULAR SHAPE |

189

TOMOSYNTHESIS IMAGING APPARATUS

CROSS-REFERENCE TO RELATED APPLICATIONS

The present application claims priority under 35 U.S.C. § 119 to Japanese Patent Application No. 2019-162949 filed on Sep. 6, 2019. The above application is hereby expressly incorporated by reference, in its entirety, into the present application.

BACKGROUND

1. Technical Field

The technology of the present disclosure relates to a tomosynthesis imaging apparatus.

2. Description of the Related Art

Tomosynthesis imaging has been known which irradiates an object with radiation at a plurality of different irradiation angles in order to generate a tomographic image in any tomographic plane of the object. JP2014-087697A discloses a tomosynthesis imaging apparatus that performs tomosynthesis imaging using a radiation source in which a plurality of focuses where radiation is emitted are arranged. The tomosynthesis imaging apparatus disclosed in JP2014-087697A has an irradiation field limiter in which irradiation openings for radiation which define the irradiation field of radiation are formed so as to correspond to each of a plurality of focuses.

SUMMARY

The inventors have studied a technique in which three or more radiation tubes, each of which has one or more focuses, are used and adjacent radiation tubes are brought close to each other to improve the signal-noise (SN) ratio of a tomographic image. In this configuration, in a case in which an irradiation field limiter having irradiation openings formed so as to correspond to each of a plurality of radiation tubes is applied and radiation is emitted from a certain radiation tube, the radiation leaks from the irradiation openings corresponding to adjacent radiation tubes, which may cause unnecessary exposure.

An object of the technology of the present disclosure is to provide a tomosynthesis imaging apparatus that can prevent unnecessary exposure.

In order to achieve the above object, according to the present disclosure, there is provided a tomosynthesis imaging apparatus comprising: a radiation source in which three or more radiation tubes emitting radiation are arranged to perform tomosynthesis imaging which irradiates an object with the radiation at a plurality of different irradiation angles; and an irradiation field limiter in which a plurality of irradiation openings for the radiation that define an irradiation field of the radiation are arranged along an arrangement direction of the radiation tubes at an interval of at least one radiation tube and a position of the irradiation openings is moved to at least two set positions including a first set position in a case in which the radiation is emitted from first radiation tubes which are some of the three or more radiation tubes and a second set position in a case in which the radiation is emitted from second radiation tubes different from the first radiation tubes among the three or more radiation tubes.

Preferably, the irradiation field limiter includes a plate-like member in which a through hole functioning as the irradiation opening is formed and the plate-like member is moved along the arrangement direction of the radiation tubes to move the position of the irradiation openings to the at least two set positions.

Preferably, the plate-like member is moved in a direction in which an interval between the radiation tube and the through hole changes.

Preferably, the plate-like member has a convex portion that protrudes toward the radiation tube between the through holes adjacent to each other.

Preferably, the irradiation field limiter has a configuration in which plate-like members, in which a through hole at least one side of which functions as an opening edge of the irradiation opening is formed, are stacked in a direction normal to an imaging surface of a radiation detector that detects the radiation and outputs a radiographic image, and each of a plurality of the plate-like members is moved along the arrangement direction of the radiation tubes to move the position of the irradiation openings to the at least two set positions.

Preferably, the irradiation field limiter has one actuator that moves two of the plate-like members, which are adjacent to each other in a stacking direction, along the arrangement direction of the radiation tubes at the same time.

Preferably, the irradiation field limiter includes a sheet-like member in which a through hole functioning as the irradiation opening is formed and the sheet-like member is sent along the arrangement direction of the radiation tubes and is rolled to move the irradiation opening.

Preferably, a plurality of types of the through holes having different sizes are formed in the sheet-like member.

Preferably, the irradiation field limiter includes a plate-like member in which a through hole functioning as the irradiation opening is formed and the plate-like member is rotated about a rotating shaft which is provided between the radiation tube and an imaging surface of a radiation detector that detects the radiation and outputs a radiographic image to move the irradiation opening to the at least two set positions.

Preferably, the irradiation field limiter has an adjustment member that adjusts a width of the plurality of irradiation openings and the adjustment member is moved in a direction intersecting the arrangement direction of the radiation tubes to adjust the width of the plurality of irradiation openings at once.

Preferably, a plurality of the radiation tubes are arranged at equal intervals in a linear shape or an arc shape.

According to the technique of the present disclosure, it is possible to provide a tomosynthesis imaging apparatus that can prevent unnecessary exposure.

BRIEF DESCRIPTION OF THE DRAWINGS

Exemplary embodiments according to the technique of the present disclosure will be described in detail based on the following figures, wherein:

FIG. 17 is a diagram illustrating a setting table;

FIG. 18 is a diagram illustrating operating conditions;

FIG. 29A illustrates a case in which the width of the irradiation opening in the X direction is increased and FIG. 29B illustrates a case in which the width of the irradiation opening in the X direction is decreased;

FIG. 33 is a diagram illustrating a sixth embodiment in which plate-like members are rotated to move irradiation openings. (A) of FIG. 33 illustrates a first set position and (B) of FIG. 33 illustrates a second set position;

FIG. 51 is a diagram illustrating another example of the size and shape of the through holes of the plate-like member in the example illustrated in FIG. 47;

FIG. 52 is a table summarizing the sizes and shapes of the through holes in the aspects illustrated in FIGS. 42 to 51.

DETAILED DESCRIPTION

First Embodiment

Figure 1:
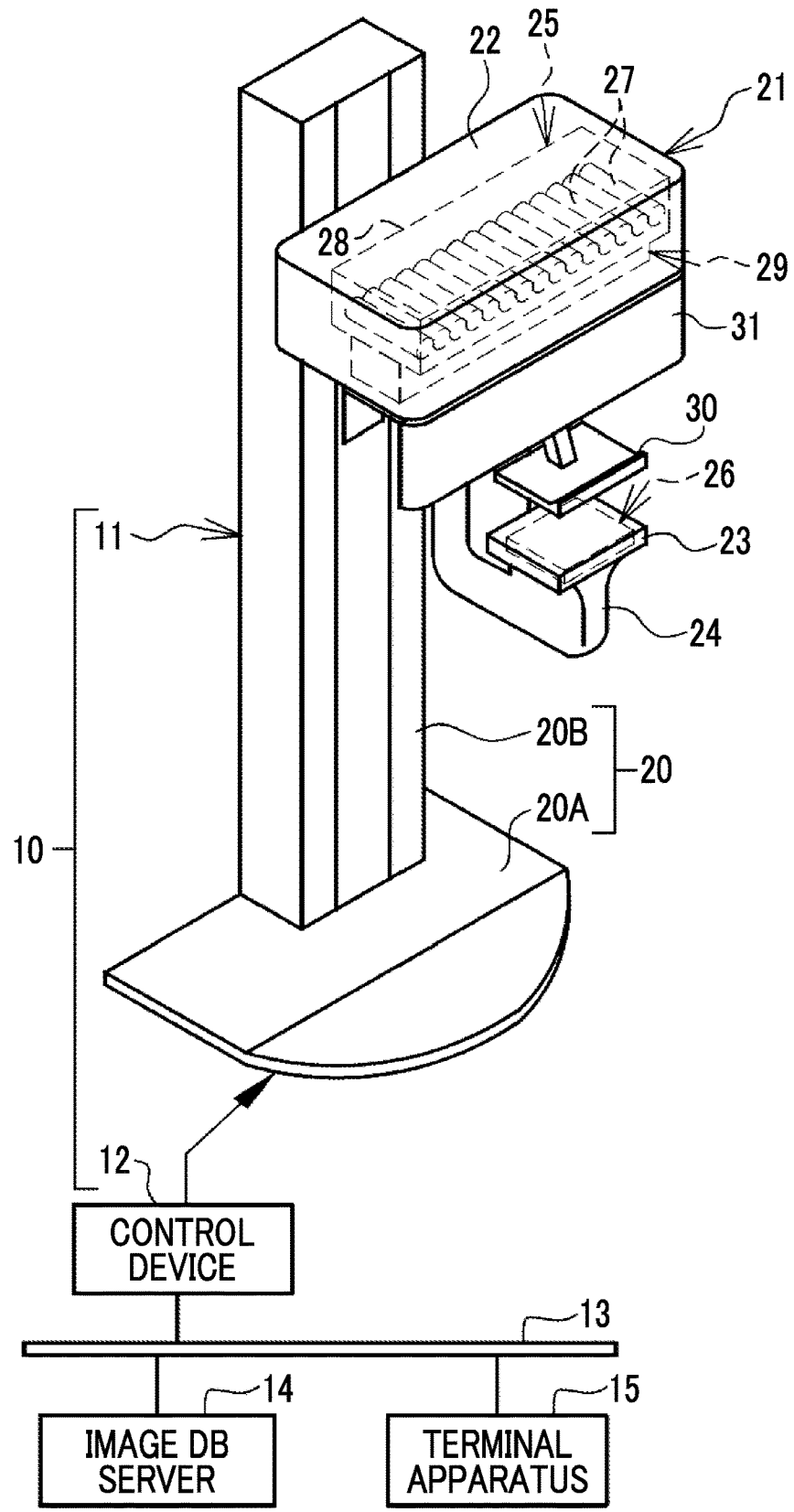
FIG. 1 is a diagram illustrating, for example, a mammography apparatus.
Figure 2:
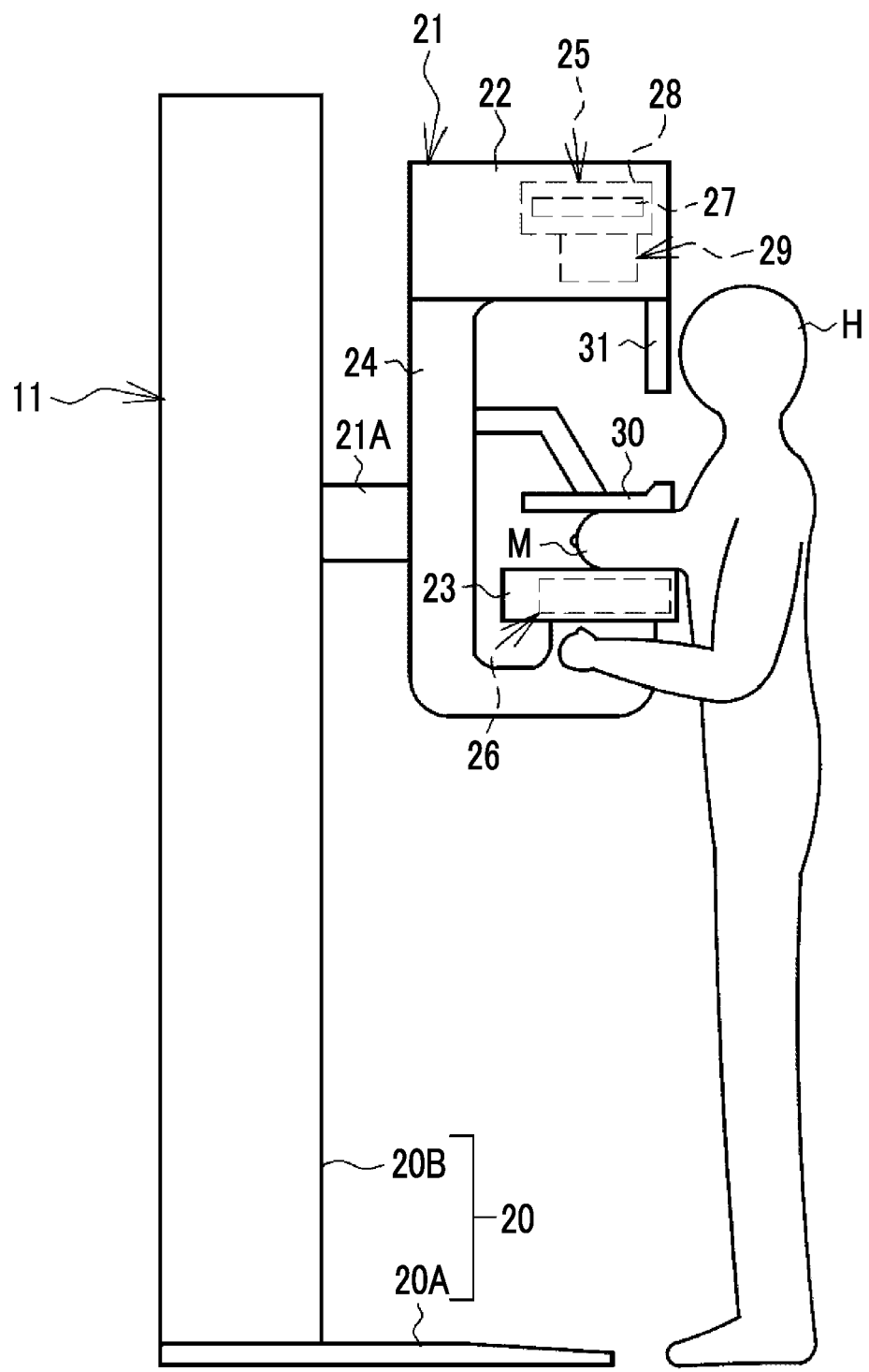
FIG. 2 is a diagram illustrating an apparatus main body of the mammography apparatus.

In FIGS. 1 and 2, a mammography apparatus 10 is an example of a "tomosynthesis imaging apparatus" according to the technique of the present disclosure and a breast M of a subject H is an object. The mammography apparatus 10 irradiates the breast M with radiation 37 (see, for example, FIG. 3), such as X-rays or y-rays, to capture a radiographic image of the breast M.

The mammography apparatus 10 includes an apparatus main body 11 and a control device 12. The apparatus main body 11 is installed, for example, in a radiography room of a medical facility. The control device 12 is installed, for example, in a control room next to the radiography room. The control device 12 is, for example, a desktop personal computer. The control device 12 is connected to an image database (hereinafter, referred to as a DB) server 14 through a network 13, such as a local area network (LAN), such that it can communicate with the image DB server 14. The image DB server 14 is, for example, a picture archiving and communication system (PACS) server, receives a radiographic image from the mammography apparatus 10, stores the radiographic image, and manages the radiographic image.

A terminal apparatus 15 is also connected to the network 13. The terminal apparatus 15 is, for example, a personal computer that is used by a doctor to make a diagnosis based on the radiographic image. The terminal apparatus 15 receives the radiographic image from the image DB server 14 and displays the radiographic image on a display.

The apparatus main body 11 includes a stand 20 and an arm 21. The stand 20 includes a pedestal 20A that is provided on the floor of the radiography room and a support 20B that extends from the pedestal 20A in a height direction. The arm 21 has a substantially C-shape in a side view and is connected to the support 20B through a connection portion 21A. The arm 21 can be moved with respect to the support 20B in the height direction by the connection portion 21A and the height of the arm 21 can be adjusted according to the height of the subject H by the connection portion 21A. In addition, the arm 21 is rotatable on a rotating shaft perpendicular to the support 20B through the connection portion 21A.

The arm 21 includes a radiation source accommodation portion 22, a detector accommodation portion 23, and a main body portion 24. The radiation source accommodation portion 22 accommodates a radiation source 25. The detector accommodation portion 23 accommodates a radiation detector 26. In addition, the detector accommodation portion 23 functions as an imaging table on which the breast M is placed. The main body portion 24 integrally connects the radiation source accommodation portion 22 and the detector accommodation portion 23. The radiation source accommodation portion 22 is provided on the upper side in the height direction and the detector accommodation portion 23 is provided on the lower side in the height direction at a posture where the detector accommodation portion 23 faces the radiation source accommodation portion 22.

The radiation source 25 includes a plurality of radiation tubes 27, for example, 15 radiation tubes 27 and a housing 28 that accommodates the radiation tubes 27. The housing 28 is filled with insulating oil. The radiation tubes 27 are used for tomosynthesis imaging which captures a plurality of projection images P (see FIG. 7) of the breast M at different irradiation angles as radiographic images. The radiation detector 26 detects the radiation 37 transmitted through the breast M and outputs a radiographic image. In addition, the number of radiation tubes 27 is not limited to 15 in the above example. The number of radiation tubes 27 may be three or more.

The radiation source accommodation portion 22 accommodates an irradiation field limiter 29 in addition to the radiation source 25. The irradiation field limiter 29 is attached to a lower part of the radiation source 25. The irradiation field limiter 29 is also called a collimator and defines the irradiation field of the radiation 37 in an imaging surface 45 (see FIG. 4) of the radiation detector 26.

A compression plate 30 is attached between the radiation source accommodation portion 22 and the detector accommodation portion 23 in the main body portion 24. The compression plate 30 is made of a material that transmits the radiation 37. The compression plate 30 is disposed so as to face the detector accommodation portion 23. The compression plate 30 can be moved in a direction toward the detector accommodation portion 23 and a direction away from the detector accommodation portion 23. The compression plate 30 is moved toward the detector accommodation portion 23 and compresses the breast M interposed between the detector accommodation portion 23 and the compression plate 30. There are a plurality of types of compression plates 30 which are interchanged according to, for example, the size of the breast M.

A face guard 31 is attached to a lower part of the front surface of the radiation source accommodation portion 22. The face guard 31 protects the face of the subject H from the radiation 37.

A tube voltage generator (not illustrated) that generates a tube voltage applied to the radiation tubes 27 is provided in the support 20B. In addition, a voltage cable (not illustrated) extending from the tube voltage generator is provided in the support 20B. The voltage cable further extends from the connection portion 21A into the radiation source accommodation portion 22 through the arm 21 and is connected to the radiation source 25.

Figure 3:
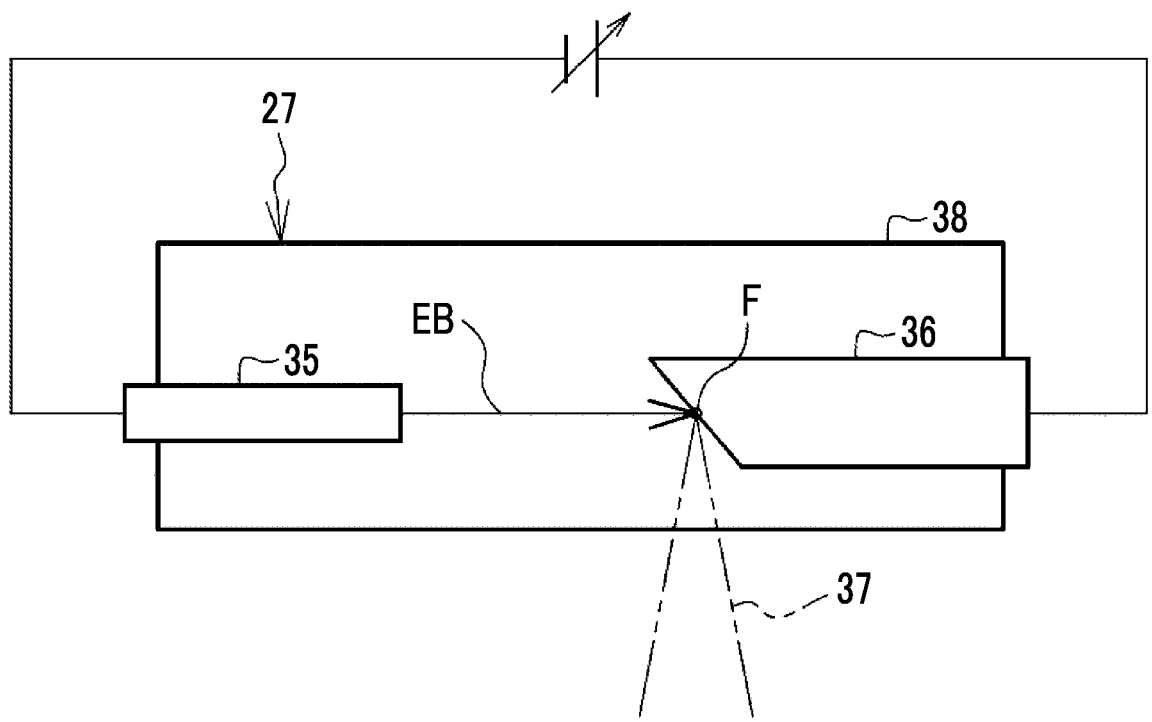
FIG. 3 is a diagram illustrating a radiation tube.

In FIG. 3, the radiation tube 27 includes a cathode 35 and an anode 36. The cathode 35 emits electrons. The electrons collide with the anode 36 and the anode 36 emits the radiation 37. The cathode 35 and the anode 36 are accommodated in a vacuum glass tube 38 with a substantially cylindrical shape. The cathode 35 is a cold cathode. Specifically, the cathode 35 is an electron emission type including an electron emission source that emits an electron beam EB to the anode 36, using a field emission phenomenon. The anode 36 is a fixed anode which is not rotated and whose position is fixed, unlike a rotating anode that is rotated by a rotation mechanism.

The tube voltage generator applies a tube voltage between the cathode 35 and the anode 36. The electron beam EB is emitted from the cathode 35 to the anode 36 by the application of the tube voltage. Then, the radiation 37 is emitted from a point (hereinafter, referred to as a focus) F of the anode 36 where the electron beam EB collides.

Figure 4:
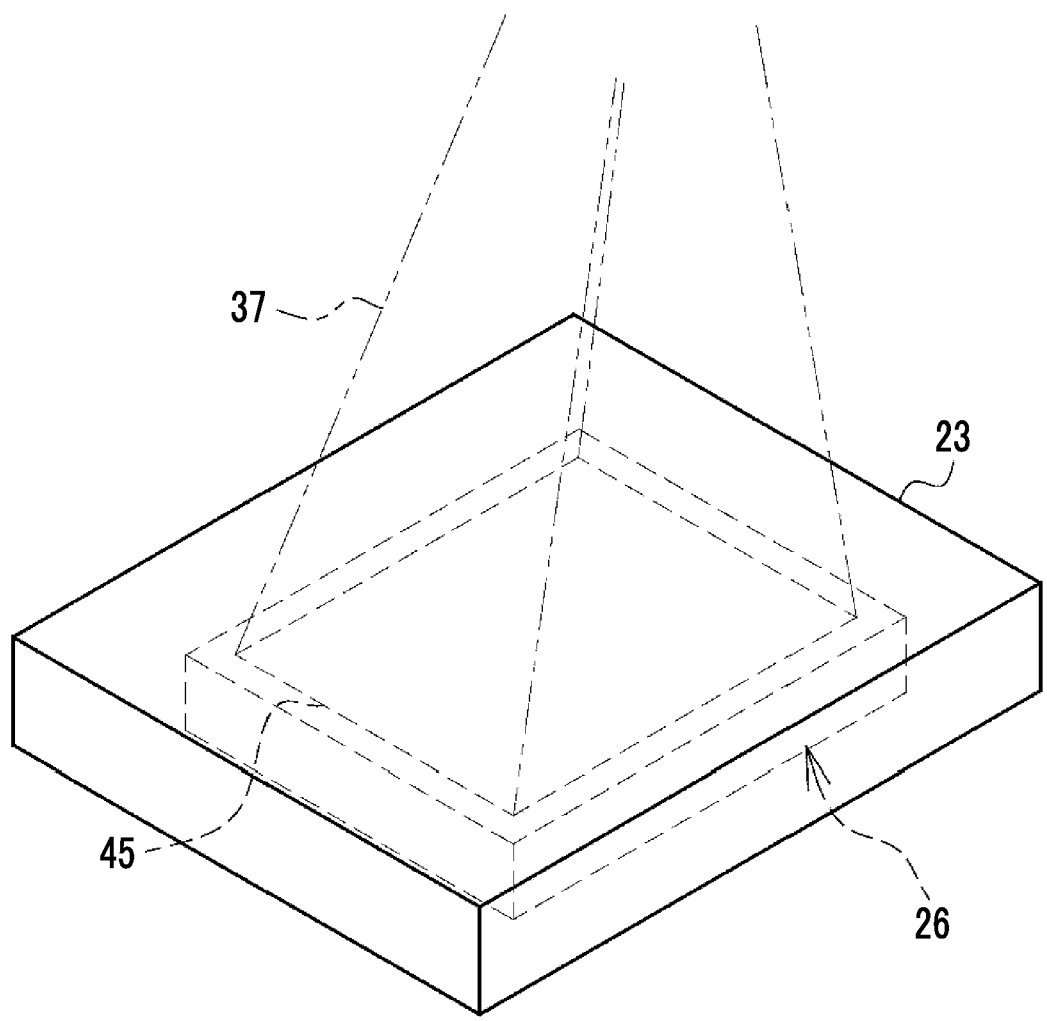
FIG. 4 is a diagram illustrating a detector accommodation portion.

In FIG. 4 illustrating the detector accommodation portion 23, the radiation detector 26 has the imaging surface 45. The imaging surface 45 detects the radiation 37 transmitted through the breast M to capture the projection image P of the breast M. Specifically, the imaging surface 45 is a two-dimensional plane in which pixels converting the radiation 37 into an electric signal are two-dimensionally arranged. The radiation detector 26 is called a flat panel detector (FPD). The radiation detector 26 may be an indirect conversion type that includes, for example, a scintillator converting the radiation 37 into visible light and converts visible light emitted from the scintillator into an electric signal or a direct conversion type that directly converts the radiation 37 into an electric signal.

Figure 5:
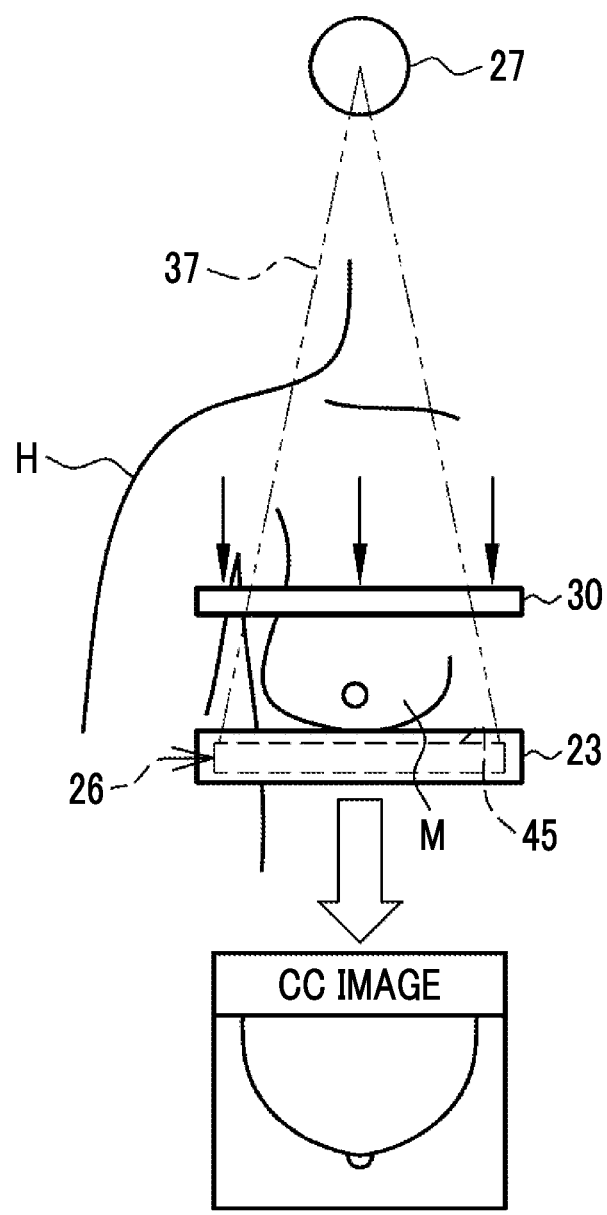
FIG. 5 is a diagram illustrating an aspect of CC imaging.
Figure 6:
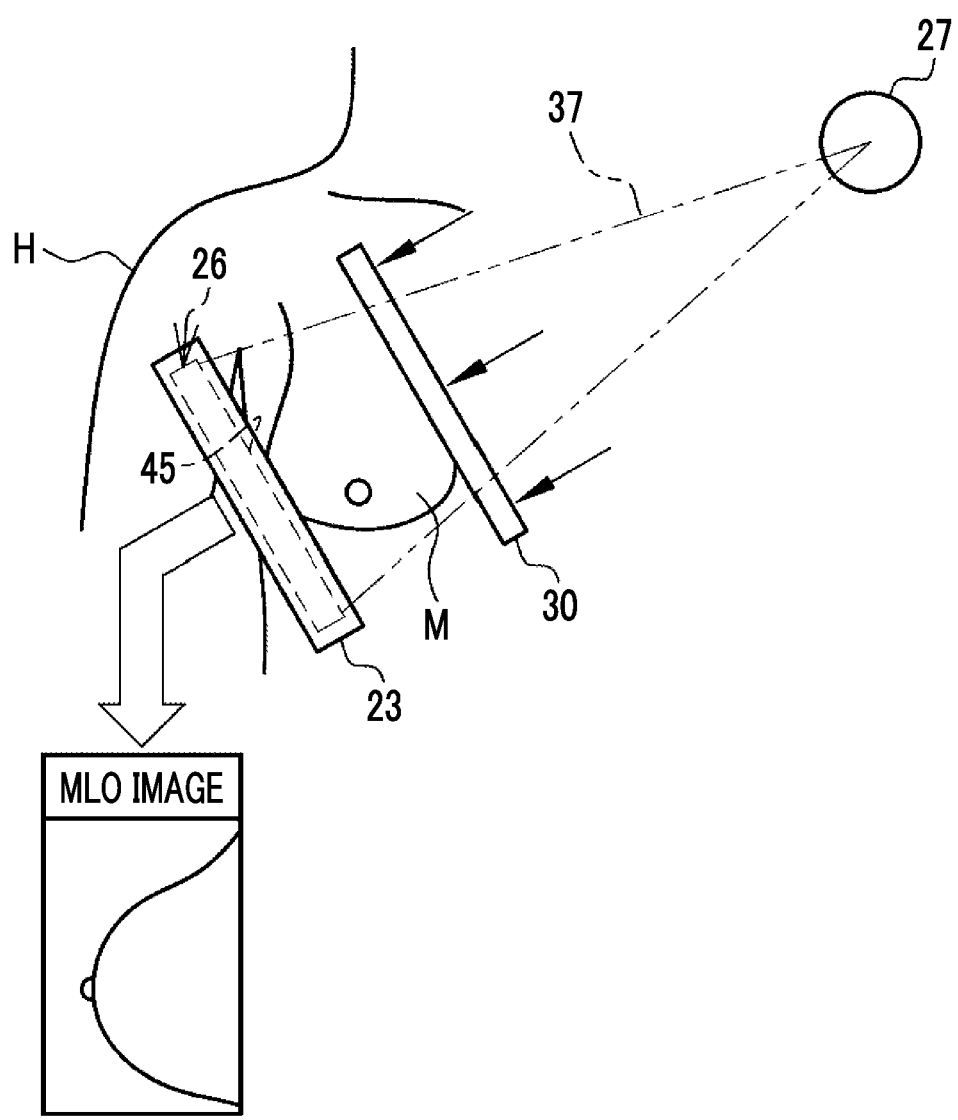
FIG. 6 is a diagram illustrating an aspect of MLO imaging.

FIGS. 5 and 6 illustrate a method for capturing an image of the breast M in the mammography apparatus 10. FIG. 5 illustrates craniocaudal view (CC) imaging and FIG. 6 illustrates mediolateral oblique view (MLO) imaging. The CC imaging is an imaging method which captures an image while compressing the breast M interposed between the detector accommodation portion 23 and the compression plate 30 in the vertical direction. In this case, the radiation detector 26 outputs a CC image as the projection image P. In contrast, the MLO imaging is an imaging method which captures an image while compressing the breast M interposed between the detector accommodation portion 23 and the compression plate 30 at an inclination angle of about 60°. In this case, the radiation detector 26 outputs an MLO image as the projection image P. In addition, FIGS. 5 and 6 illustrate only one radiation tube 27 for simplicity of illustration. Further, FIGS. 5 and 6 illustrate the right breast M. However, an image of the left breast M may be captured.

Figure 7:
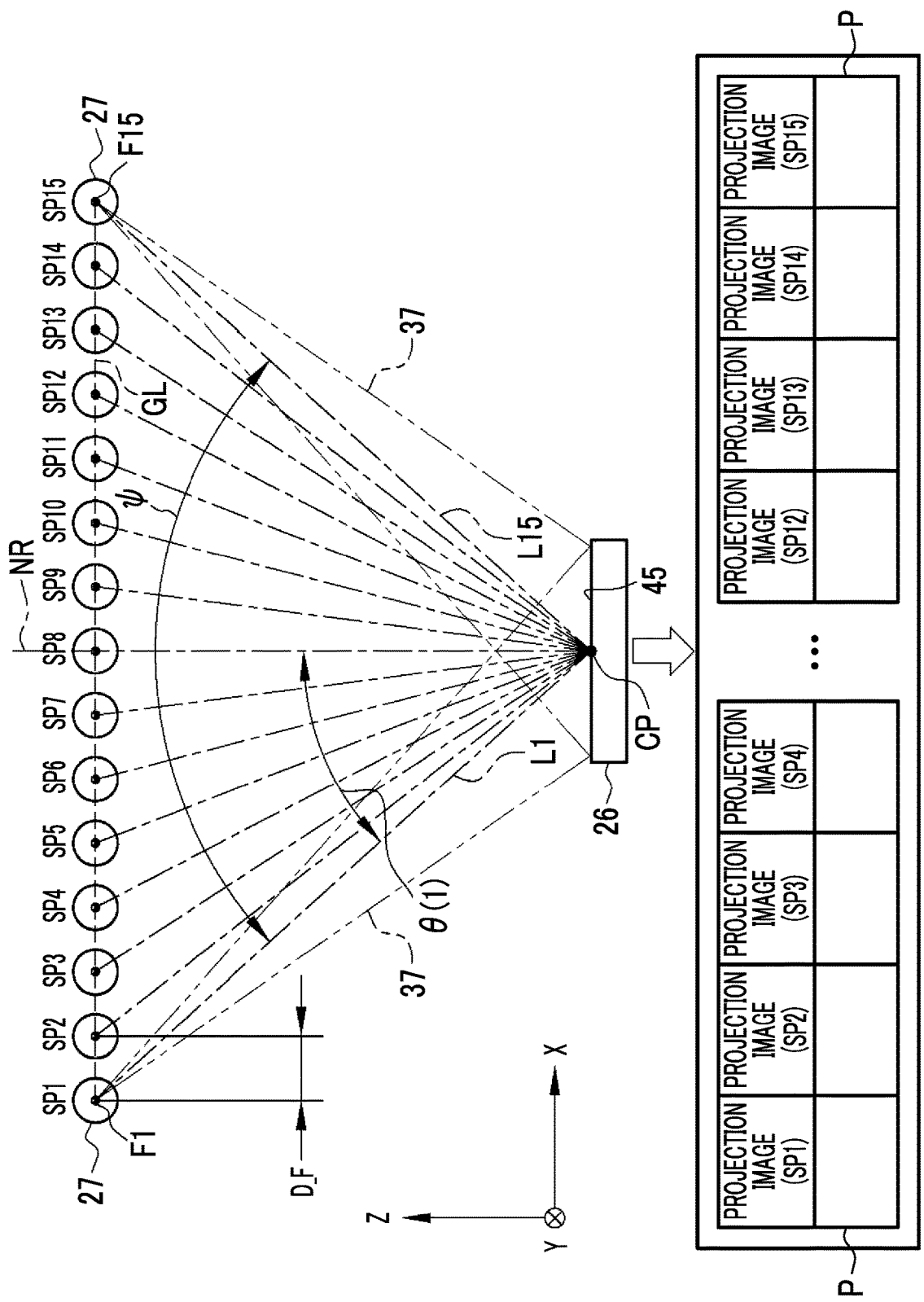
FIG. 7 is a diagram illustrating an aspect of tomosynthesis imaging.

In FIG. 7 which is a plan view illustrating the radiation source 25 and the radiation detector 26 as viewed from the support 20B, it is assumed that a direction normal to the imaging surface 45 is the Z direction, a direction along a side of the imaging surface 45 is the X direction, and a depth direction of the imaging surface 45 which is orthogonal to the Z direction and the X direction is the Y direction. The radiation tubes 27 are provided at a total of 15 positions SP1, SP2, . . . , SP14, and SP15 where the radiation 37 is emitted to the imaging surface 45 at different irradiation angles. The focuses F1 to F15 of the radiation 37 in the radiation tubes 27 at the positions SP1 to SP15 are arranged in a linear shape at equal intervals D_F.

Further, the position SP8 is disposed on a normal line NR to the imaging surface 45 which extends from a center point CP of the side of the imaging surface 45 in the X direction. Positions other than the position SP8 are set so as to be bilaterally symmetric with respect to the normal line NR such that the positions SP1 to SP7 are disposed on the left side of the normal line NR and the positions SP9 to SP15 are disposed on the right side of the normal line NR. That is, the radiation tubes 27 at the positions SP1 to SP7 and the radiation tubes 27 at the positions SP9 to SP15 are disposed at positions that are symmetric with respect to a line.

Here, a straight line GL on which the positions SP1 to SP15 are set is parallel to the side of the imaging surface 45 in the X direction in a plan view of the radiation source 25 and the radiation detector 26 from the Z direction. That is, the X direction is an example of an "arrangement direction of radiation tubes" according to the technique of the present disclosure. The straight line GL is offset to the front side (a side opposite to the support 20B) in the Y direction. The present disclosure is not limited to a case in which the intervals D_F between the focuses F1 to F15 are exactly equal to each other. For example, an error of ±5% is allowed in the interval D_F.

The irradiation angle of the radiation 37 is an angle formed between the normal line NR and a line connecting the center point CP and each of the focuses F1 to F15 of the radiation 37 in the radiation tubes 27 at the positions SP1 to SP15. Therefore, the irradiation angle at the position SP8 aligned with the normal line NR is 0°. FIG. 7 illustrates a line L1 connecting the focus F1 at the position SP1 and the center point CP and an irradiation angle θ(1) formed between the normal line NR and the line L1 as an example.

An angle represented by a symbol Ψ is the maximum scanning angle of tomosynthesis imaging. The maximum scanning angle Ψ is defined by the positions SP1 and SP15 at both ends among the positions SP1 to SP15. Specifically, the maximum scanning angle Ψ is an angle formed between the line L1 connecting the focus F1 at the position SP1 and the center point CP and a line L15 connecting the focus F15 at the position SP15 and the center point CP.

In one normal tomosynthesis imaging operation, each of the radiation tubes 27 at the positions SP1 to SP15 is operated to emit the radiation 37 to the breast M at each of the positions SP1 to SP15. The radiation detector 26 detects the radiation 37 emitted at each of the positions SP1 to SP15 whenever the radiation 37 is emitted and outputs the projection images P at the positions SP1 to SP15. The tomosynthesis imaging can be performed by both the CC imaging method illustrated in FIG. 5 and the MLO imaging method illustrated in FIG. 6. In the case of simple imaging in which the CC imaging illustrated in FIG. 5 and the MLO imaging illustrated in FIG. 6 are independently performed, only the radiation tube 27 disposed at the position SP8 where the irradiation angle is 0° is operated.

Figure 8:
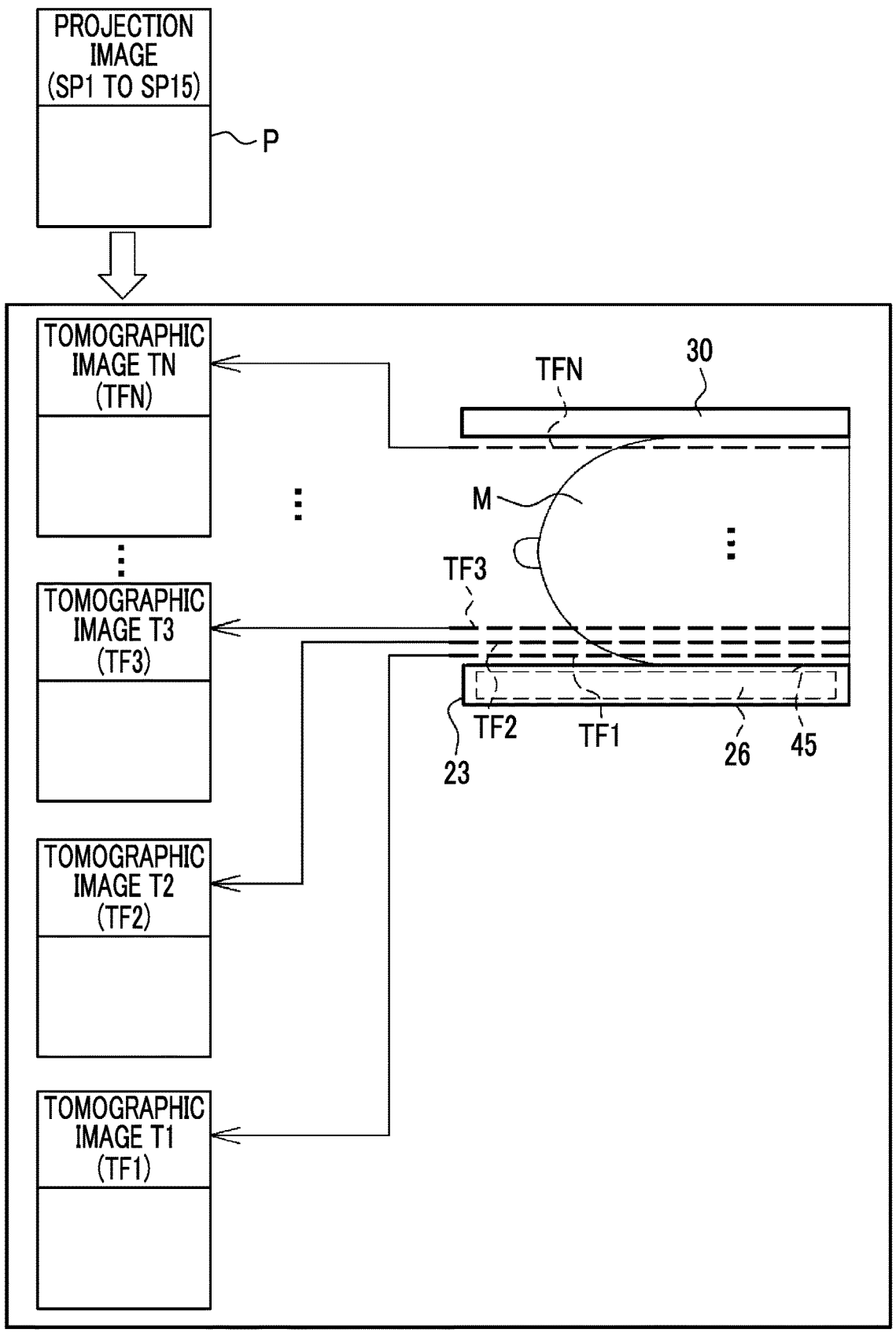
FIG. 8 is a diagram illustrating an aspect in which tomographic images are generated from a plurality of projection images obtained by the tomosynthesis imaging.

As illustrated in FIG. 8, in general, the mammography apparatus 10 generates tomographic images T1 to TN corresponding to any tomographic planes TF1 to TFN of the breast M from the plurality of projection images P at the plurality of positions SP1 to SP15 obtained by the tomosynthesis imaging illustrated in FIG. 7. The mammography apparatus 10 generates the tomographic images T1 to TN using a known method such as a filtered back projection method. The tomographic images T1 to TN are images in which structures in the tomographic planes TF1 to TFN have been highlighted. Adjacent radiation tubes 27 are disposed close to each other at a distance of, for example, several centimeters to several tens of centimeters in order to improve the SN ratio of the tomographic image T.

Figure 9:
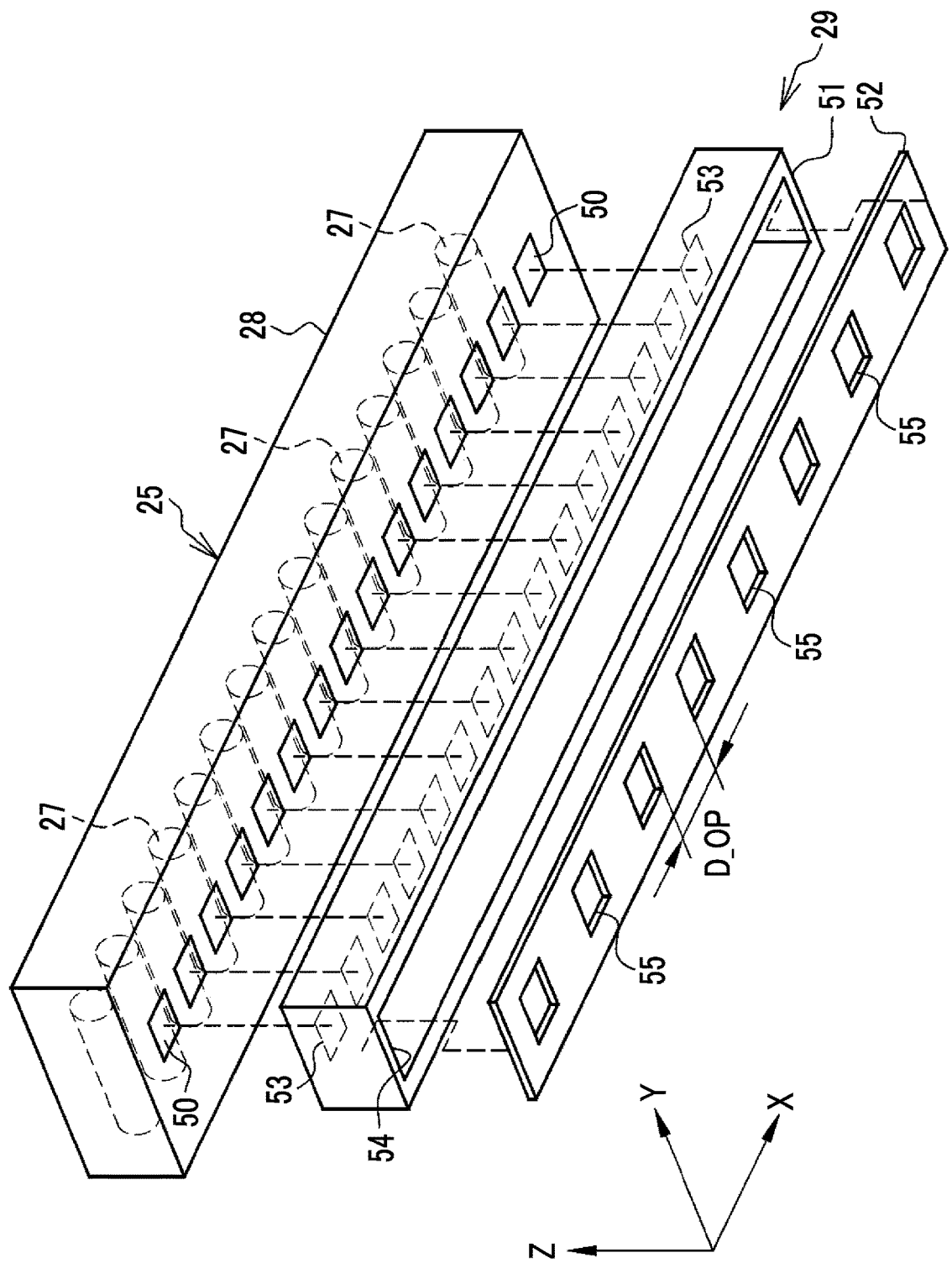
FIG. 9 is an exploded perspective view illustrating a radiation source and an irradiation field limiter.

As illustrated in FIG. 9, radiation transmission windows 50 that transmit the radiation 37 are provided in the lower surface of the housing 28 at corresponding positions immediately below each radiation tube 27. The radiation 37 emitted from each radiation tube 27 is emitted to the outside of the housing 28 through the radiation transmission windows 50.

The irradiation field limiter 29 includes a housing 51 and one plate-like member 52. Small openings 53 are provided in the upper surface of the housing 51 at positions corresponding to the radiation transmission windows 50 of the housing 28. A large opening 54 is provided in the lower surface of the housing 51. The lower surface of the housing 28 and the upper surface of the housing 51 are connected such that the radiation transmission windows 50 and the small openings 53 are aligned with each other. The radiation 37 emitted from the radiation transmission windows 50 is incident into the housing 51 through the small openings 53.

The plate-like member 52 is accommodated in the housing 51. The plate-like member 52 is made of a material shielding the radiation 37 such as lead. A total of eight through holes 55 are formed in the plate-like member 52 along the X direction. Adjacent through holes 55 are separated by an interval D_OP. The interval D_OP is nearly equal to an interval of one radiation tube 27. The through hole 55 functions as an irradiation opening for defining the irradiation field, which will be described below. The irradiation opening is defined by the through hole 55 of the plate-like member 52 and the radiation 37 that has been incident into the housing 51 through the small opening 53 exits to the imaging surface 45 of the radiation detector 26 through the large opening 54.

Figure 10:
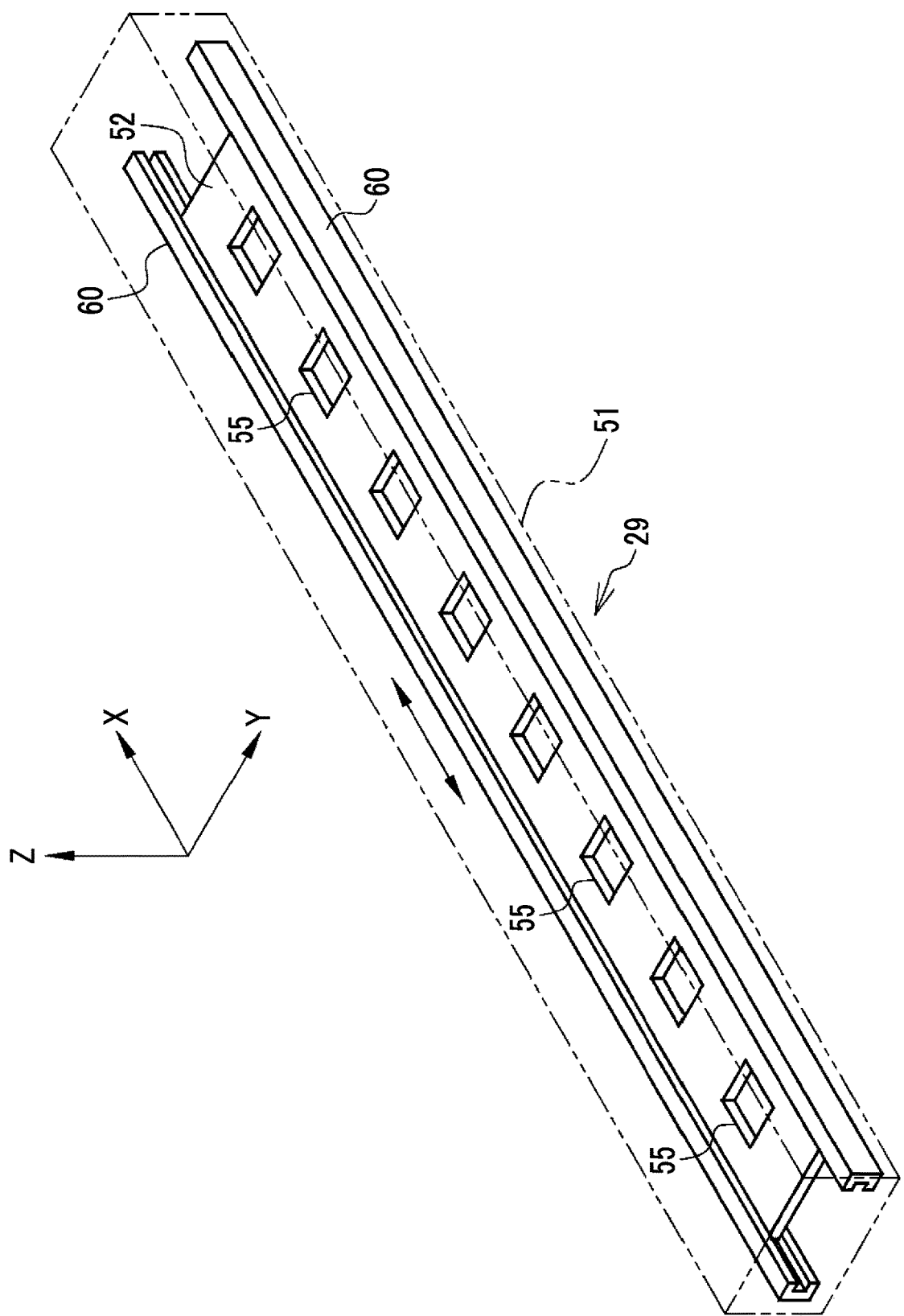
FIG. 10 is a diagram illustrating a state in which a plate-like member is held by rails in a housing.

As illustrated in FIG. 10, the plate-like member 52 is held in the housing 51 so as to be movable in the X direction by a pair of rails 60. Both ends of the plate-like member 52 in the Y direction are fitted to the rails 60. For example, bearings for facilitating the movement of the plate-like member 52 in the X direction are provided in the rails 60, which is not illustrated.

Figure 11:
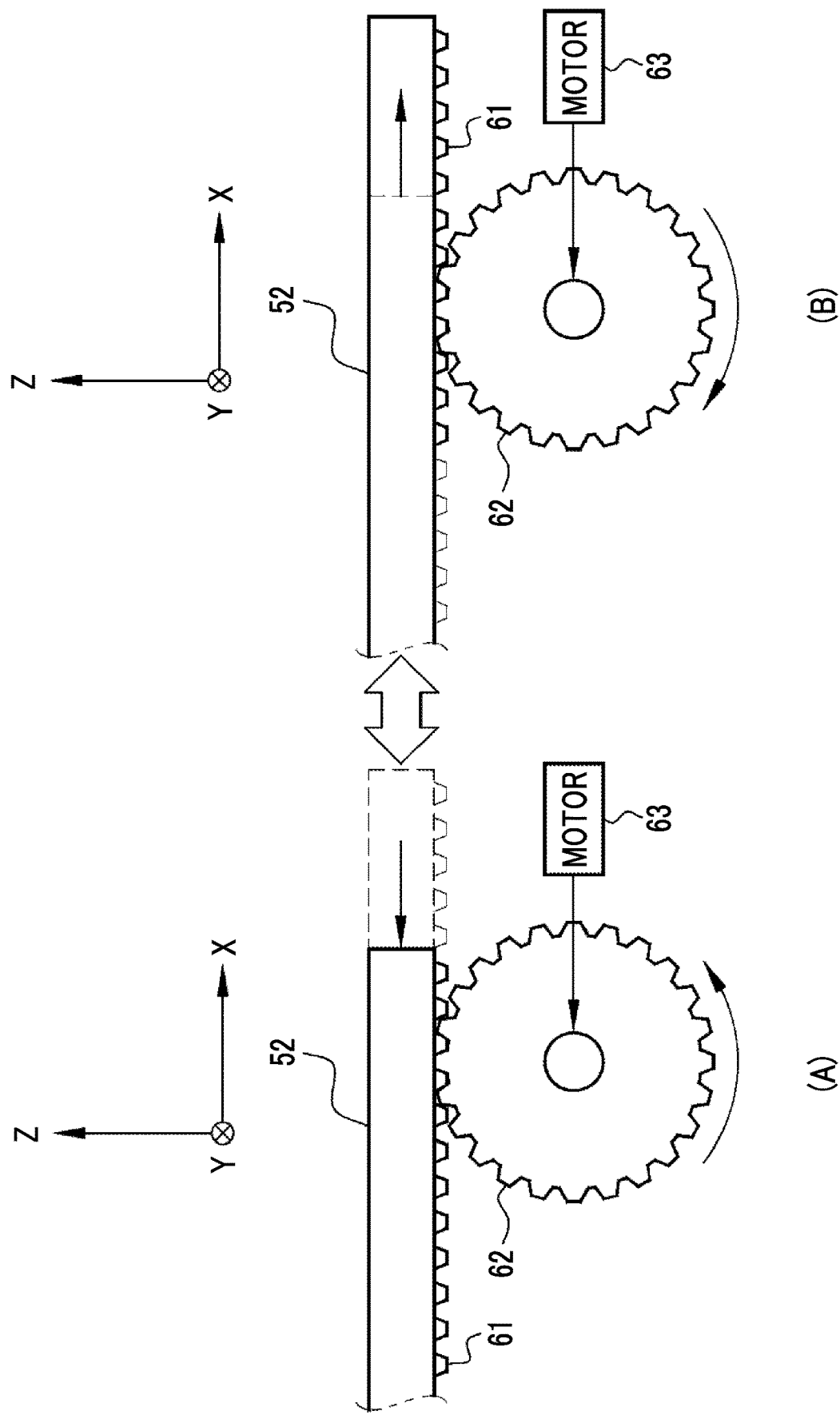
FIG. 11 is a diagram illustrating a portion of a displacement mechanism. (A) of FIG. 11 illustrates a case in which a pinion gear is rotated counterclockwise and (B) of FIG. 11 illustrates a case in which the pinion gear is rotated clockwise.

As illustrated in FIG. 11, a rack gear 61 is formed at a position that does not interfere with the rails 60 on the lower surface of one end of the plate-like member 52 in the X direction. The rack gear 61 is engaged with a pinion gear 62. The pinion gear 62 is rotated clockwise and counterclockwise by a motor 63. That is, the plate-like member 52 is reciprocated in the X direction by the rack and pinion. (A) of FIG. 11 illustrates a case in which the pinion gear 62 is rotated counterclockwise by the motor 63 and (B) of FIG. 11 illustrates a case in which the pinion gear 62 is rotated clockwise by the motor 63. The rails 60 illustrated in FIG. 10 and the rack gear 61, the pinion gear 62, and the motor 63 illustrated in FIG. 11 form a displacement mechanism 65 (see FIG. 15) that displaces the plate-like member 52 to move the through hole 55 functioning as the irradiation opening.

Figure 12:
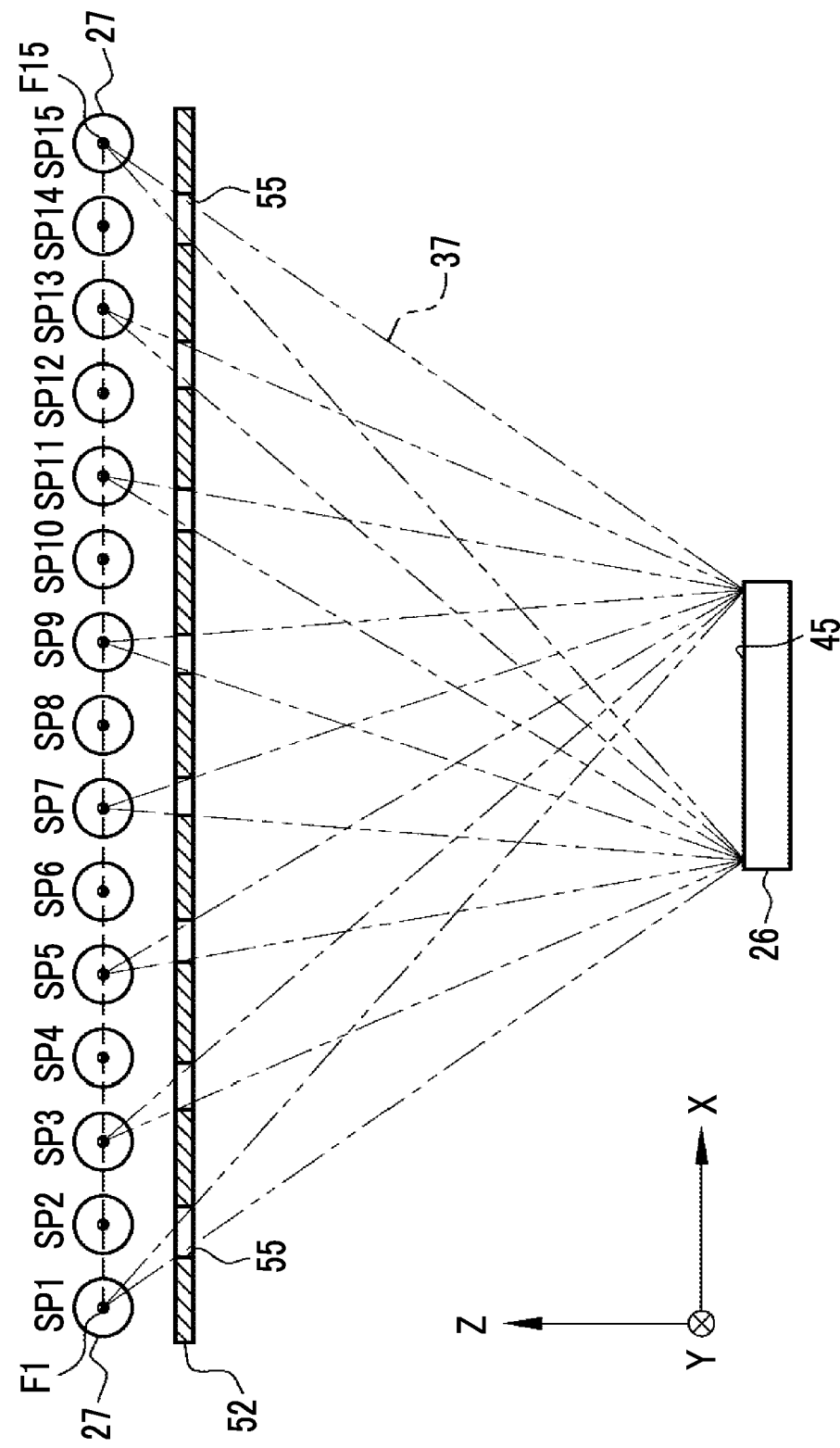
FIG. 12 is a diagram illustrating an aspect of the tomosynthesis imaging at a first set position.
Figure 13:
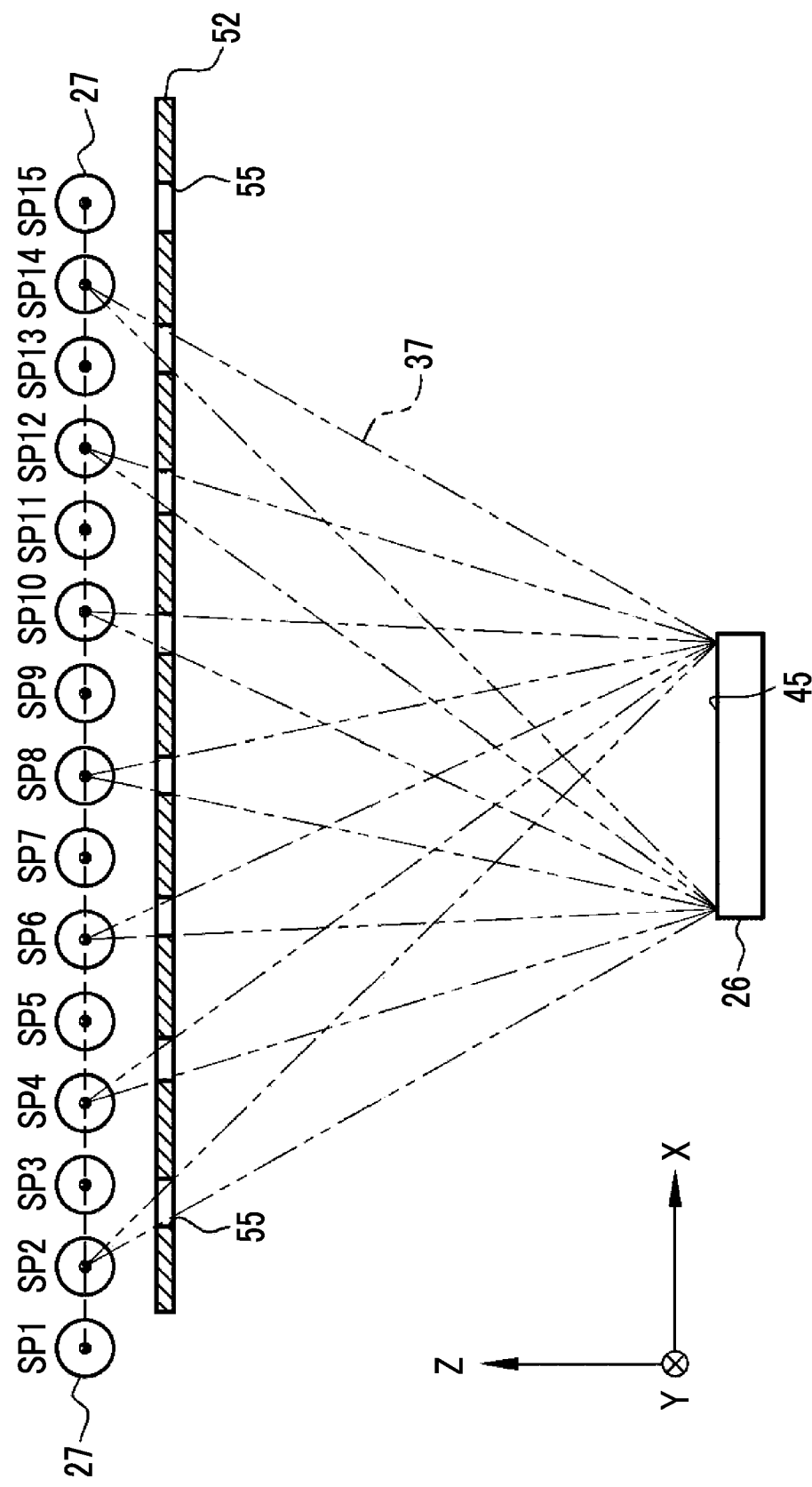
FIG. 13 is a diagram illustrating an aspect of the tomosynthesis imaging at a second set position.

The displacement mechanism 65 moves the plate-like member 52 to a first set position illustrated in FIG. 12 and a second set position illustrated in FIG. 13. As illustrated in FIG. 12, at the first set position, each through hole 55 of the plate-like member 52 functions as an irradiation opening for the radiation 37 emitted from the radiation tubes 27 disposed at the positions SP1, SP3, SP5, SP7, SP9, SP11, SP13, and SP15. That is, the radiation tubes 27 disposed at the positions SP1, SP3, SP5, SP7, SP9, SP11, SP13, and SP15 are an example of "first radiation tubes" according to the technique of the present disclosure.

In contrast, as illustrated in FIG. 13, at the second set position, each through hole 55 of the plate-like member 52 functions as an irradiation opening for the radiation 37 emitted from the radiation tubes 27 disposed at the positions SP2, SP4, SP6, SP8, SP10, SP12, and SP14. However, the through hole 55 corresponding to the radiation tube 27 at the position SP15 at the first set position is excluded. That is, the radiation tubes 27 disposed at the positions SP2, SP4, SP6, SP8, SP10, SP12, and SP14 is an example of "second radiation tubes" according to the technique of the present disclosure.

Figure 14:
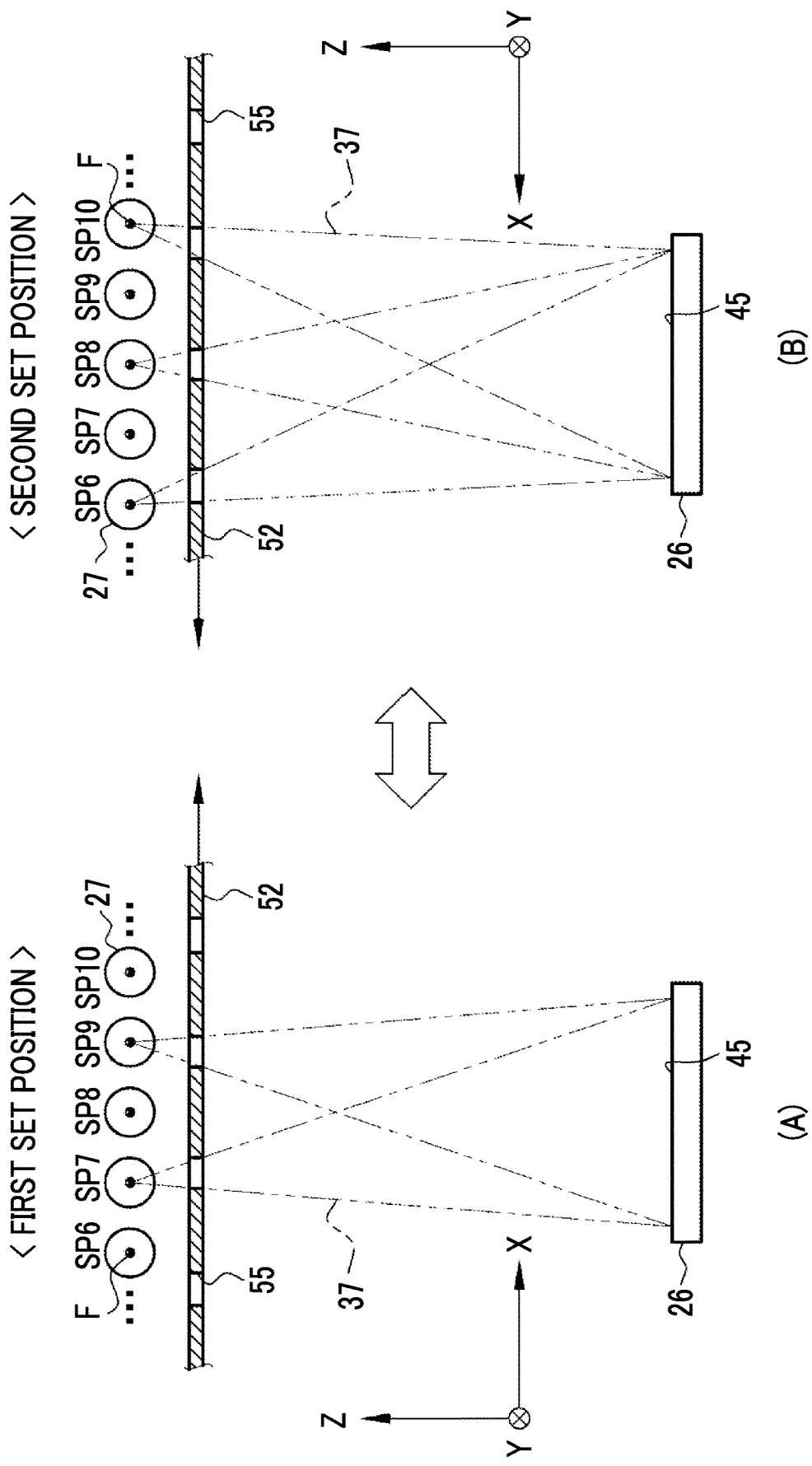
FIG. 14 is a diagram summarizing the content illustrated in FIG. 12 and FIG. 13. (A) of FIG. 14 illustrates a main portion in the case of the first set position illustrated in FIG. 12 and (B) of FIG. 14 illustrates the main portion in the case of the second set position illustrated in FIG. 13.

FIG. 14 illustrates a summary of the content illustrated in FIGS. 12 and 13. (A) of FIG. 14 illustrates a main portion in the case of the first set position illustrated in FIG. 12. In contrast, (B) of FIG. 14 illustrates a main portion in the case of the second set position illustrated in FIG. 13.

As illustrated in FIG. 9, adjacent through holes 55 are separated from each other by the interval D_OP that is nearly equal to an interval of one radiation tube 27. Therefore, at the first set position illustrated in FIG. 12 and (A) of FIG. 14, the through holes 55 do not face the radiation tubes 27 disposed at the positions SP2, SP4, SP6, SP8, SP10, SP12, and SP14. In contrast, at the second set position illustrated in FIG. 13 and (B) of FIG. 14, the through holes 55 do not face the radiation tubes 27 disposed at the positions SP1, SP3, SP5, SP7, SP9, SP11, SP13, and SP15.

Figure 15:
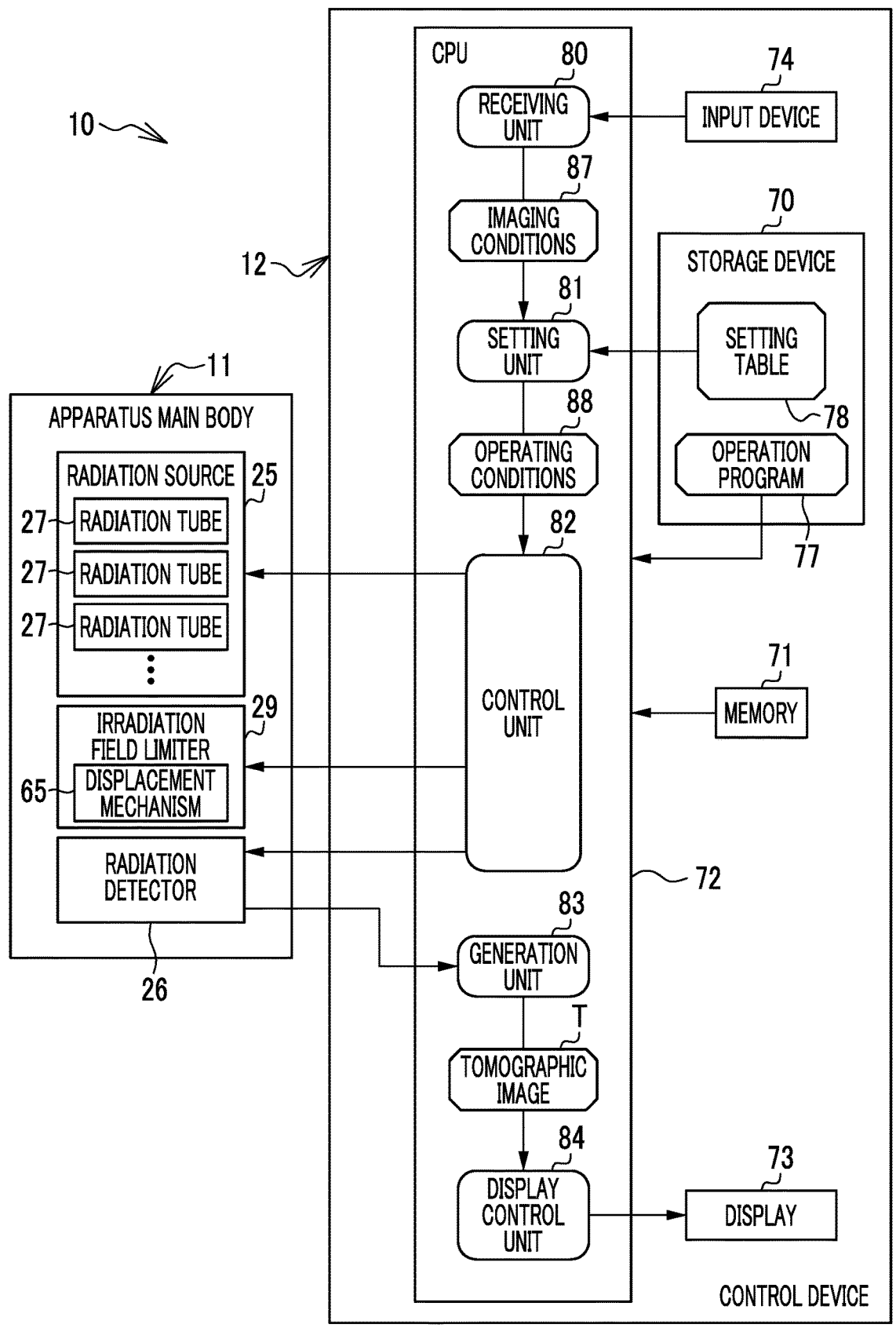
FIG. 15 is a block diagram mainly illustrating a processing unit of a CPU of a control device.

In FIG. 15, the computer forming the control device 12 comprises, for example, a storage device 70, a memory 71, a central processing unit (CPU) 72, a display 73, and an input device 74.

The storage device 70 is a hard disk drive that is provided in the computer forming the control device 12 or is connected to the computer through a cable or a network. Alternatively, the storage device 70 is a disk array in which a plurality of hard disk drives are connected. The storage device 70 stores a control program, such as an operating system, various application programs, and various kinds of data associated with these programs. In addition, a solid state drive may be used instead of the hard disk drive.

The memory 71 is a work memory used by the CPU 72 to perform processes. The CPU 72 loads the program stored in the storage device 70 to the memory 71 and performs a process corresponding to the program to control the overall operation of each unit of the computer.

The display 73 displays various screens. The various screens have operation functions by a graphical user interface (GUI). The computer forming the control device 12 receives operation commands input from the input device 74 through various screens. The input device 74 is, for example, a keyboard, a mouse, or a touch panel.

An operation program 77 is stored in the storage device 70. The operation program 77 is an application program for causing the computer to function as the control device 12. The storage device 70 stores a setting table 78 in addition to the operation program 77.

In a case in which the operation program 77 is started, the CPU 72 of the control device 12 functions as a receiving unit 80, a setting unit 81, a control unit 82, a generation unit 83, and a display control unit 84 in cooperation with, for example, the memory 71.

The receiving unit 80 receives imaging conditions 87 input by the operator through the input device 74. The receiving unit 80 outputs the imaging conditions 87 to the setting unit 81.

The setting unit 81 receives the imaging conditions 87 from the receiving unit 80. In addition, the setting unit 81 reads out the setting table 78 from the storage device 70. The setting unit 81 sets the operating conditions 88 of the radiation tubes 27 and the displacement mechanism 65 on the basis of the imaging conditions 87 and the setting table 78. The setting unit 81 outputs the operating conditions 88 to the control unit 82.

The control unit 82 controls the operation of the radiation source 25, the radiation detector 26, and the irradiation field limiter 29. The control unit 82 receives the operating conditions 88 from the setting unit 81. The control unit 82 operates the radiation tubes 27 and the displacement mechanism 65 on the basis of the operating conditions 88 such that the radiation tubes 27 emit the radiation 37. The control unit 82 outputs the projection image P detected by the radiation detector 26 by the emission of the radiation 37 from the radiation detector 26 to the generation unit 83.

The generation unit 83 receives the plurality of projection images P from the radiation detector 26. The generation unit 83 generates tomographic images T on the basis of the plurality of projection images P. The generation unit 83 outputs the tomographic images T to the display control unit 84.

The display control unit 84 receives the tomographic images T from the generation unit 83. The display control unit 84 performs control to display the received tomographic images T on the display 73.

Figure 16:
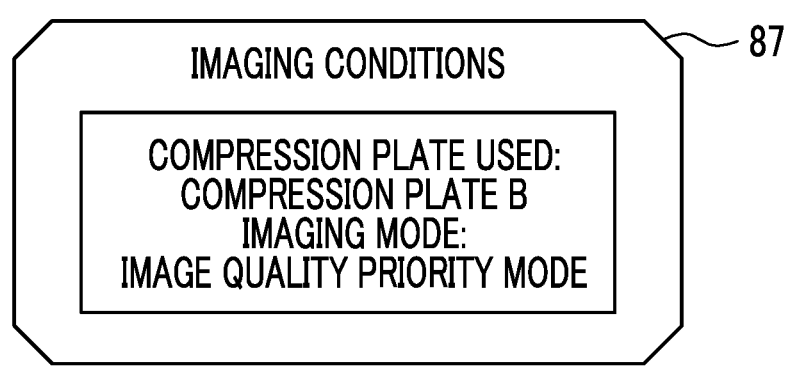
FIG. 16 is a diagram illustrating imaging conditions.

As illustrated in FIG. 16, the imaging conditions 87 include the compression plate 30 used (described as a compression plate used in FIG. 16) and an imaging mode. As described above, the compression plate 30 is interchanged according to, for example, the size of the breast M. In the tomosynthesis imaging, the radiation tube 27 that emits the radiation 37 varies depending on the compression plate 30 used (see FIG. 17). Therefore, the compression plate 30 used is included in the imaging conditions 87.

The imaging mode includes an image quality priority mode and an exposure reduction mode (see FIG. 17). The image quality priority mode is a mode in which the radiation 37 is emitted from as many radiation tubes 27 as possible to increase the SN ratio of the tomographic image. In contrast, the exposure reduction mode is a mode in which the minimum amount of radiation 37 is emitted to reduce the exposure of the subject H as much as possible. Since the radiation tube 27 that emits the radiation 37 varies depending on each of the imaging modes (see FIG. 17), the imaging mode is included in the imaging conditions 87.

FIG. 16 illustrates imaging conditions 87 in which a compression plate B is registered as the compression plate 30 used and the image quality priority mode is registered as the imaging mode. In addition to the compression plate 30 used and the imaging mode, information for changing the radiation tube 27 that emits the radiation 37 may be added to the imaging conditions 87.

As illustrated in FIG. 17, in the setting table 78, the radiation tube identification data (ID) of the radiation tubes 27 (described as the radiation tubes used in FIG. 17) that emit the radiation 37 is registered for each combination of the compression plate 30 used and the imaging mode. For the radiation tube ID, numbers are linked to each of the positions SP1 to SP15. For example, the radiation tube 27 disposed at the position SP1 is represented by RT01, the radiation tube 27 disposed at the position SP2 is represented by RT02, . . . , the radiation tube 27 disposed at the position SP14 is represented by RT14, and the radiation tube 27 disposed at the position SP15 is represented by RT15.

In the exposure reduction mode, the number of radiation tubes 27 that emit the radiation 37 is smaller than that in the image quality priority mode. For example, in a case in which the compression plate 30 used is the compression plate B, a total of 13 radiation tubes 27 having the radiation tube IDs RT02 to RT14 are registered in the image quality priority mode. In contrast, in the exposure reduction mode, a total of seven radiation tubes 27 having the radiation tube IDs RT02, RT04, RT06, RT08, RT10, RT12, and RT14 are registered.

In FIG. 18, in the operating conditions 88, the radiation tube ID of the radiation tube 27 and the set position of the plate-like member 52 are registered for each irradiation number of the radiation 37. FIG. 18 illustrates the operating conditions 88 in a case in which the content of the imaging conditions 87 is as illustrated in FIG. 16, that is, is that the compression plate 30 used is the compression plate B and the imaging mode is the image quality priority mode. In a case in which the content of the imaging conditions 87 is as illustrated in FIG. 16, the setting table 78 illustrated in FIG. 17 shows that the radiation tubes 27 with the radiation tube IDs RT02 to RT14 emit the radiation 37. Therefore, in the operating conditions 88, first, for irradiation numbers 1 to 6, RT03, RT05, RT07, RT09, RT11, and RT13 are registered as the radiation tube IDs and the first set position is registered as the set position of the plate-like member 52. Then, for irradiation numbers 7 to 13, RT02, RT04, RT06, RT08, RT10, RT12, and RT14 are registered as the radiation tube IDs and the second set position is registered as the set position of the plate-like member 52.

In the case of the operating conditions 88 illustrated in FIG. 18, the control unit 82 performs control such that the radiation tubes 27 with the radiation tube IDs RT03, RT05, RT07, RT09, RT11, RT13, RT02, RT04, RT06, RT08, RT10, RT12, and RT14 emit the radiation 37 in this order. Further, the control unit 82 operates the displacement mechanism 65 between irradiation number 6 and irradiation number 7 to move the set position of the plate-like member 52 from the first set position to the second set position.

As another example, a case is considered in which the content of the imaging conditions 87 is that the compression plate 30 used is the compression plate B and the imaging mode is the exposure reduction mode. In this case, according to the setting table 78, the radiation tubes 27 with the radiation tube IDs RT02, RT04, RT06, RT08, RT10, RT12, and RT14 emit the radiation 37. Therefore, in this case, the plate-like member 52 is maintained at the second set position from beginning to end.

The control unit 82 recognizes whether the plate-like member 52 is at the first set position or the second set position on the basis of, for example, a detection signal of a linear encoder.

Figure 19:
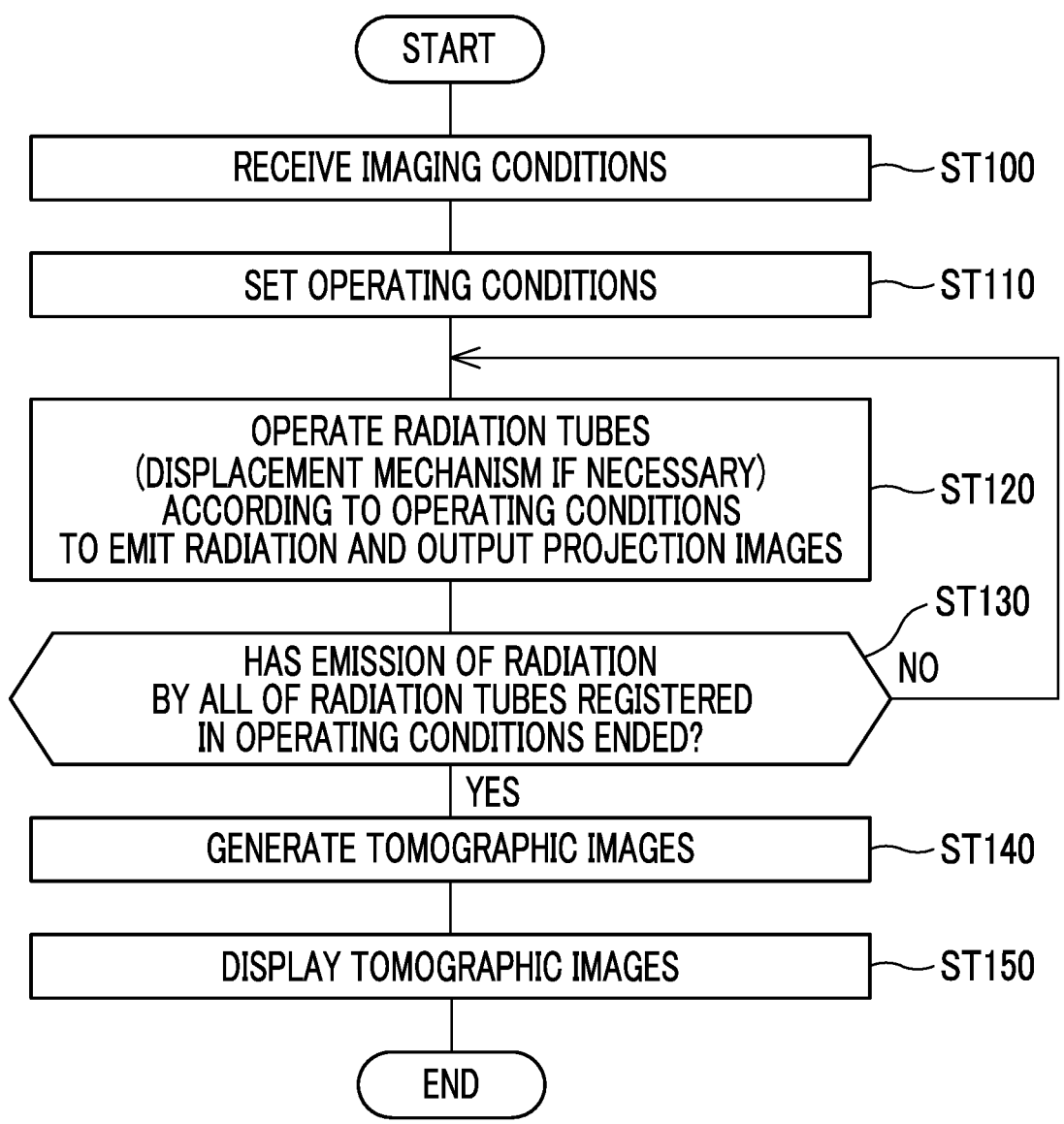
FIG. 19 is a flowchart illustrating a process procedure of the control device.

Next, the operation of the above-mentioned configuration will be described with reference to a flowchart illustrated in FIG. 19. In a case in which the operation program 77 is started, the CPU 72 of the control device 12 functions as the receiving unit 80, the setting unit 81, the control unit 82, the generation unit 83, and the display control unit 84 as illustrated in FIG. 15.

First, the receiving unit 80 receives the imaging conditions 87 (Step ST100). The imaging conditions 87 are output from the receiving unit 80 to the setting unit 81. Then, the setting unit 81 sets the operating conditions 88 on the basis of the imaging conditions 87 and the setting table 78 (Step ST110). The operating conditions 88 are output from the setting unit 81 to the control unit 82.

In Step ST120, the control unit 82 operates the radiation tubes 27 according to the operating conditions 88. The radiation 37 emitted from the radiation tubes 27 is incident into the irradiation field limiter 29 through the radiation transmission windows 50 and the small openings 53. The radiation 37 incident on the irradiation field limiter 29 passes through the through holes 55 of the plate-like member 52 which function as the irradiation openings. The irradiation field of the radiation 37 is defined in this way. As illustrated in FIG. 9, the through holes 55 are arranged at the interval D_OP that is nearly equal to an interval of one radiation tube 27. Therefore, in a case in which the radiation 37 is emitted from a certain radiation tube 27, the leakage of the radiation 37 from the adjacent through hole 55 is suppressed.

In Step ST120, the control unit 82 operates the displacement mechanism 65 on the basis of the operating conditions 88 to move the plate-like member 52 in the X direction, if necessary. As a result, the through hole 55 that functions as the irradiation opening is shared by two radiation tubes 27.

The irradiation field is defined by the through hole 55 and the radiation 37 emitted to the breast M is detected by the radiation detector 26. Then, the projection images P are output from the radiation detector 26 to the generation unit 83. Step ST120 is repeatedly performed in a case in which the emission of the radiation 37 by all of the radiation tubes 27 registered in the operating conditions 88 does not end (NO in Step ST130).

In a case in which the emission of the radiation 37 by all of the radiation tubes 27 registered in the operating conditions 88 ends (YES in Step ST130), the generation unit 83 generates the tomographic images T on the basis of the projection images P from the radiation detector 26 (Step ST140). The tomographic images T are output from the generation unit 83 to the display control unit 84. The tomographic images T are displayed on the display 73 by the display control unit 84 and are provided for the operator to browse (Step ST150).

As described above, the mammography apparatus 10 uses the irradiation field limiter 29 which has a plurality of through holes 55 that are irradiation openings for the radiation 37 and are arranged at an interval D_OP of at least one radiation tube 27 and in which the position of the irradiation openings is moved to the first set position in a case in which the radiation 37 is emitted from first radiation tubes which are some of three or more radiation tubes 27 and the second set position in a case in which the radiation 37 is emitted from second radiation tubes different from the first radiation tubes among the three or more radiation tubes 27 with respect to the radiation source 25 having the three or more radiation tubes 27. Therefore, it is possible to prevent unnecessary exposure.

In this embodiment, the irradiation field limiter 29 includes the plate-like member 52 in which the through holes 55 functioning as the irradiation openings are formed. Then, the displacement mechanism 65 moves the plate-like member 52 along the X direction which is the arrangement direction of the radiation tubes 27 to move the through holes 55. Therefore, it is possible to define the irradiation field of the radiation 37 with a very simple configuration.

Figure 20:
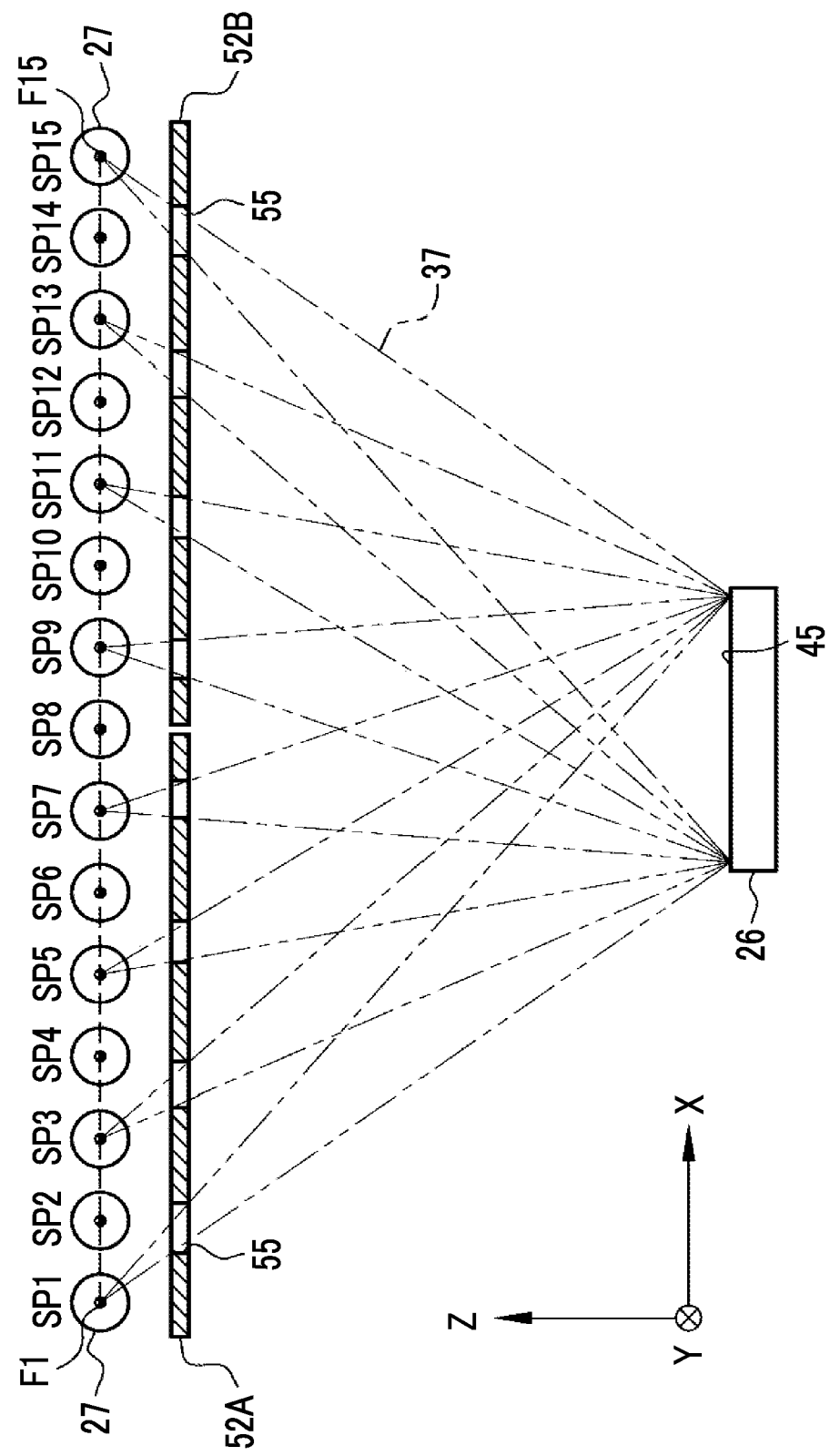
FIG. 20 is a diagram illustrating an example in which an irradiation field limiter includes a first plate-like member and a second plate-like member.

As illustrated in FIG. 20, the plate-like member 52 may be divided into a first plate-like member 52A and a second plate-like member 52B. The first plate-like member 52A defines irradiation openings for the radiation 37 emitted from the radiation tubes 27 disposed at the positions SP1 to SP8. Further, the second plate-like member 52B defines irradiation openings for the radiation 37 emitted from the radiation tubes 27 disposed at the positions SP9 to SP15.

Specifically, the through holes 55 of the first plate-like member 52A function as the irradiation openings for the radiation 37 emitted from the radiation tubes 27 disposed at the positions SP1, SP3, SP5, and SP7 at the first set position. In contrast, the through holes 55 of the first plate-like member 52A function as the irradiation openings for the radiation 37 emitted from the radiation tubes 27 disposed at the positions SP2, SP4, SP6, and SP8 at the second set position. Further, the through holes 55 of the second plate-like member 52B function as the irradiation openings for the radiation 37 emitted from the radiation tubes 27 disposed at the positions SP9, SP11, SP13, and SP15 at the first set position. In contrast, the through holes 55 of the second plate-like member 52B function as the irradiation openings for the radiation 37 emitted from the radiation tubes 27 disposed at the positions SP10, SP12, and SP14 at the second set position. The first plate-like member 52A and the second plate-like member 52B are moved to the first set position and the second set position at the same timing.

Figure 21:
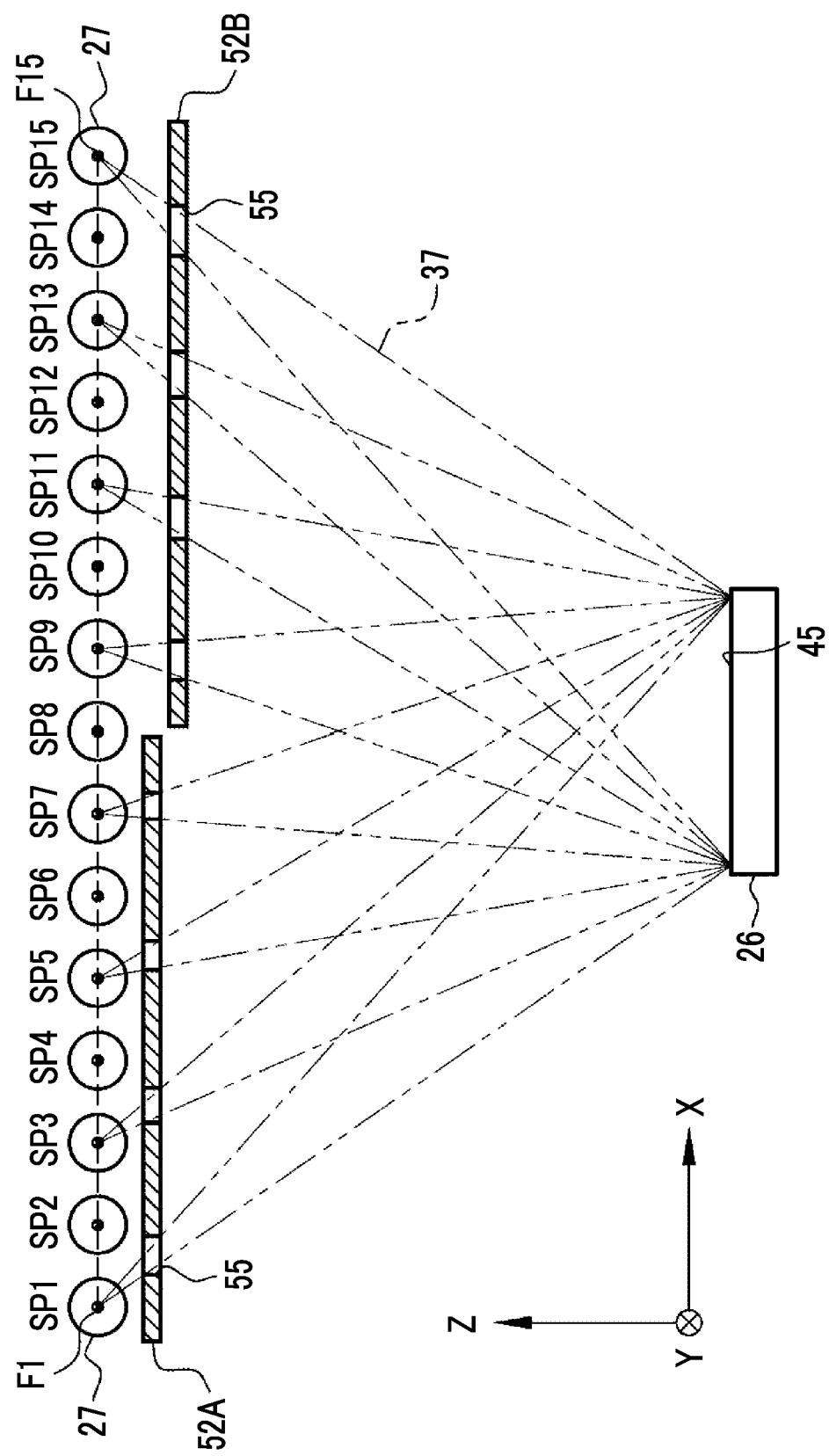
FIG. 21 is a diagram illustrating another example in which the irradiation field limiter is formed by the first plate-like member and the second plate-like member.
Figure 22:
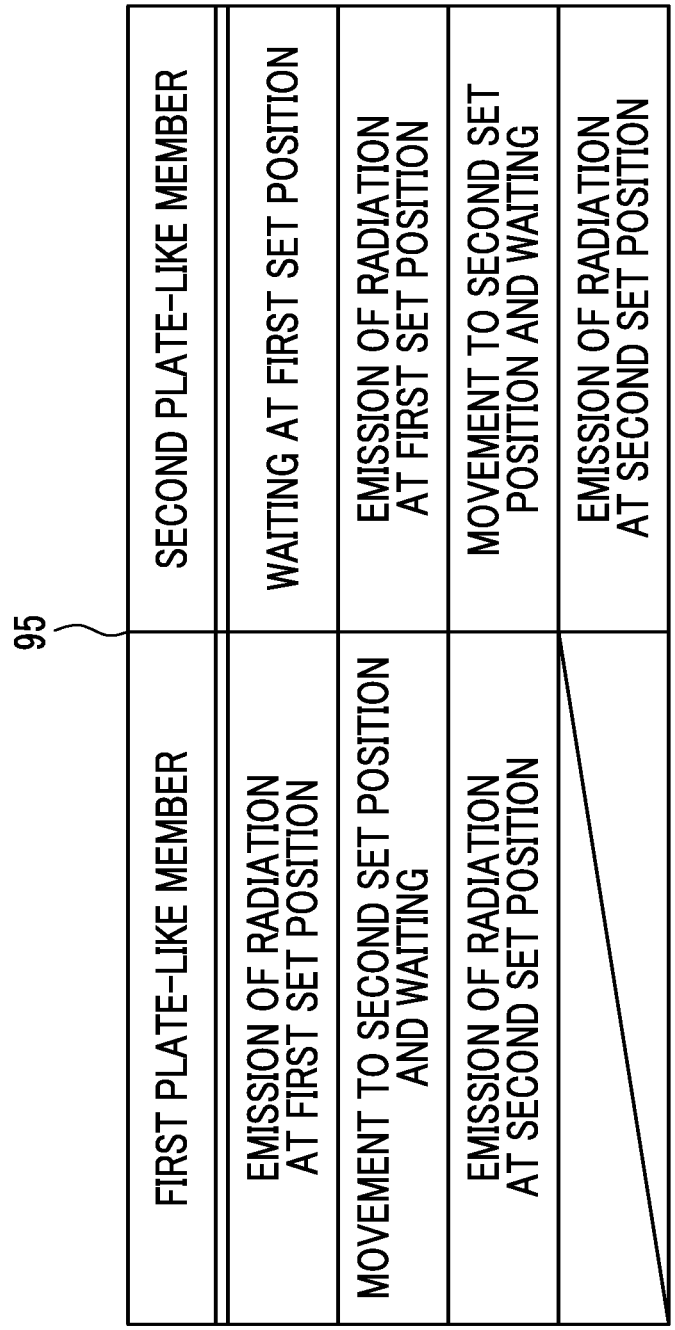
FIG. 22 is a table illustrating an operation procedure in the case of FIG. 21.

FIG. 21 illustrates an example in which the first plate-like member 52A and the second plate-like member 52B deviate in the Z direction so as not to interfere with each other in the X direction. In this case, as illustrated in a table 95 of FIG. 22, while the radiation 37 is emitted in a state in which the second plate-like member 52B is at the first set position, the first plate-like member 52A can be moved to the second set position. Further, while the radiation 37 is emitted in a state in which the first plate-like member 52A is at the second set position, the second plate-like member 52B can be moved to the second set position. In the first embodiment and FIG. 20, the emission of the radiation 37 and the movement of the plate-like member 52 need to be performed separately. However, according to the example illustrated in FIG. 21, the emission of the radiation 37 and the movement of the plate-like member 52 can be performed together. Therefore, it is possible to reduce the imaging time.

In the following embodiments, the description will be made on the premise that 15 radiation tubes 27 are disposed at the positions SP1 to SP15 as in the first embodiment.

Second Embodiment

Figure 23:
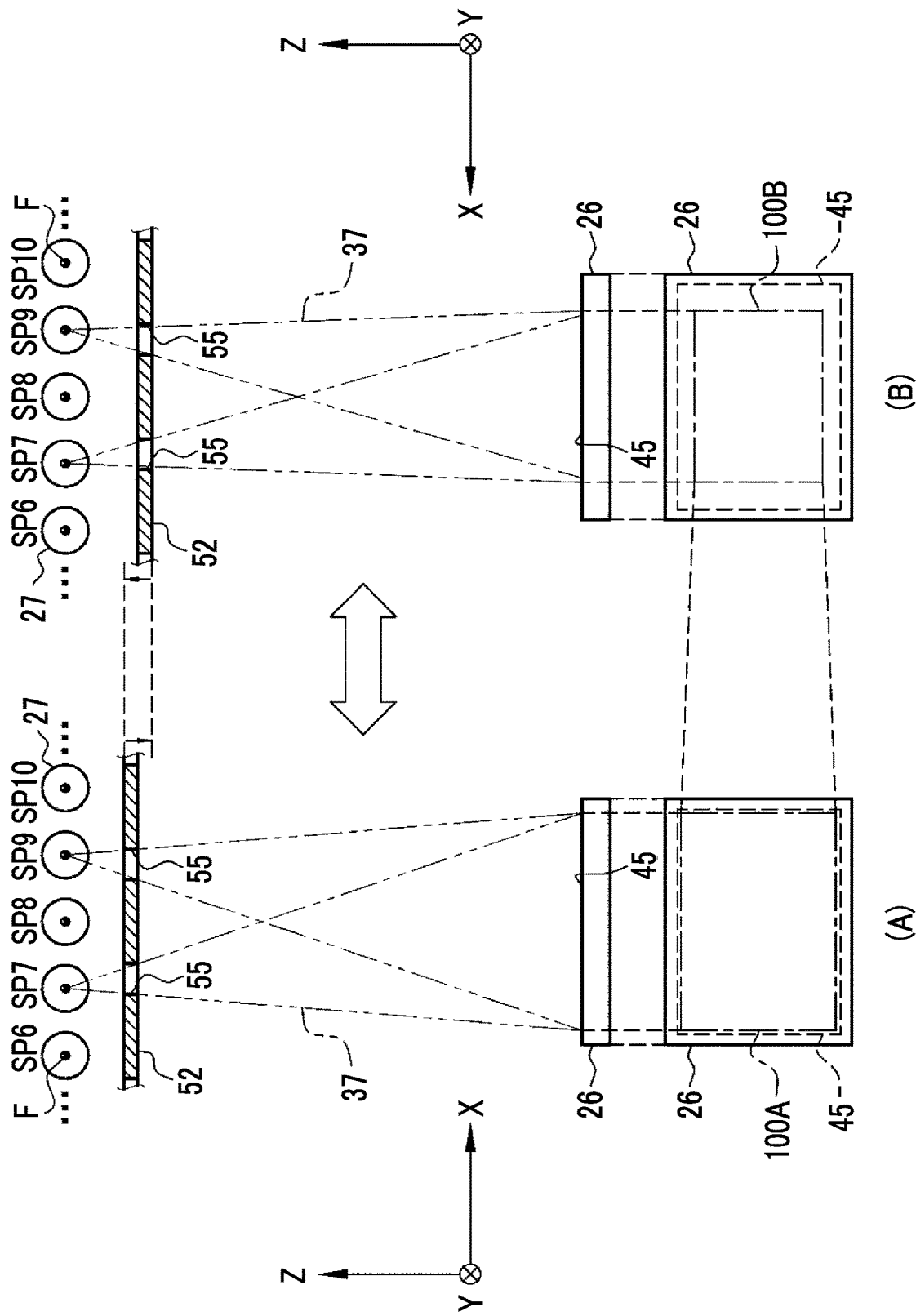
FIG. 23 is a diagram illustrating a second embodiment in which a plate-like member is moved in a direction in which an interval between the radiation tube and the through hole changes. (A) of FIG. 23 illustrates a case in which the interval between the radiation tube and the through hole is short and (B) of FIG. 23 illustrates a case in which the interval between the radiation tube and the through hole is long.

In a second embodiment illustrated in FIG. 23, the plate-like member 52 is moved in a direction in which the interval between the radiation tube 27 and the through hole 55 changes.

As illustrated in FIG. 23, in the second embodiment, the plate-like member 52 is moved not only in the X direction but also in the Z direction. Therefore, the interval between the radiation tube 27 and the through hole 55 changes. That is, the Z direction is an example of a "direction in which the interval between the radiation tube and the through hole changes" according to the technique of the present disclosure. As a method for moving the plate-like member 52 in the Z direction, a method can be adopted in which the rack and pinion illustrated in FIG. 11 is also provided for the Z direction. Alternatively, the plate-like member 52 may be moved up and down in the Z direction by wires and pulleys. The displacement mechanism 65 also includes a mechanism that moves the plate-like member 52 in the Z direction.

(A) of FIG. 23 illustrates a case in which the plate-like member 52 is moved to the radiation tube 27 and the interval between the radiation tube 27 and the through hole 55 decreases. In contrast, (B) of FIG. 23 illustrates a case in which the plate-like member 52 is moved to the radiation detector 26 and the interval between the radiation tube 27 and the through hole 55 increases. In (A) of FIG. 23, the irradiation field defined by the through hole 55 has substantially the same size as the imaging surface 45 of the radiation detector 26, as represented by a one-dot chain line and reference numeral 100A. In contrast, in (B) of FIG. 23, the size of the irradiation field defined by the through hole 55 is slightly smaller than the size of the imaging surface 45, as represented by a one-dot chain line and reference numeral 100B. That is, in a case in which the plate-like member 52 is moved to the radiation detector 26 and the interval between the radiation tube 27 and the through hole 55 increases, the size of the irradiation field decreases.

As such, in the second embodiment, since the plate-like member 52 is moved in the direction in which the interval between the radiation tube 27 and the through hole 55 changes, it is possible to change the size of the irradiation field.

Third Embodiment

Figure 24:
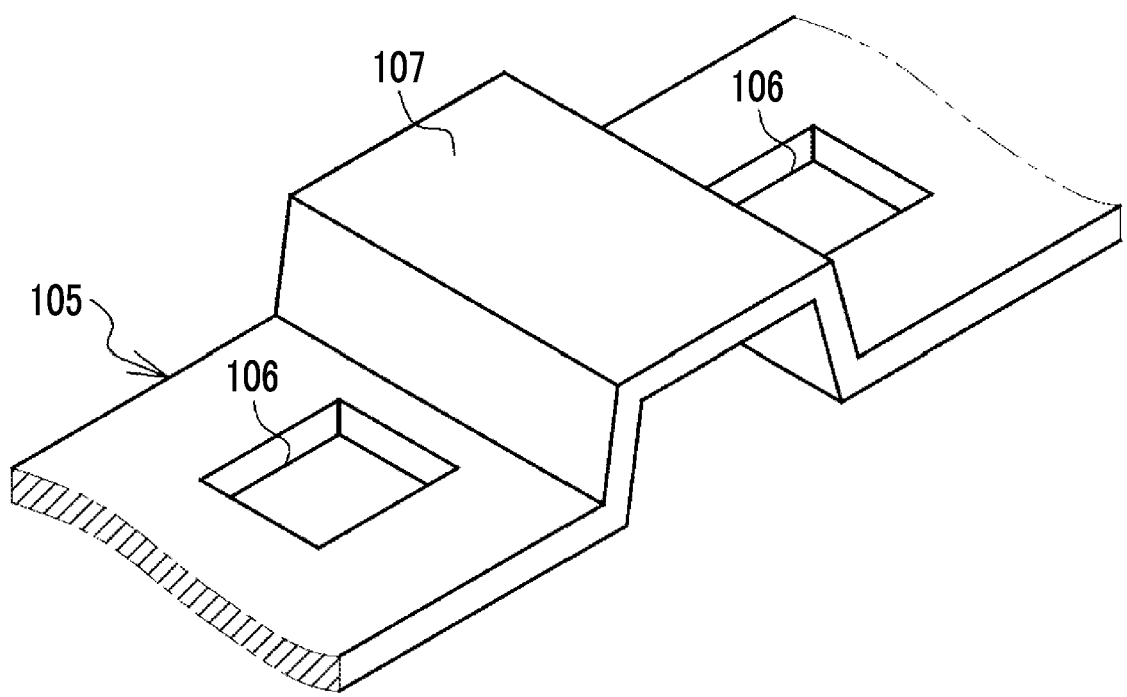
FIG. 24 is a perspective view illustrating a third embodiment in which a convex portion that protrudes toward the radiation tube is provided between adjacent through holes.
Figure 25:
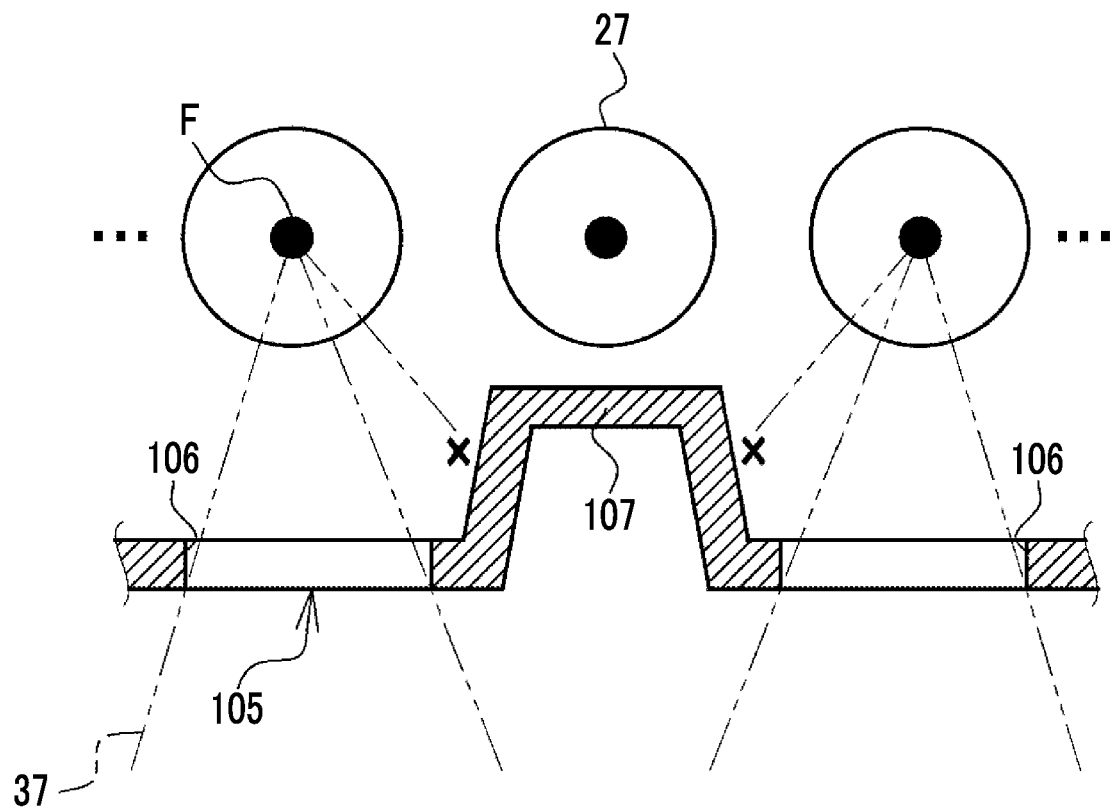
FIG. 25 is a partial cross-sectional view illustrating the third embodiment in which the convex portion that protrudes toward the radiation tube is provided between adjacent through holes.

In a third embodiment illustrated in FIGS. 24 and 25, a convex portion that protrudes toward the radiation tube 27 is provided between adjacent through holes of a plate-like member.

As illustrated in FIGS. 24 and 25, in a plate-like member 105 according to the third embodiment, a convex portion 107 that protrudes toward the radiation tube 27 is provided between adjacent through holes 106. Since the convex portion 107 is provided, the radiation 37 deviating from the through hole 106 is effectively shielded as represented by a cross mark in FIG. 25. Therefore, it is possible to more reliably prevent the radiation 37 from leaking from the adjacent through holes 106. Further, it is possible to further reduce the interval D_OP between the adjacent through holes 106. As a result, it is possible to make the adjacent radiation tubes 27 closer to each other and to further improve the SN ratio of the tomographic image T.

A rising surface of the convex portion 107 toward the radiation tube 27 may be inclined as illustrated in FIGS. 24 and 25 or may be vertical.

Fourth Embodiment

In a fourth embodiment illustrated in FIGS. 26 to 30, an irradiation field limiter having a configuration in which plate-like members are stacked is used.

Figure 26:
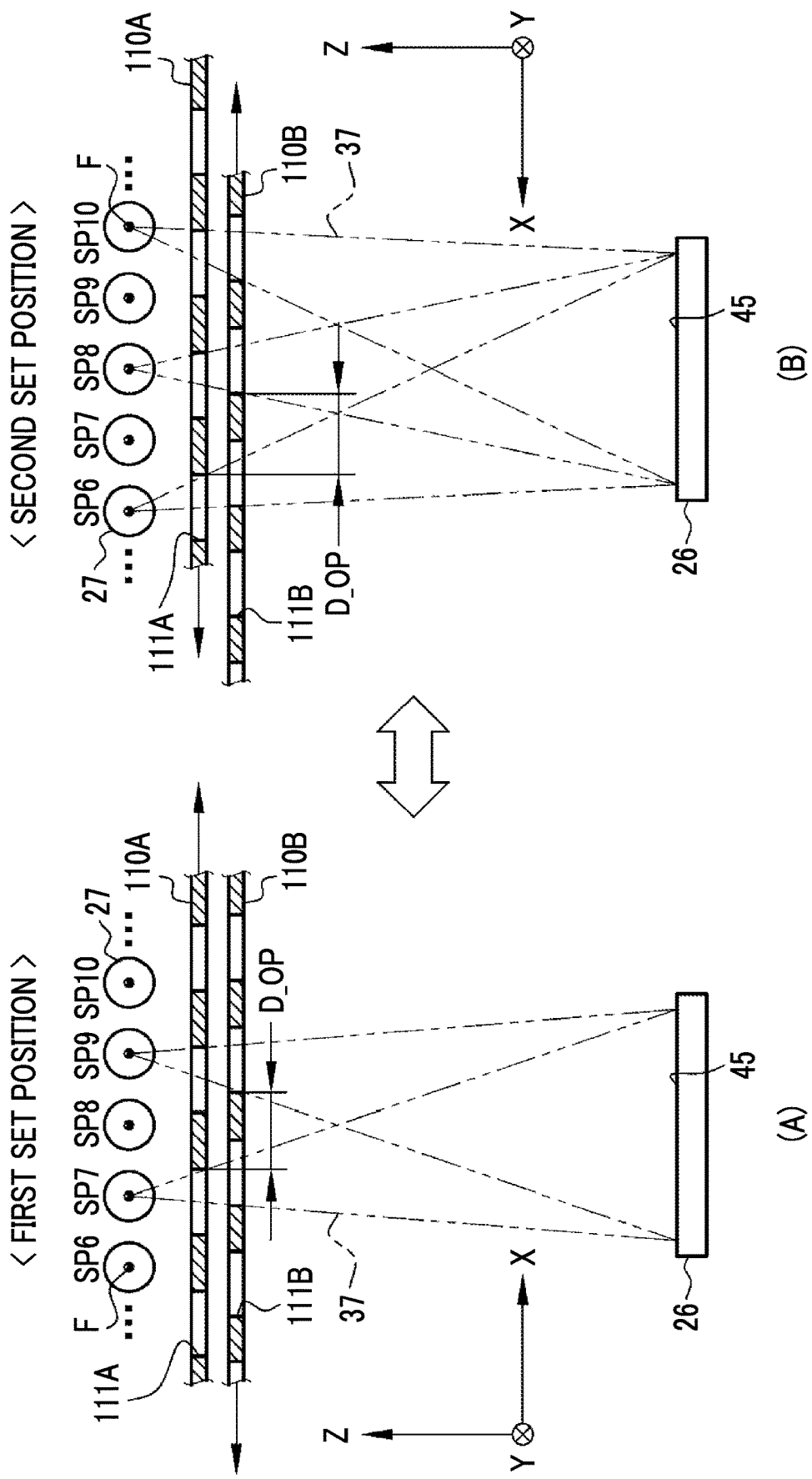
FIG. 26 is a diagram illustrating a fourth embodiment using an irradiation field limiter having a configuration in which plate-like members are stacked. (A) of FIG. 26 illustrates a first set position and (B) of FIG. 26 illustrates a second set position.

The irradiation field limiter illustrated in FIG. 26 has a configuration in which two plate-like members 110A and 110B are stacked in the Z direction which is a direction normal to the imaging surface 45 of the radiation detector 26. Through holes 111A are formed in the plate-like member 110A and through holes 111B are formed in the plate-like member 110B. The plate-like members 110A and 110B are held by rails (not illustrated) so as to be movable in the X direction, similarly to the plate-like member 52 according to the first embodiment.

As illustrated in (A) of FIG. 26, at the first set position, the through holes 111A and 111B of the plate-like members 110A and 110B function as irradiation openings for the radiation 37 emitted from the radiation tubes 27 disposed at the positions SP1, SP3, SP5, SP7, SP9, SP11, SP13, and SP15. In contrast, as illustrated in (B) of FIG. 26, at the second set position, the through holes 111A and 111B of the plate-like members 110A and 110B function as irradiation openings for the radiation 37 emitted from the radiation tubes 27 disposed at the positions SP2, SP4, SP6, SP8, SP10, SP12, and SP14.

Figure 27:
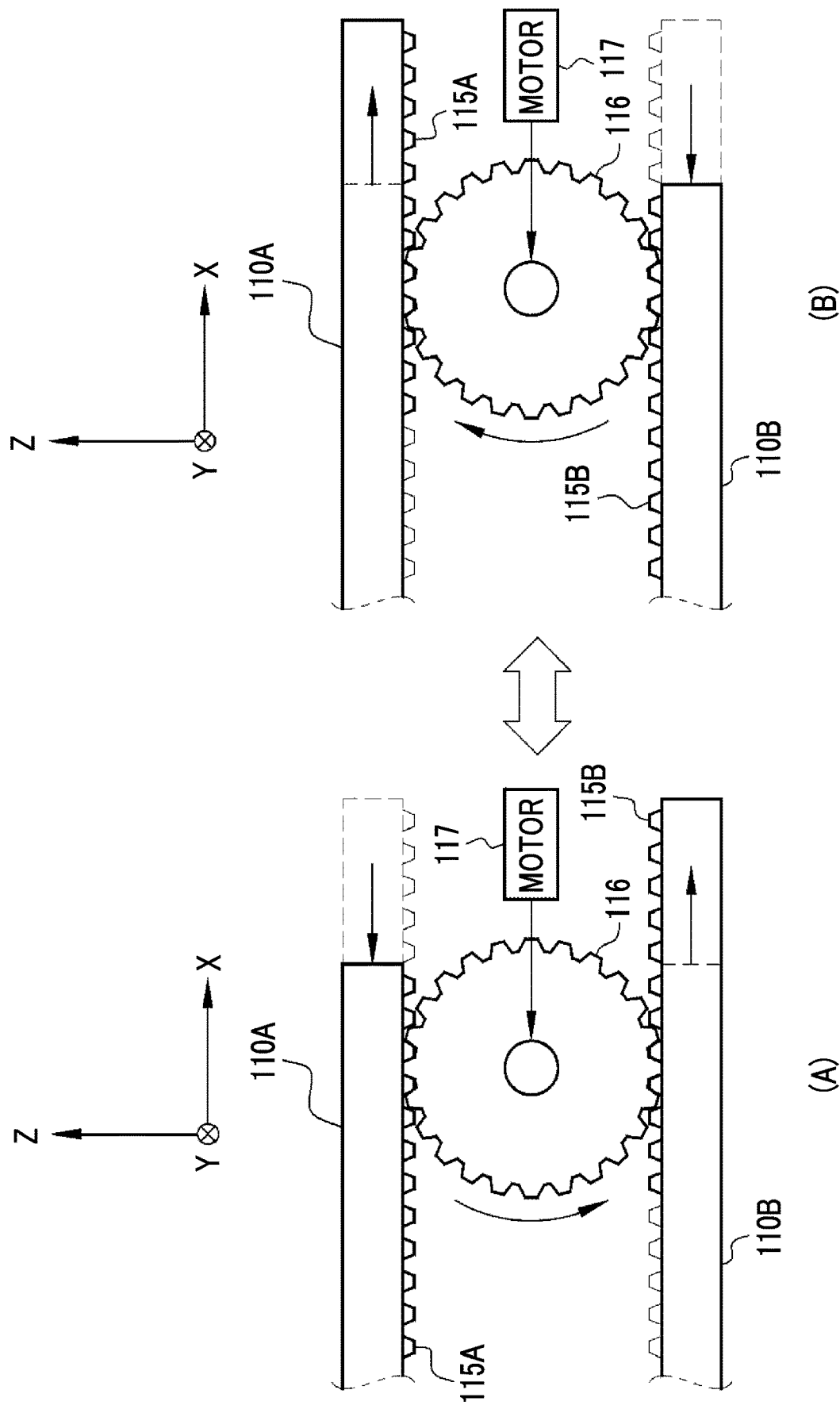
FIG. 27 is a diagram illustrating a portion of a displacement mechanism according to the fourth embodiment. (A) of FIG. 27 illustrates a case in which a pinion gear is rotated counterclockwise and (B) of FIG. 27 illustrates a case in which the pinion gear is rotated clockwise.

As illustrated in FIG. 27, a rack gear 115A is formed on the lower surface of one end of the plate-like member 110A in the X direction. Similarly, a rack gear 115B is formed on the upper surface of one end of the plate-like member 110B in the X direction. The rack gears 115A and 115B are engaged with a pinion gear 116. The pinion gear 116 is rotated clockwise and counterclockwise by a motor 117. That is, the plate-like members 110A and 110B are reciprocated in opposite directions in the X direction by the rack and pinion. As described above, the two plate-like members 110A and 110B that are adjacent to each other in the stacking direction are moved at the same time in the X direction by one motor 117. The motor 117 is an example of an "actuator" according to the technique of the present disclosure. (A) of FIG. 27 illustrates a case in which the pinion gear 116 is rotated counterclockwise by the motor 117 and (B) of FIG. 27 illustrates a case in which the pinion gear 116 is rotated clockwise by the motor 117. The rails (not illustrated) and the rack gears 115A and 115B, the pinion gear 116, and the motor 117 illustrated in FIG. 27 form a displacement mechanism.

Figure 28:
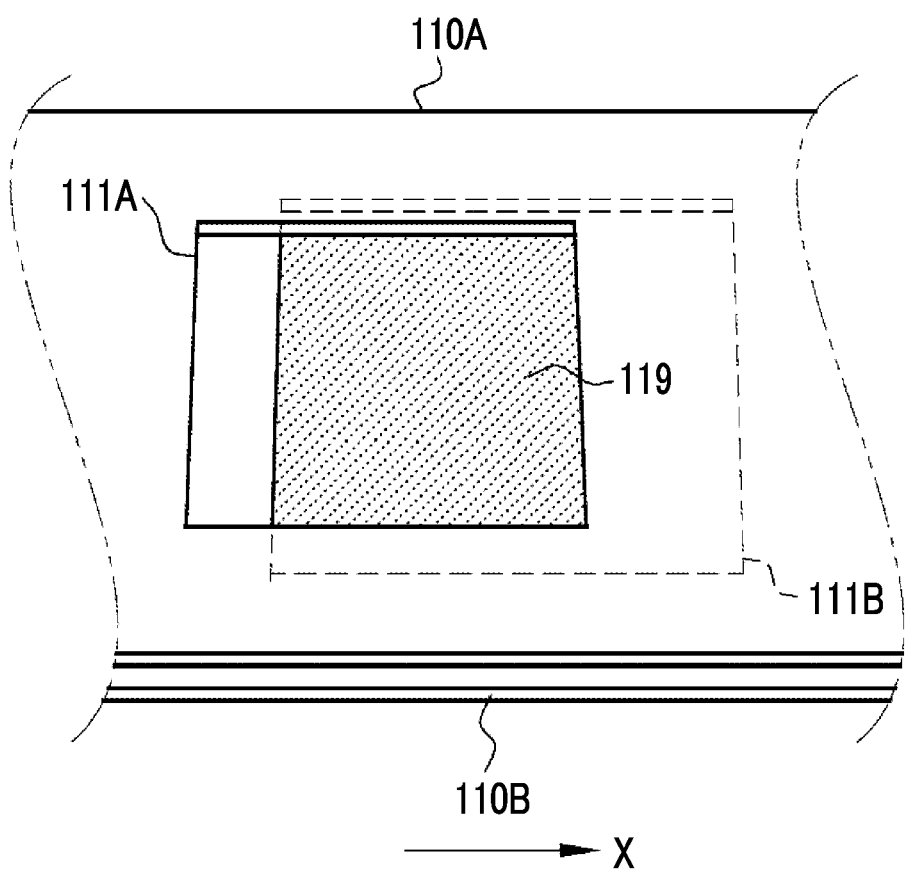
FIG. 28 is a diagram illustrating a plate-like member as viewed from the radiation tube side.

FIG. 28 is a diagram illustrating the plate-like members 110A and 110B as viewed from the radiation tube 27. Since the plate-like member 110B is located closer to the radiation detector 26 than the plate-like member 110A, the size of the through hole 111B of the plate-like member 110B is slightly larger than the size of the through hole 111A of the plate-like member 110A as illustrated in FIG. 28. An irradiation opening that is hatched and is denoted by reference numeral 119 is defined by three sides of the through hole 111A and one side of the through hole 111B. That is, at least one side of each of the through holes 111A and 111B functions as an opening edge of the irradiation opening 119. Therefore, the interval D_OP between the irradiation openings 119 defined by the through holes 111A and 111B is an interval of at least one radiation tube 27, as in the first embodiment (see FIG. 26).

Figure 29A:
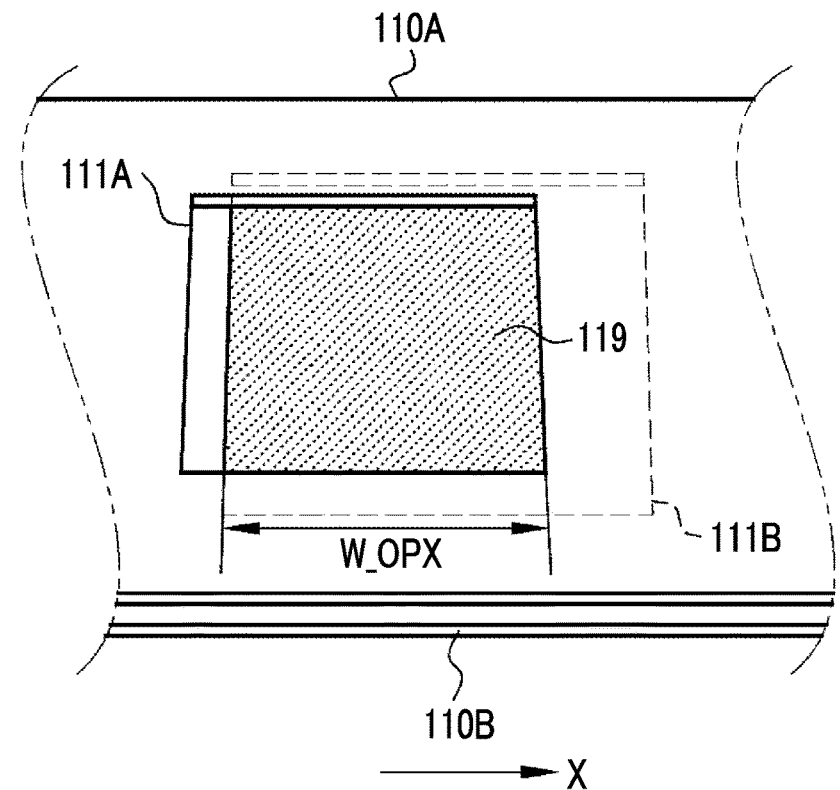
FIGS. 29A and 29B are diagrams illustrating an aspect in which the width of the irradiation opening in the X direction is adjusted.
Figure 29B:
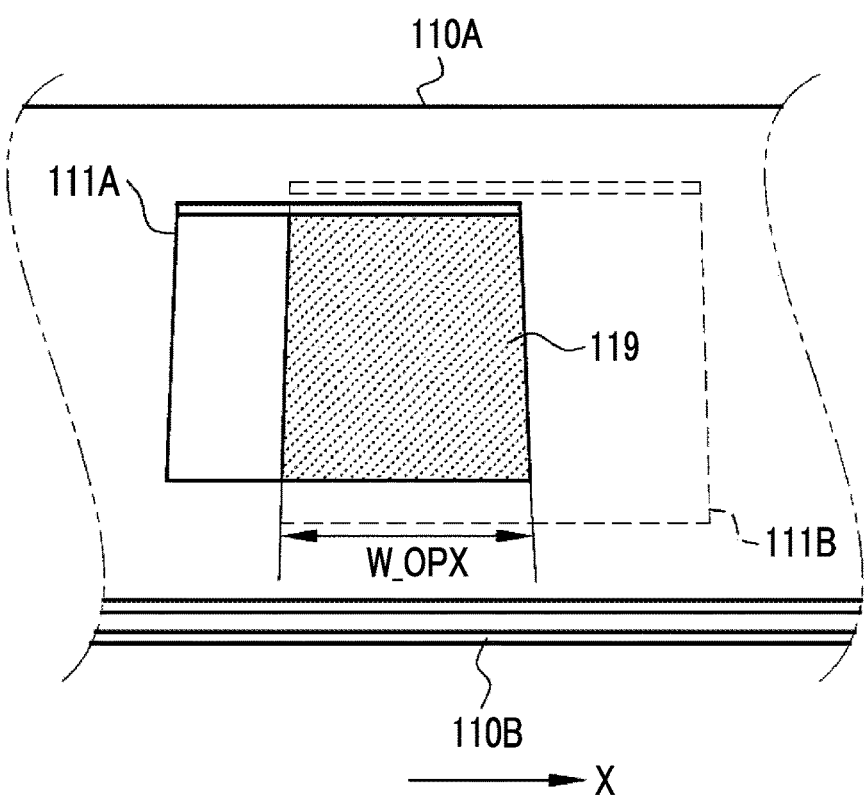

As illustrated in FIGS. 29A and 29B, in the irradiation field limiter according to this embodiment, the amount of movement of the plate-like members 110A and 110B in the X direction is finely adjusted to adjust the width W_OPX of the irradiation opening 119 in the X direction. FIG. 29A illustrates a case in which the width W_OPX of the irradiation opening 119 in the X direction is slightly increased from the state illustrated in FIG. 28 and FIG. 29B illustrates a case in which the width W_OPX of the irradiation opening 119 in the X direction is slightly decreased from the state illustrated in FIG. 28.

As such, in the fourth embodiment, the irradiation field limiter is used in which the plate-like members 110A and 110B having the through holes 111A and 111B, at least one side of which functions as the opening edge of the irradiation opening 119, are stacked in the Z direction that is a direction normal to the imaging surface 45 of the radiation detector 26. The displacement mechanism moves each of the plate-like members 110A and 110B in the X direction which is the arrangement direction of the radiation tubes 27 to move the irradiation openings 119. Therefore, as illustrated in FIGS. 29A and 29B, it is possible to adjust the width W_OPX of the irradiation opening 119 in the X direction.

Further, as illustrated in FIG. 27, the two plate-like members 110A and 110B which are adjacent to each other in the stacking direction are moved at the same time by the motor 117 in the X direction which is the arrangement direction of the radiation tubes 27. Therefore, it is possible to contribute to reducing a component cost and reducing the size of the apparatus, as compared to a case in which the plate-like members 110A and 110B are moved by two motors.

The number of plate-like members stacked is not limited to two. For example, as illustrated in FIG. 30, an irradiation field limiter having a configuration in which four plate-like members 120A, 120B, 120C, and 120D are stacked in the Z direction may be used.

Figure 30:
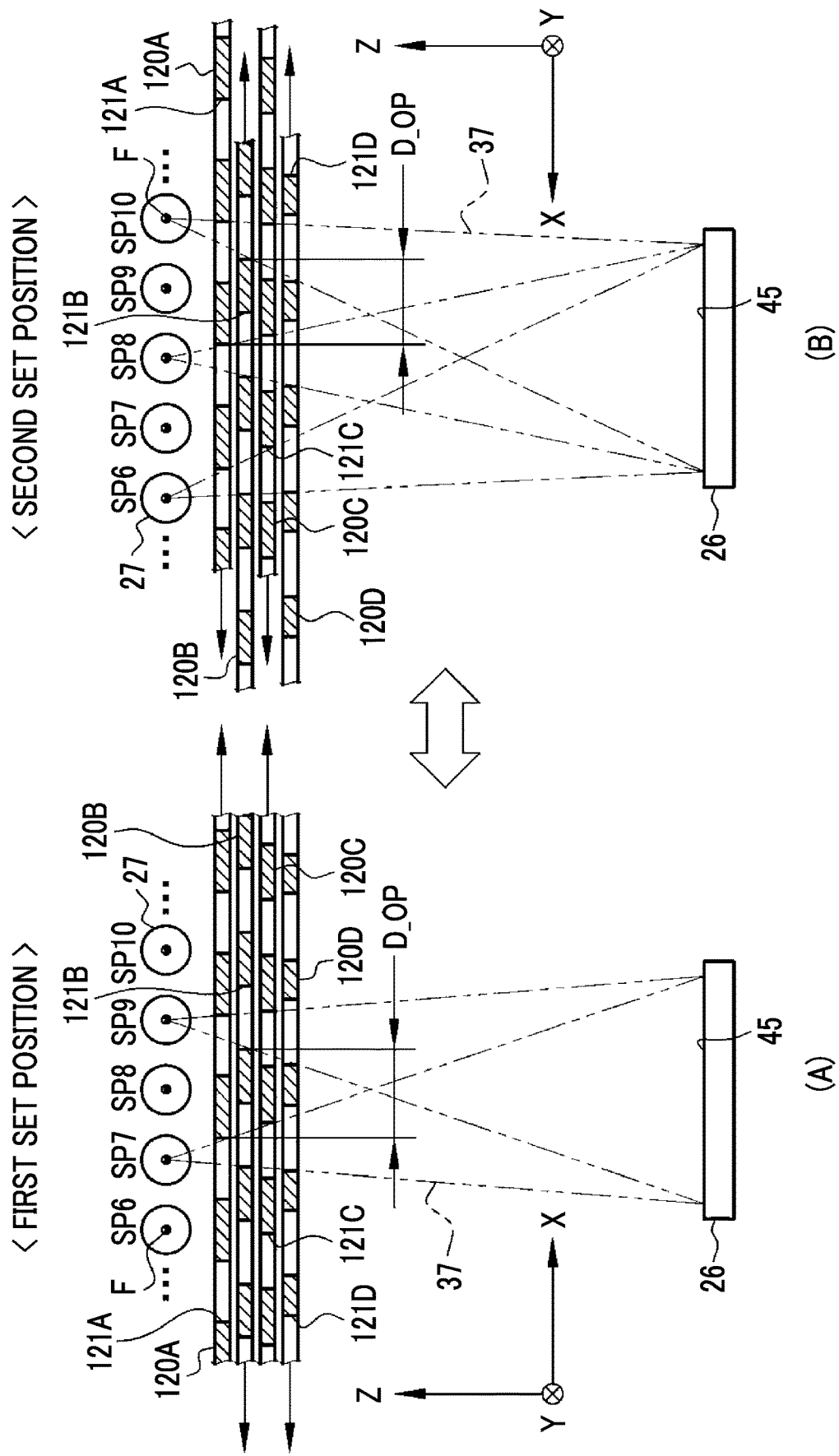
FIG. 30 is a diagram illustrating a modification example of the fourth embodiment using an irradiation field limiter having a configuration in which four plate-like members are stacked. (A) of FIG. 30 illustrates a first set position and (B) of FIG. 30 illustrates a second set position.

In FIG. 30, through holes 121A, 121B, 121C, and 121D are formed in the plate-like members 120A to 120D along the X direction, respectively. As illustrated in (A) of FIG. 30, at the first set position, the through holes 121A to 121D of the plate-like members 120A to 120D function as irradiation openings for the radiation 37 emitted from the radiation tubes 27 disposed at the positions SP1, SP3, SP5, SP7, SP9, SP11, SP13, and SP15. In contrast, as illustrated in (B) of FIG. 30, at the second set position, the through holes 121A to 121D of the plate-like members 120A to 120D function as irradiation openings for the radiation 37 emitted from the radiation tubes 27 disposed at the positions SP2, SP4, SP6, SP8, SP10, SP12, and SP14. In this case, the interval D_OP between the irradiation openings 119 defined by the through holes 121A to 121D is an interval of at least one radiation tube 27.

Further, two plate-like members 120A and 120B that are adjacent to each other in the stacking direction are reciprocated in opposite directions in the X direction by one actuator, as in the irradiation field limiter illustrated in FIG. 26. Similarly, two plate-like members 120C and 120D that are adjacent to each other in the stacking direction are reciprocated in opposite directions in the X direction by one actuator. Further, as in the irradiation field limiter illustrated in FIG. 26, at least one side of each of the through holes 121A to 121D functions as an opening edge of the irradiation opening 119.

As such, in a case in which the four plate-like members 120A to 120D are used, the width W_OPX of the irradiation opening 119 in the X direction can be adjusted more finely than that in a case in which two plate-like members 110A and 110B are used.

The third embodiment may be applied such that a convex portion protruding toward the radiation tube 27 is provided between adjacent through holes of a plate-like member closest to the radiation tube 27 among a plurality of plate-like members.

Fifth Embodiment

Figure 31:
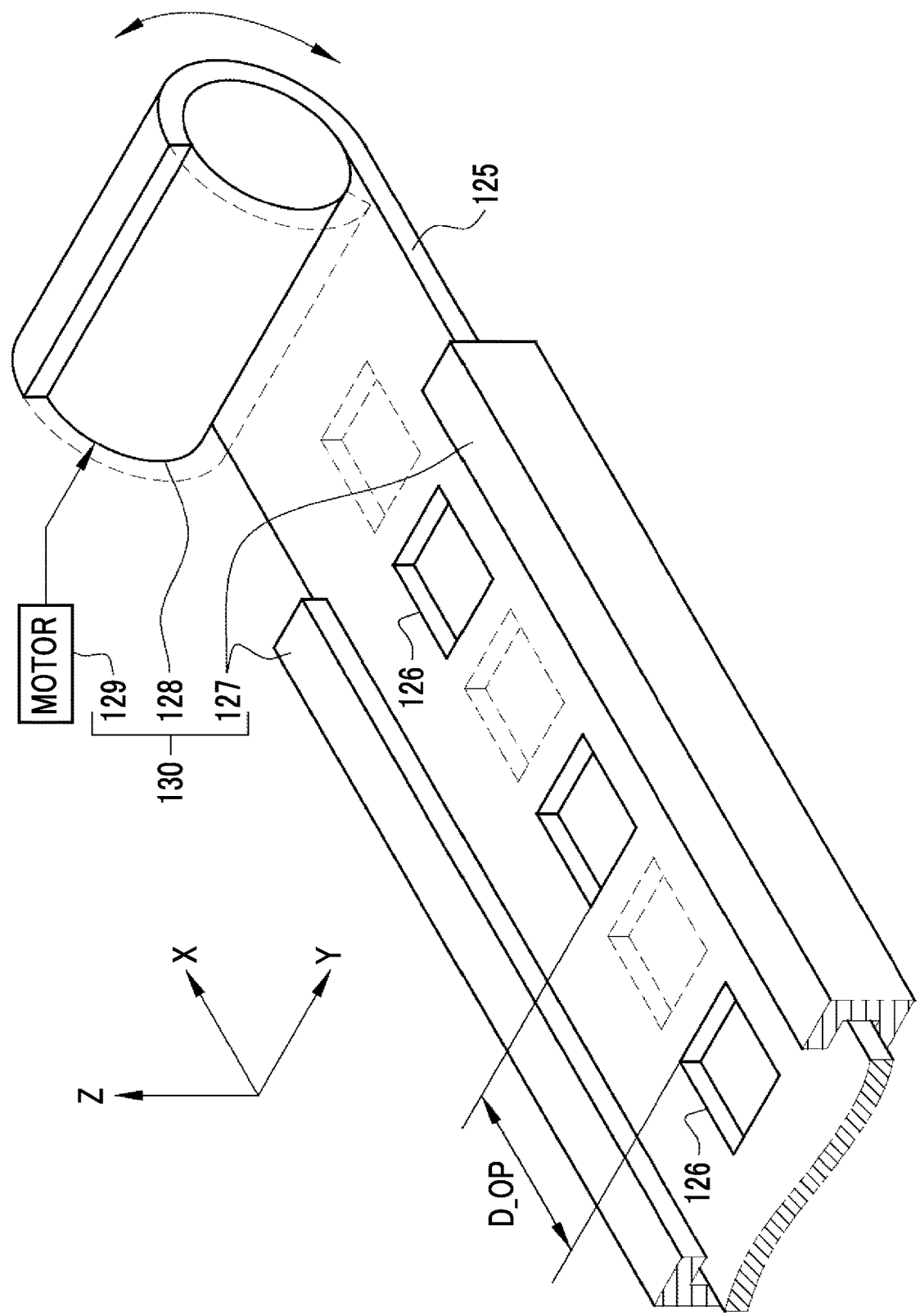
FIG. 31 is a diagram illustrating a fifth embodiment using an irradiation field limiter including a sheet-like member.
Figure 32:
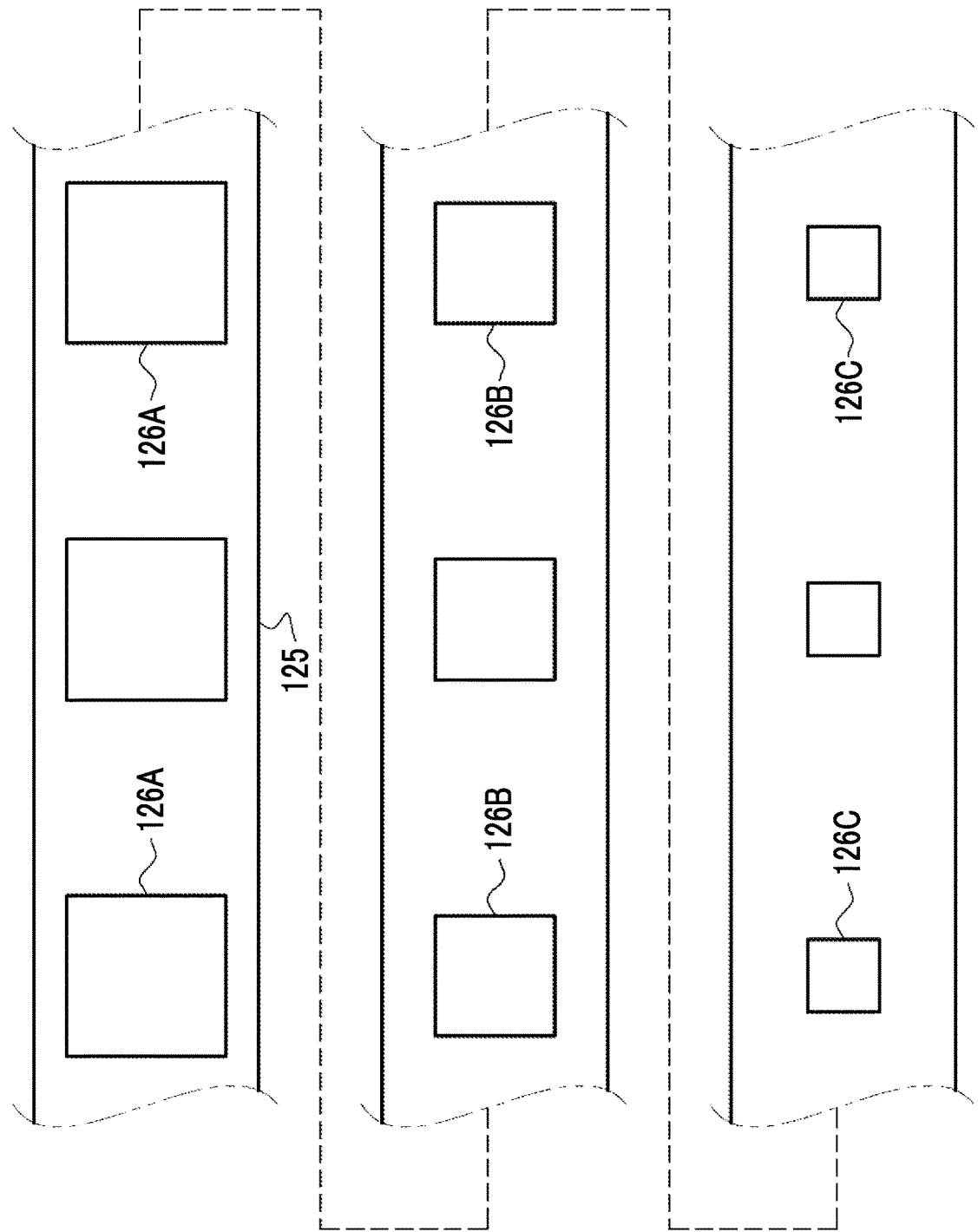
FIG. 32 is a diagram illustrating a plurality of types of through holes.

In a fifth embodiment illustrated in FIGS. 31 and 32, an irradiation field limiter including a sheet-like member is used.

In FIG. 31, through holes 126 that function as irradiation openings are formed in a sheet-like member 125. Adjacent through holes 126 are arranged at an interval D_OP corresponding to at least one radiation tube 27, similarly to the through holes 55 of the plate-like member 52 according to the first embodiment. That is, it can be said that the sheet-like member 125 replaces the plate-like member 52 according to the first embodiment. The sheet-like member 125 is held by a pair of rails 127 so as to be movable in the X direction. For example, the sheet-like member 125 is formed by applying a material for shielding the radiation 37 onto a surface of a flexible plastic film.

One end of the sheet-like member 125 in the X direction is attached to a core 128. The core 128 is rotated clockwise and counterclockwise by a motor 129. The sheet-like member 125 is sent along the X direction and is rolled by the rotation of the core 128 by the motor 129. Therefore, as represented by a dashed line, the through holes 126 that function as the irradiation openings are moved. That is, the rails 127, the core 128, and the motor 129 form a displacement mechanism 130. A space for accommodating the sent sheet-like member 125 is ensured at the other end of the sheet-like member 125 in the X direction, which is not illustrated.

As illustrated in FIG. 32, there are three types of through holes 126, that is, a through hole 126A with a relatively large size, a through hole 126B with a medium size, and a through hole 126C with a relatively small size. A control unit according to the fifth embodiment changes the amount of sending of the sheet-like member 125 such that any one of the through holes 126A to 126C faces each radiation tube 27.

As such, in the fifth embodiment, the irradiation field limiter including the sheet-like member 125 in which the through holes 126 functioning as the irradiation openings are formed is used. Then, the displacement mechanism 130 sends the sheet-like member 125 in the X direction which is the arrangement direction of the radiation tubes 27 and rolls the sheet-like member 125 to move the irradiation openings.

Therefore, the weight of the irradiation field limiter can be less than the weight of the irradiation field limiter including the plate-like member.

Further, a plurality of types of through holes 126A to 126C having different sizes are formed in the sheet-like member 125. Therefore, it is possible to change the size of the irradiation field. It is possible to significantly reduce the number of components as compared to a case in which a plurality of plate-like members having a plurality of types of through holes with different sizes are prepared and are selectively used. In addition, it is possible to contribute to reducing the size of the apparatus.

The number of types of the through holes 126 may be two or four or more. Further, a core may be attached to the other end of the sheet-like member 125 in the X direction and may be rotated by a motor.

The number of types of the through holes 126 may be one. In this case, the second embodiment may be applied to move the sheet-like member 125 in the direction in which the interval between the radiation tube 27 and the through hole 126 changes. Alternatively, the fourth embodiment may be applied to stack a plurality of sheet-like members 125 in the Z direction.

Sixth Embodiment

Figure 34:
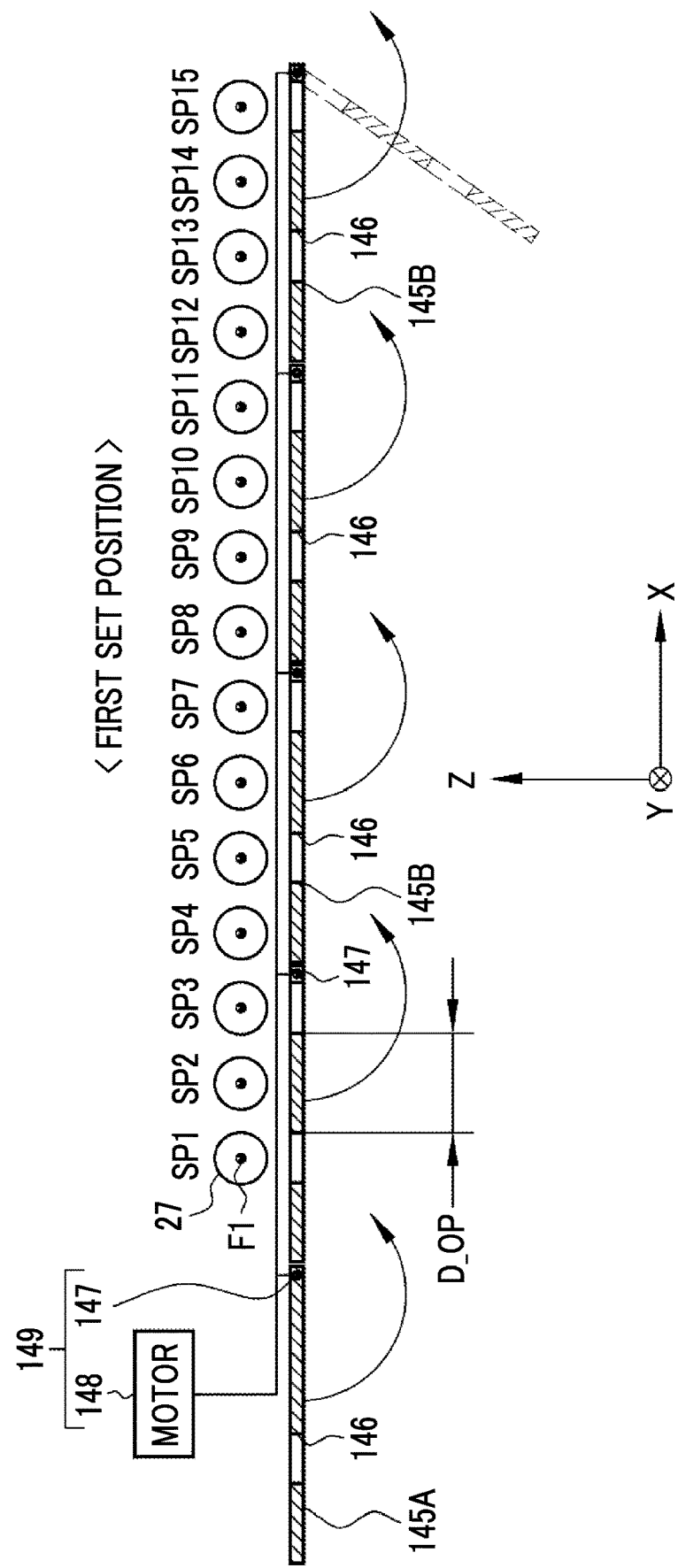
FIG. 34 is a diagram illustrating a modification example of the sixth embodiment in which the plate-like members are rotated to move the irradiation openings.
Figure 35:
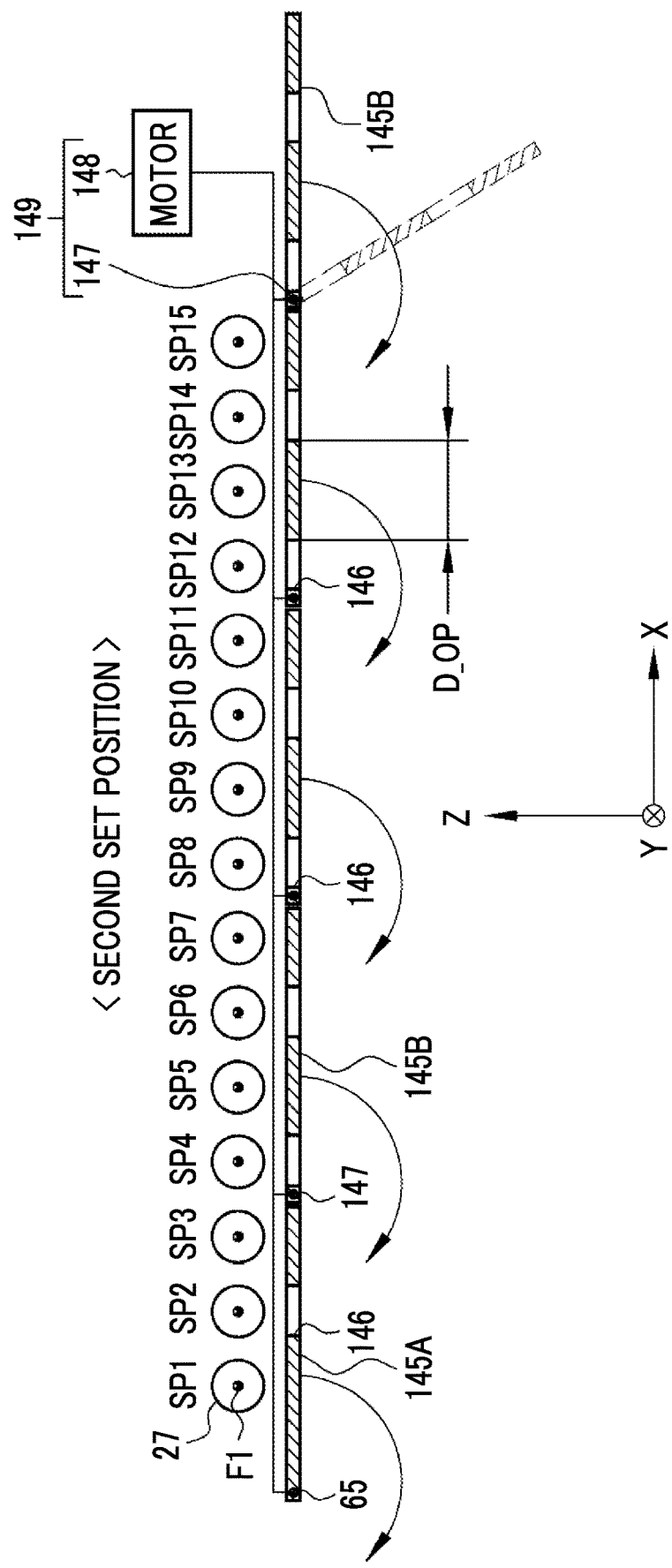
FIG. 35 is a diagram illustrating a modification example of the sixth embodiment in which the plate-like members are rotated to move the irradiation openings.

In a sixth embodiment illustrated in FIGS. 33 to 35, a plate-like member is rotated to move irradiation openings.

An irradiation field limiter illustrated in FIG. 33 includes eight plate-like members 135 that are arranged in the X direction (only five plate-like members 135 are illustrated in FIG. 33). Each of the plate-like members 135 has one through hole 136 that functions as the irradiation opening. A rotating shaft 137 is attached to each plate-like member 135. The rotating shaft 137 is disposed between the radiation tube 27 and the imaging surface 45. Specifically, the rotating shaft 137 is a shaft extending in a direction that is orthogonal to the X direction which is the arrangement direction of the radiation tubes 27 and is parallel to the imaging surface 45 of the radiation detector 26. That is, the rotating shaft 137 is parallel to the Y direction.

A motor 138 is connected to the rotating shafts 137. The rotating shafts 137 are rotated clockwise and counterclockwise by the motor 138. Each plate-like member 135 is rotated clockwise and counterclockwise about the rotating shaft 137. The rotating shafts 137 and the motor 138 form a displacement mechanism 139.

As illustrated in (A) of FIG. 33, at the first set position, the through holes 136 of the plate-like member 135 function as irradiation openings for the radiation 37 emitted from the radiation tubes 27 disposed at the positions SP1, SP3, SP5, SP7, SP9, SP11, SP13, and SP15. In contrast, as illustrated in (B) of FIG. 33, at the second set position, the through holes 136 of the plate-like member 135 function as irradiation openings for the radiation 37 emitted from the radiation tubes 27 disposed at the positions SP2, SP4, SP6, SP8, SP10, SP12, and SP14. However, the through hole 136 corresponding to the radiation tube 27 at the position SP1 at the first set position is excluded. In this case, the interval D_OP between the irradiation openings defined by the through holes 136 is an interval of at least one radiation tube 27.

As such, in the sixth embodiment, the irradiation field limiter including the plate-like members 135 in which the through hole 136 functioning as the irradiation opening is formed is used. Then, the plate-like member 135 is rotated about the rotating shaft 137 extending in a direction that is orthogonal to the X direction which is the arrangement direction of the radiation tubes 27 and is parallel to the imaging surface 45 of the radiation detector 26 to move the irradiation opening. Therefore, it is possible to respond to a case in which it is difficult to adopt each of the above-described embodiments in which the plate-like member or the sheet-like member is moved in the X direction for some reason.

The number of through holes formed in the plate-like member is not limited to one. For example, two through holes 146 may be formed, as in a plate-like member 145 illustrated in FIGS. 34 and 35.

In FIGS. 34 and 35, the plate-like member 145 includes one first plate-like member 145A that is disposed close to the position SP1 and four second plate-like members 145B. One through hole 146 that functions as the irradiation opening is formed in the first plate-like member 145A. In contrast, two through holes 146 that function as the irradiation openings are formed in the second plate-like member 145B. Rotating shafts 147 are attached to the first plate-like member 145A and the second plate-like members 145B. Similarly to the rotating shaft 137, the rotating shaft 147 is a shaft extending in a direction that is orthogonal to the X direction which is the arrangement direction of the radiation tubes 27 and is parallel to the imaging surface 45 of the radiation detector 26.

A motor 148 is connected to the rotating shafts 147. The rotating shafts 147 are rotated clockwise and counterclockwise by the motor 148. The first plate-like member 145A and the second plate-like members 145B are rotated clockwise and counterclockwise about the rotating shafts 147. The rotating shafts 147 and the motor 148 form a displacement mechanism 149.

As illustrated in FIG. 34, at the first set position, the through holes 146 of the second plate-like member 145B function as irradiation openings for the radiation 37 emitted from the radiation tubes 27 disposed at the positions SP1, SP3, SP5, SP7, SP9, SP11, SP13, and SP15. In contrast, as illustrated in FIG. 35, at the second set position, the through holes 146 of the first plate-like member 145A and the second plate-like member 145B function as irradiation openings for the radiation 37 emitted from the radiation tubes 27 disposed at the positions SP2, SP4, SP6, SP8, SP10, SP12, and SP14. However, the through holes 146 of the second plate-like member 145B corresponding to the radiation tubes 27 at the position SP13 and SP15 at the first set position are excluded. In this case, the interval D_OP between the irradiation openings defined by the through holes 146 is an interval of at least one radiation tube 27.

Seventh Embodiment

Figure 36:
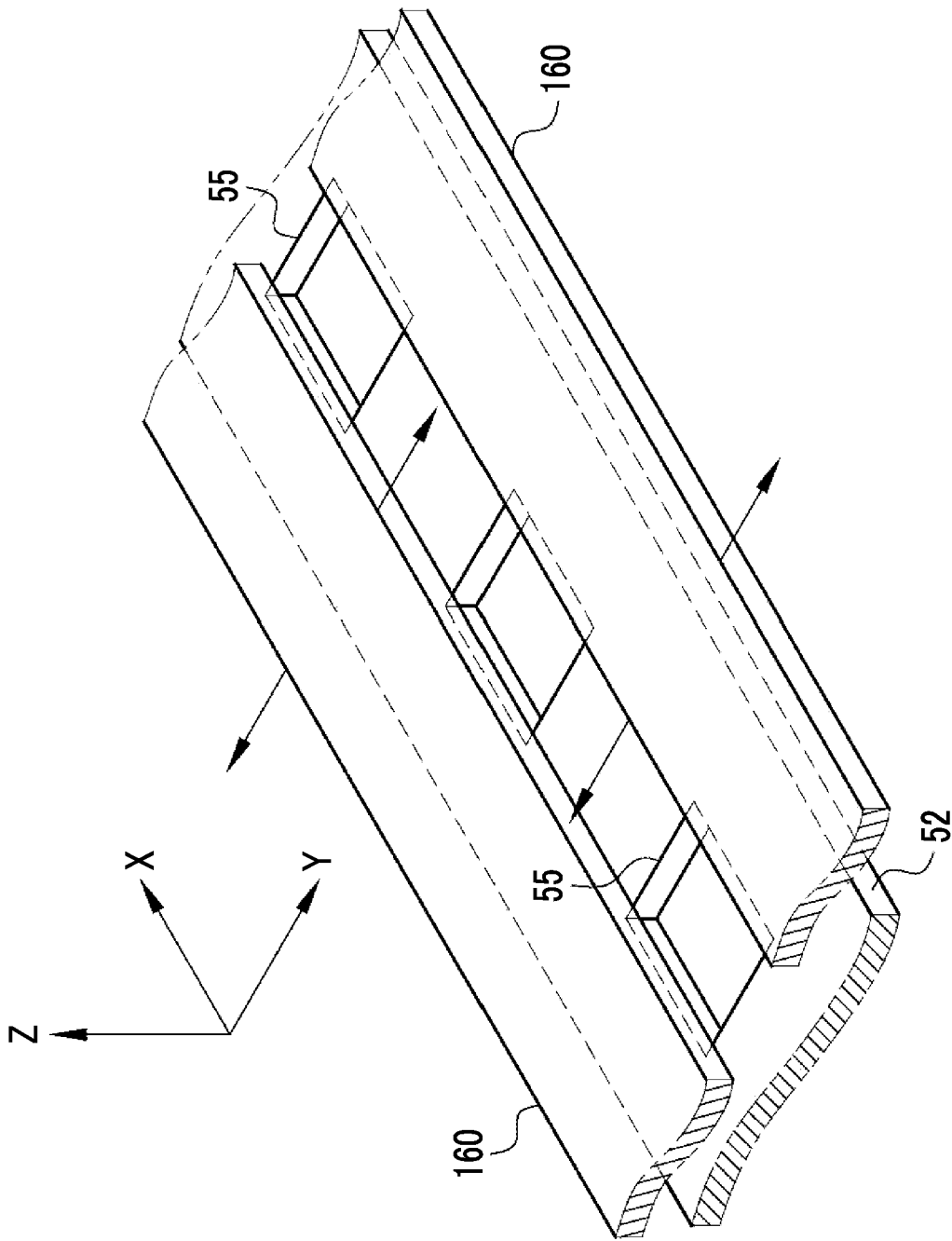
FIG. 36 is a perspective view illustrating a seventh embodiment in which the width of an irradiation opening in the Y direction is adjusted.
Figure 37:
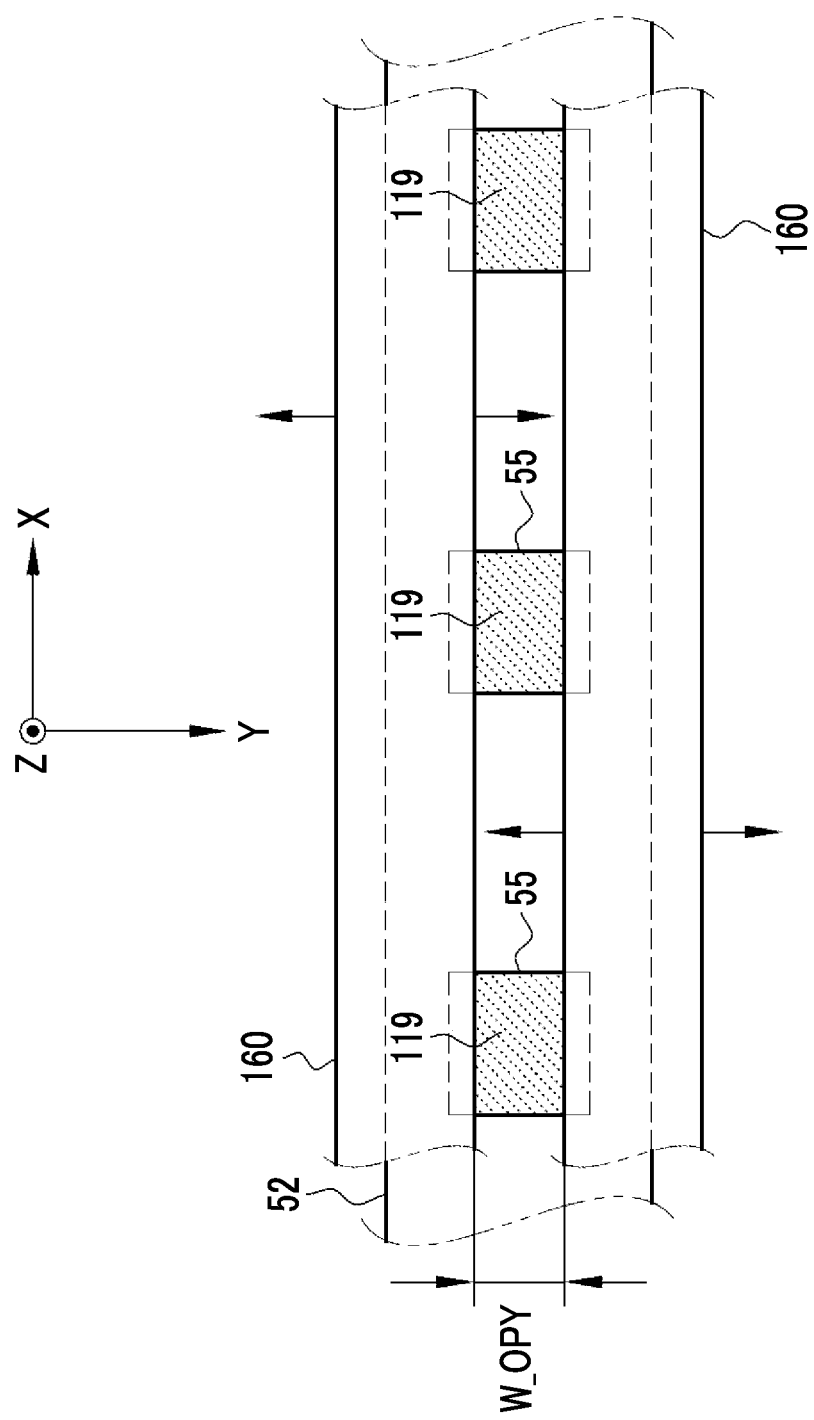
FIG. 37 is a plan view illustrating the seventh embodiment in which the width of the irradiation opening in the Y direction is adjusted.

In a seventh embodiment illustrated in FIGS. 36 and 37, adjustment members 160 adjust the widths of a plurality of irradiation openings 119 at once.

FIGS. 36 and 37 illustrate a case in which the plate-like member 52 according to the first embodiment is used. In FIGS. 36 and 37, a pair of adjustment members 160 are disposed above the plate-like member 52 so as to cover the plate-like member 52. The adjustment member 160 is a rectangular plate that is long in the X direction and has long sides arranged along the X direction. The adjustment members 160 can be reciprocated in the Y direction by a movement mechanism (not illustrated). The Y direction is an example of "a direction intersecting the arrangement direction of the radiation tubes" according to the technique of the present disclosure. As illustrated in FIG. 37, the adjustment members 160 are moved in the Y direction to adjust the widths W_OPY of the plurality of irradiation openings 119 in the Y direction at once.

As such, in the seventh embodiment, the adjustment members 160 for adjusting the widths W_OPY of the plurality of irradiation openings 119 are provided. The adjustment members 160 are moved in the direction intersecting the arrangement direction of the radiation tubes 27 to adjust the widths W_OPY of the plurality of irradiation openings 119 at once. Therefore, it is possible to easily adjust the widths W_OPY of the irradiation openings 119 in the Y direction.

The application of the seventh embodiment is not limited to the irradiation field limiter 29 including the plate-like member 52 according to the first embodiment, but the seventh embodiment may be applied to the irradiation field limiters according to other embodiments to adjust the widths W_OPY of the irradiation openings 119 in the Y direction.

A pair of plate-like members 165 and 166 illustrated in FIGS. 38 to 41 may be used.

Figure 38:
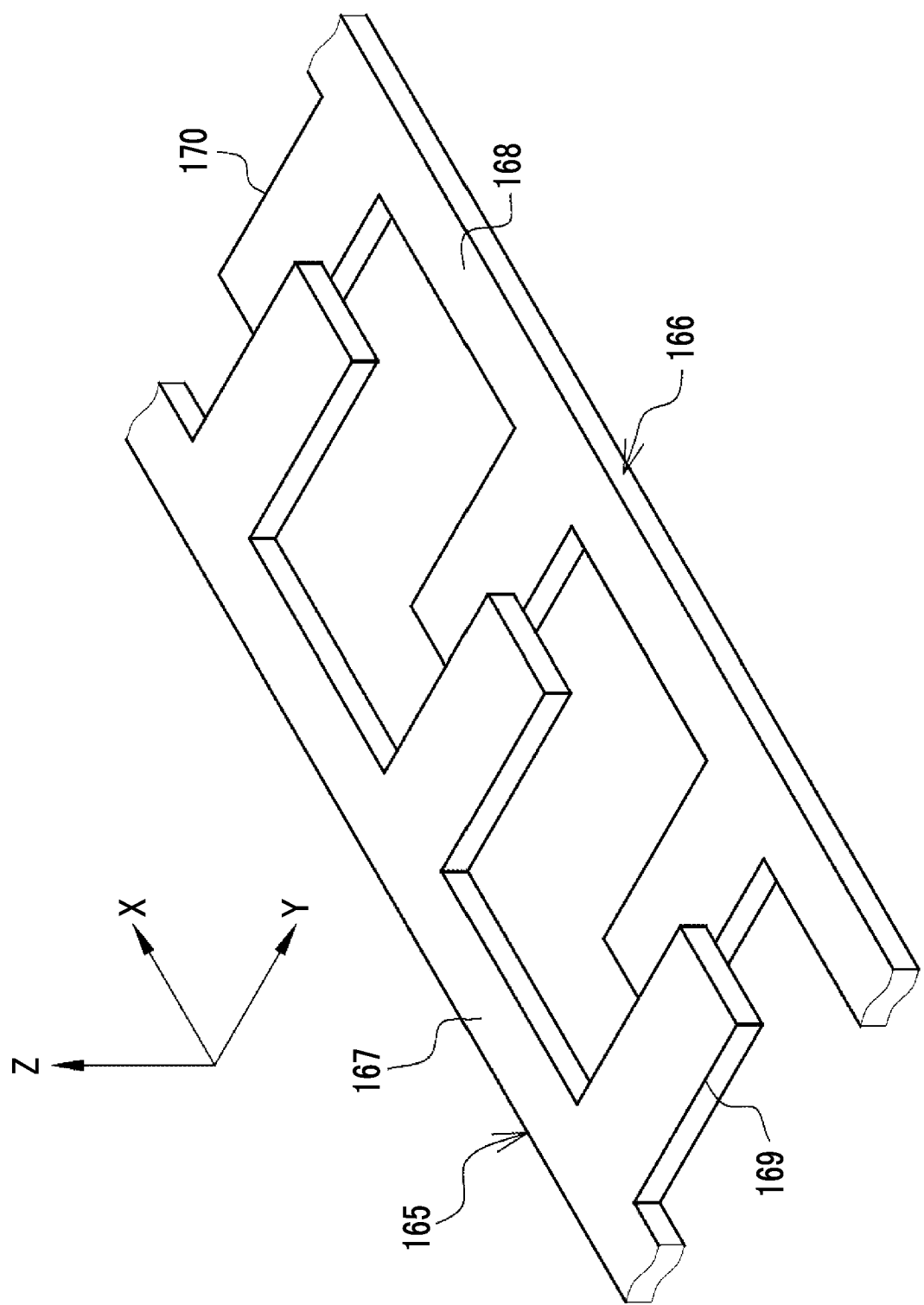
FIG. 38 is a diagram illustrating a modification example of the plate-like member.

In FIG. 38, the pair of plate-like members 165 and 166 are line-symmetric with respect to the X direction. The plate-like members 165 and 166 have a shape obtained by cutting the plate-like member 52 of the first embodiment in zigzag. Specifically, the plate-like members 165 and 166 have a comb shape in which a plurality of rectangular plate-like protruding portions 169 and 170 protrude from long portions 167 and 168 that are long in the X direction in the Y direction at intervals, respectively. The plate-like members 165 and 166 are disposed so as to deviate from each other in the Z direction (see also FIGS. 41 and 42). The plate-like members 165 and 166 are moved obliquely upward or downward (see FIGS. 41 and 42).

Figure 39:
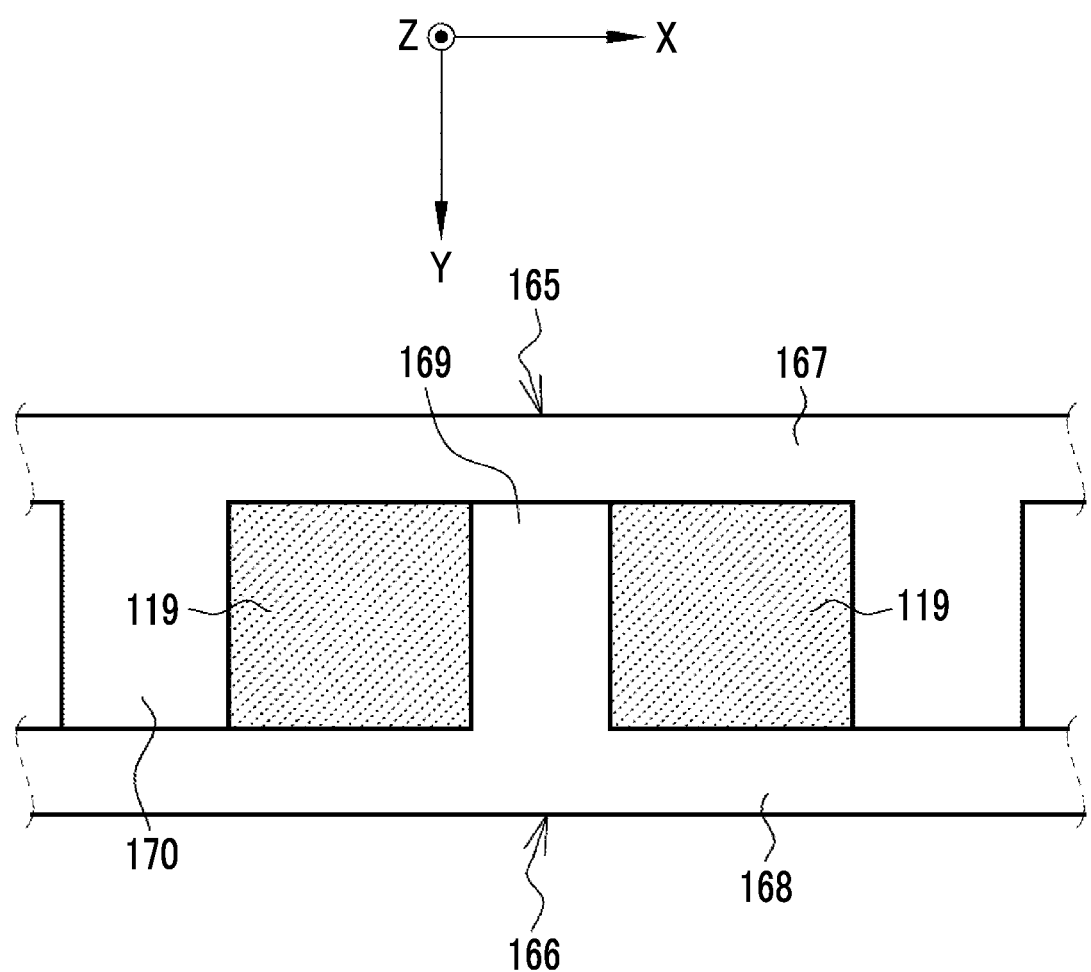
FIG. 39 is a diagram illustrating an aspect in which the irradiation opening is defined by the plate-like member illustrated in FIG. 38.

In this case, as illustrated in FIG. 39, the irradiation opening 119 is defined by a space surrounded by the long portion 167 and the protruding portion 169 of the plate-like member 165 and the long portion 168 and the protruding portion 170 of the plate-like member 166.

Figure 40:
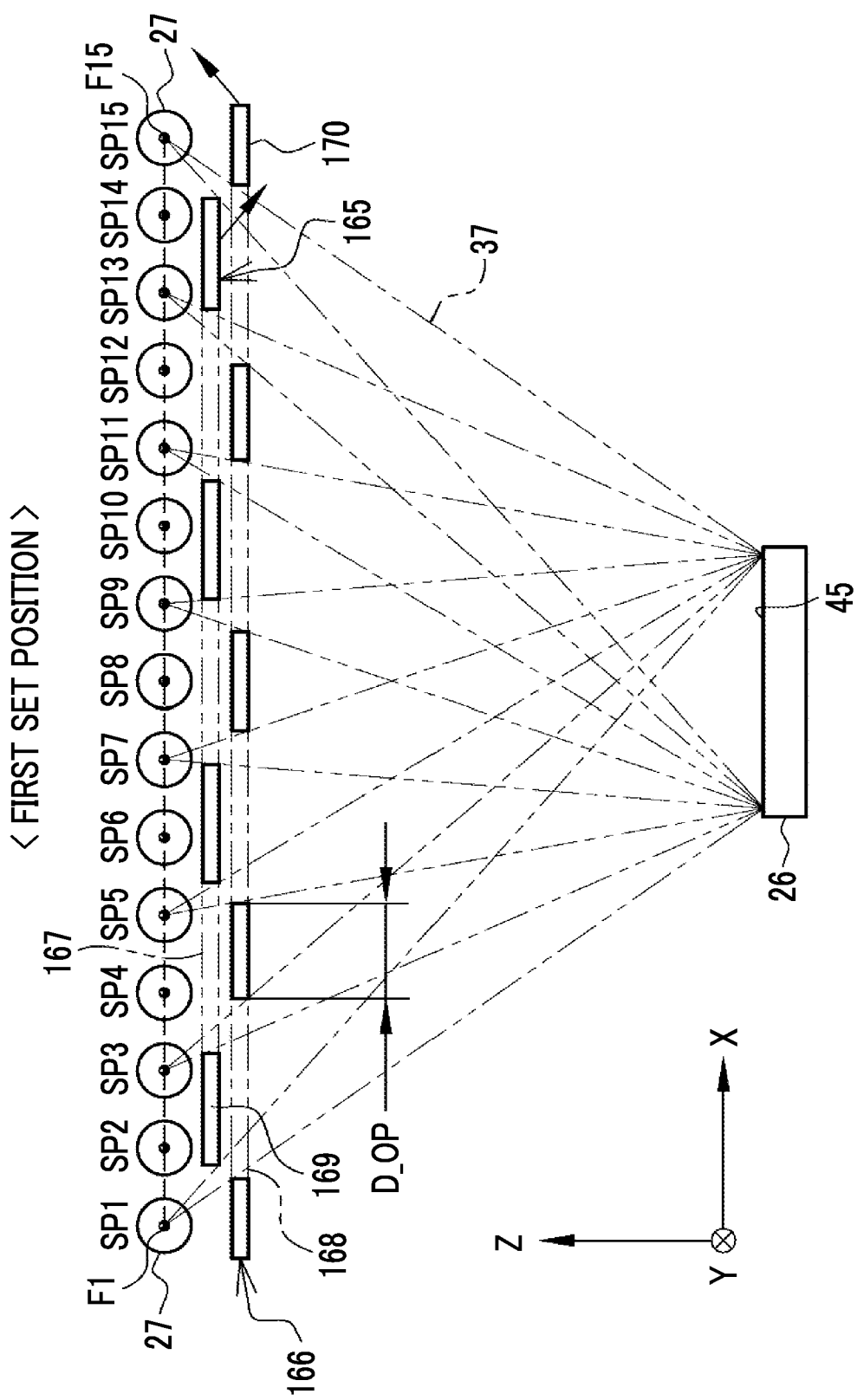
FIG. 40 is a diagram illustrating a first set position of the plate-like member illustrated in FIG. 38.
Figure 41:
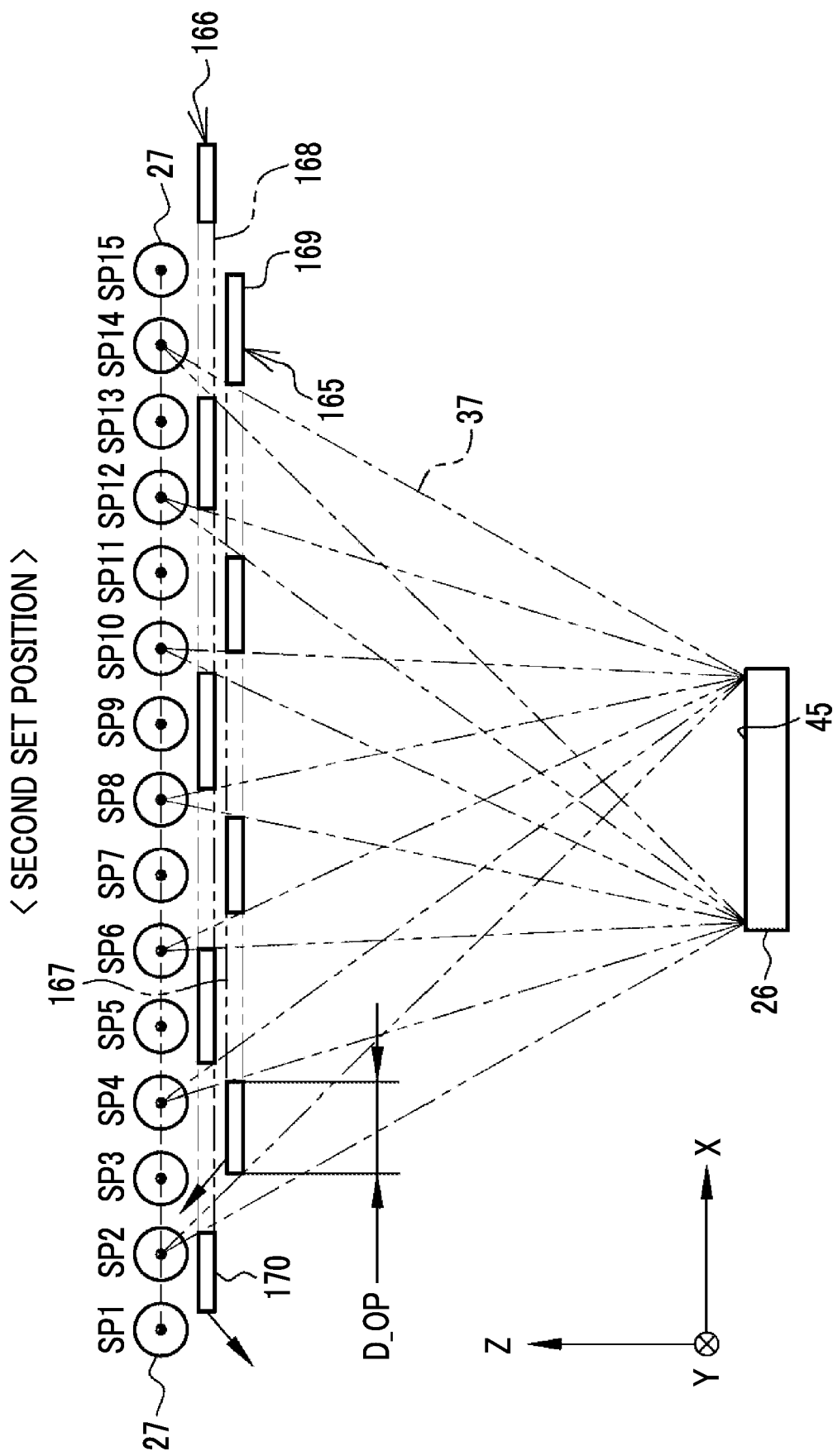
FIG. 41 is a diagram illustrating a second set position of the plate-like member illustrated in FIG. 38.

As illustrated in FIG. 40, at the first set position, the long portions 167 and 168 and the protruding portions 169 and 170 of the plate-like members 165 and 166 function as irradiation openings for the radiation 37 emitted from the radiation tubes 27 disposed at the positions SP1, SP3, SP5, SP7, SP9, SP11, SP13, and SP15. In contrast, as illustrated in FIG. 41, at the second set position, the long portions 167 and 168 and the protruding portions 169 and 170 of the plate-like members 165 and 166 function as irradiation openings for the radiation 37 emitted from the radiation tubes 27 disposed at the positions SP2, SP4, SP6, SP8, SP10, SP12, and SP14. In this case, the interval D_OP between the irradiation openings 119 is an interval of at least one radiation tube 27.

At the first set position, the plate-like member 165 is disposed on the side of the radiation tubes 27 and the plate-like member 166 is disposed on the side of the radiation detector 26. At the second set position, the plate-like member 165 is moved obliquely downward from the first set position and the plate-like member 166 is moved obliquely upward from the first set position. Then, contrary to the first set position, the plate-like member 166 is disposed on the side of the radiation tubes 27 and the plate-like member 165 is disposed on the side of the radiation detector 26. In FIGS. 40 and 41, the protruding portions 169 and 170 are represented by solid lines and the long portions 167 and 168 are represented by two-dot chain lines for ease of understanding.

As such, the plate-like members 165 and 166 without having through holes are used and the irradiation openings 119 can be defined by moving the plate-like members 165 and 166 in an oblique direction. Two plate-like members 165 and 166 are illustrated in FIGS. 38 to 41. However, the number of plate-like members may be three or more.

Figure 42:
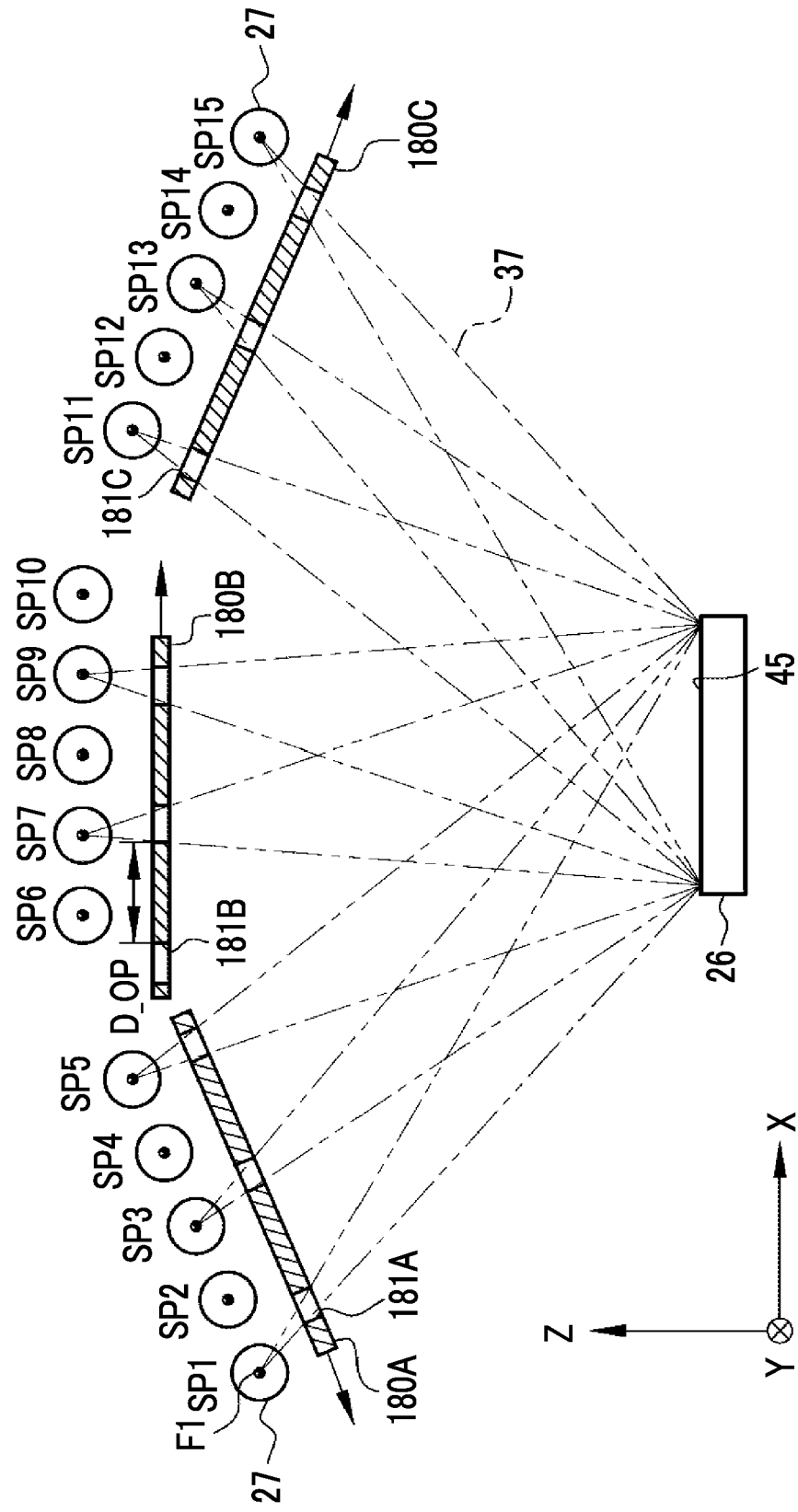
FIG. 42 is a diagram illustrating an example in which a plurality of radiation tubes are divided into a plurality of groups and radiation tubes in the groups at the ends are arranged so as to be inclined at a predetermined angle with respect to an imaging surface.
Figure 43:
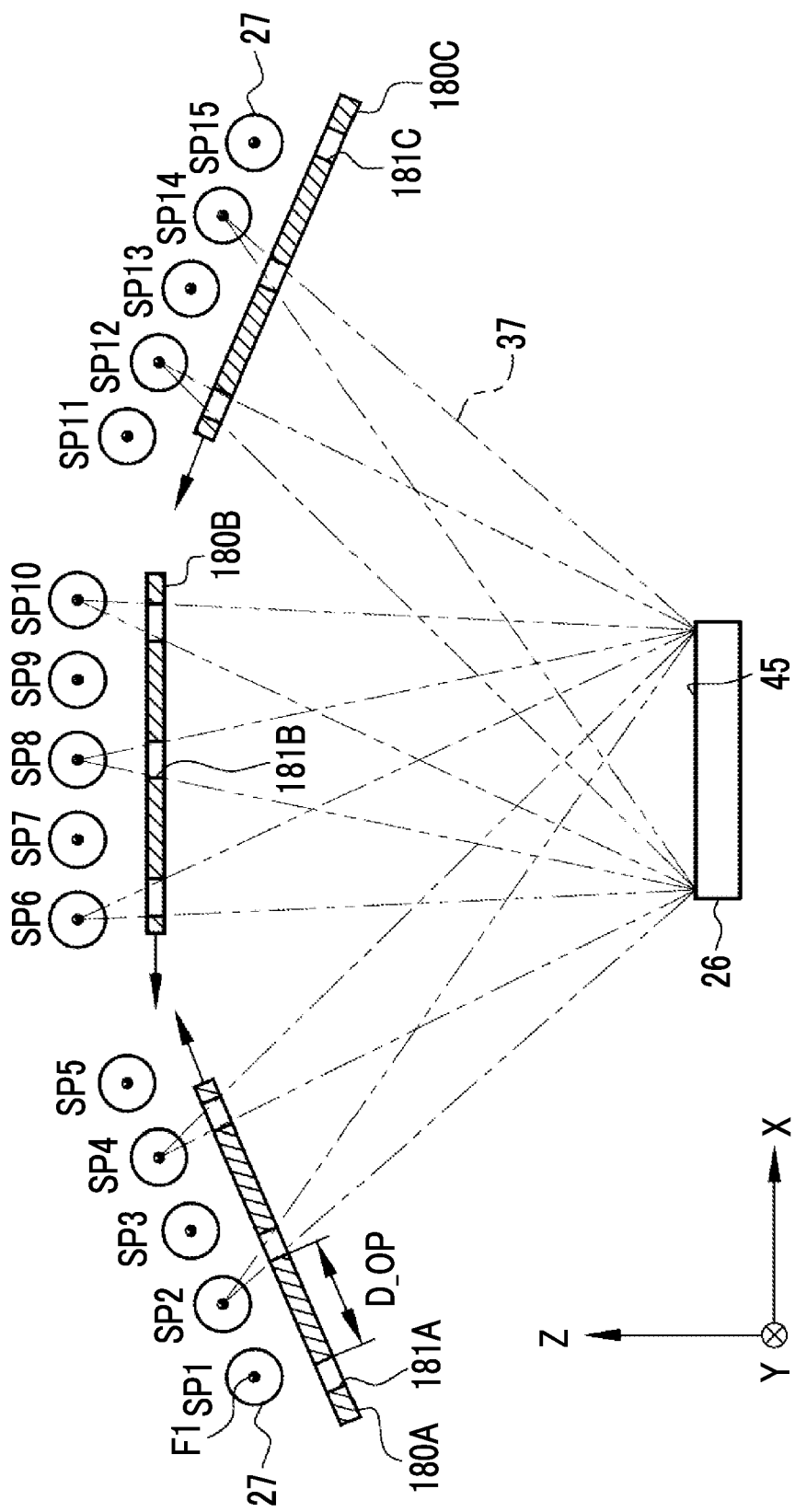
FIG. 43 is a diagram illustrating an example in which a plurality of radiation tubes are divided into a plurality of groups and radiation tubes in the groups at the ends are arranged so as to be inclined at a predetermined angle with respect to the imaging surface.

As illustrated in FIGS. 42 and 43, the radiation tubes 27 may be divided into a first group of the radiation tubes 27 disposed at the positions SP1 to SP5, a second group of the radiation tubes 27 disposed at the positions SP6 to SP10, and a third group of the radiation tubes 27 disposed at the positions SP11 to SP15. The radiation tubes 27 in the first group and the third group may be arranged so as to be inclined at a predetermined angle with respect to the imaging surface 45.

In this case, it is preferable to prepare plate-like members 180 for each group. That is, a plate-like member 180A is prepared for the first group, a plate-like member 180B is prepared for the second group, and a plate-like member 180C is prepared for the third group. A through hole 181A is formed in the plate-like member 180A, a through hole 181B is formed in the plate-like member 180B, and a through hole 181C is formed in the plate-like member 180C.

The plate-like members 180A to 180C are moved to a first set position illustrated in FIG. 42 and a second set position illustrated in FIG. 43. As illustrated in FIG. 42, at the first set position, the through holes 181A to 181C of the plate-like members 180A to 180C function as irradiation openings for the radiation 37 emitted from the radiation tubes 27 disposed at the positions SP1, SP3, SP5, SP7, SP9, SP11, SP13, and SP15. In contrast, as illustrated in FIG. 43, at the second set position, the through holes 181A to 181C of the plate-like members 180A to 180C function as irradiation openings for the radiation 37 emitted from the radiation tubes 27 disposed at the positions SP2, SP4, SP6, SP8, SP10, SP12, and SP14. In this case, the interval D_OP between the irradiation openings defined by the through holes 181A to 181C is an interval of at least one radiation tube 27.

Figure 44:
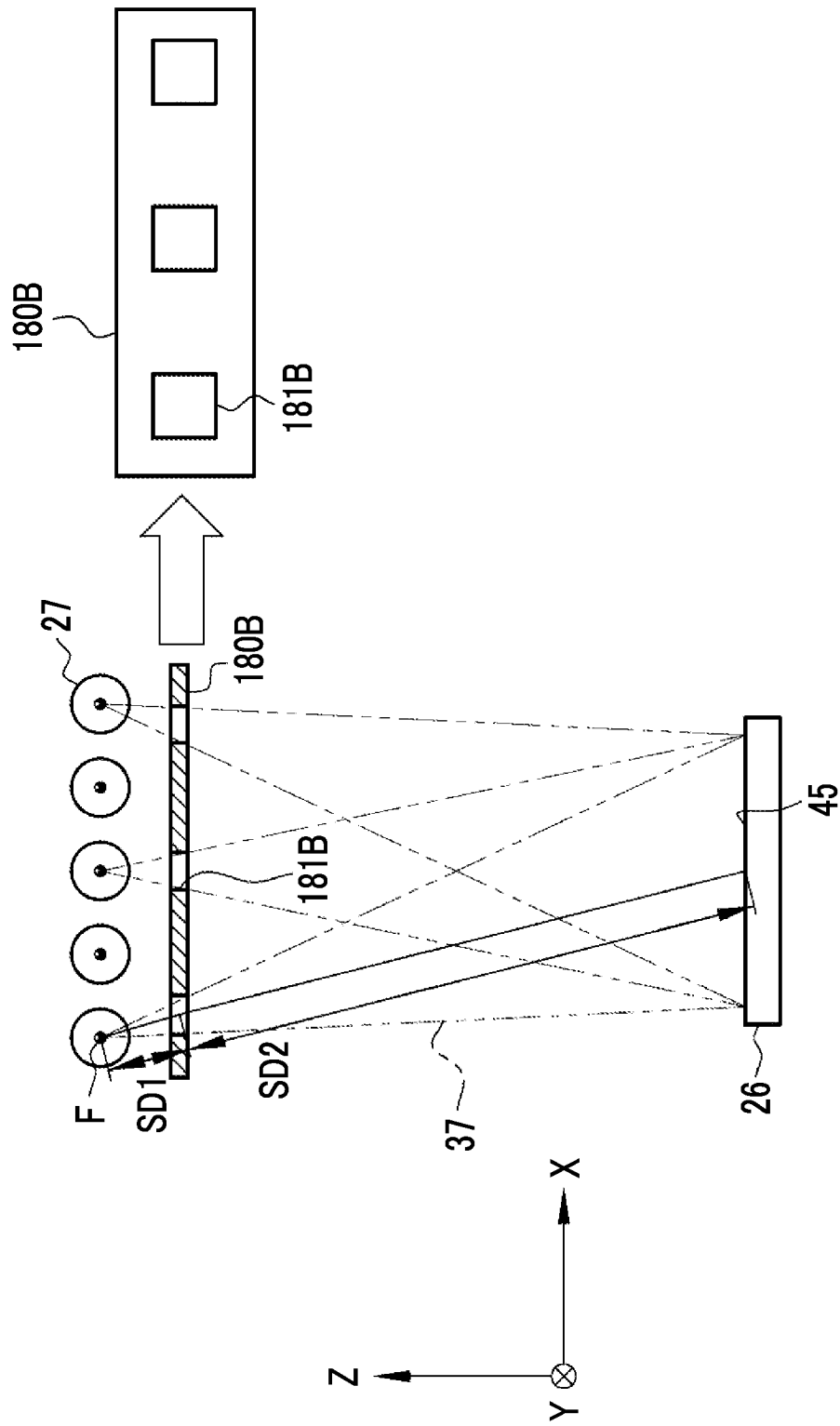
FIG. 44 is a diagram illustrating the size and shape of through holes of a plate-like member in a second group.

As illustrated in FIG. 44, in the second group, a ratio SD1/SD2 of a distance SD1 between the radiation tube 27 and the plate-like member 180B to a distance SD2 between the plate-like member 180B and the imaging surface 45 is the same for all of the radiation tubes 27 forming the group. Further, the arrangement direction of the radiation tubes 27 is parallel to the direction of the long side of the plate-like member 180B. Furthermore, the side of the imaging surface 45 in the X direction is parallel to the direction of the long side of the plate-like member 180B. Therefore, the through holes 181B of the plate-like member 180B have the same size and have a rectangular shape. The distance SD1 is the length of a line connecting the focus F of the radiation tube 27 and the center of the through hole 181B facing the radiation tube 27. The distance SD2 is the length of a line connecting the center of the through hole 181B and the center of the imaging surface 45.

Figure 45:
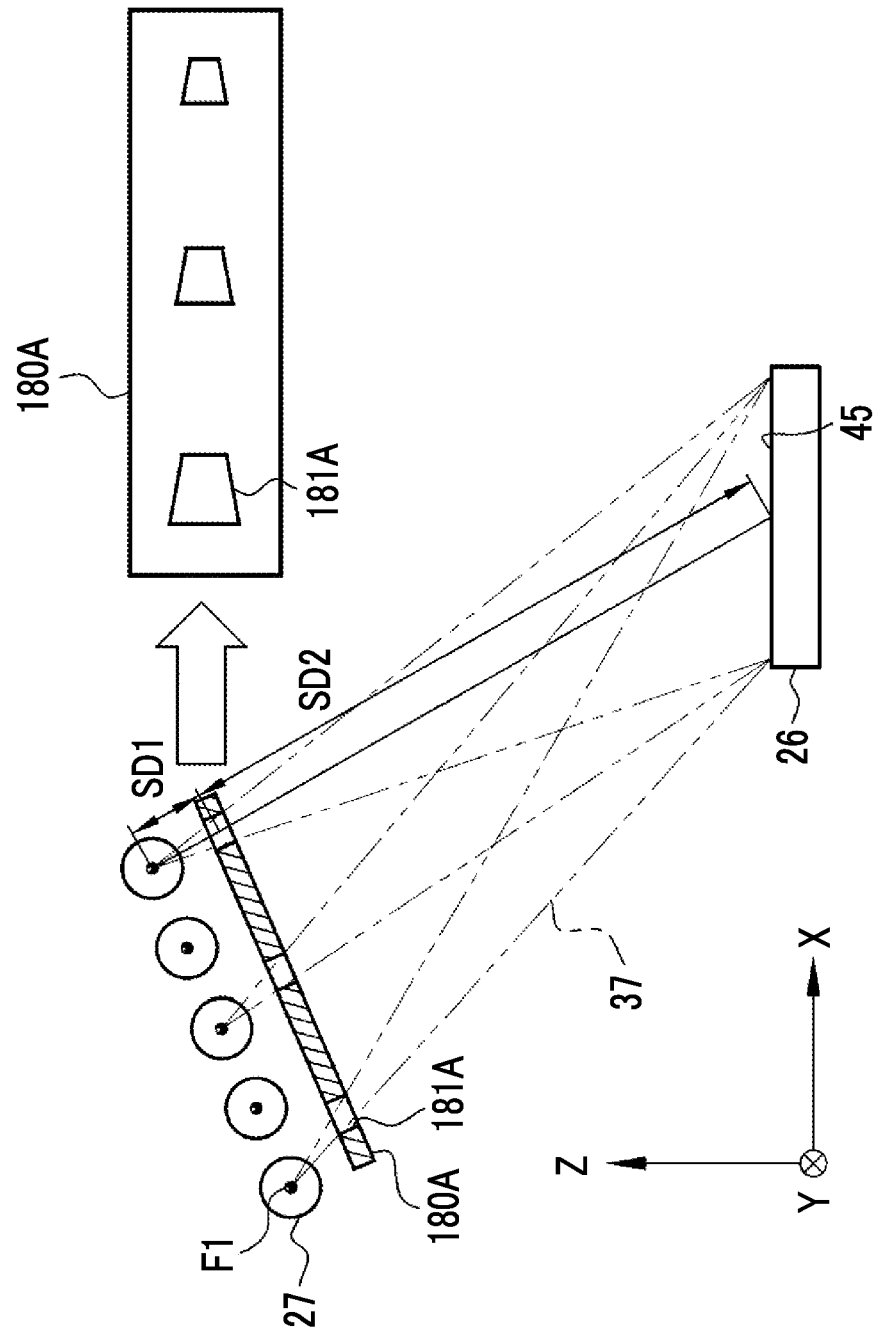
FIG. 45 is a diagram illustrating the size and shape of through holes of a plate-like member in a first group.

In contrast, as illustrated in FIG. 45, the first group is the same as the second group in that the arrangement direction of the radiation tubes 27 is parallel to the direction of the long side of the plate-like member 180A. However, in the first group, the ratio SD1/SD2 varies depending on the radiation tubes 27 forming the group. Further, as described above, since the radiation tubes 27 are arranged so as to be inclined at a predetermined angle with respect to the imaging surface 45, the side of the imaging surface 45 in the X direction is not parallel to the direction of the long side of the plate-like member 180A. Therefore, the through holes 181A of the plate-like member 180A have different sizes. Specifically, the size of the through hole 181A increases toward the end. Further, the through hole 181A has a trapezoidal shape in which the base is widened toward the end. In addition, since the plate-like member 180C is mirror-symmetric to the plate-like member 180A, it is not illustrated.

Figure 46:
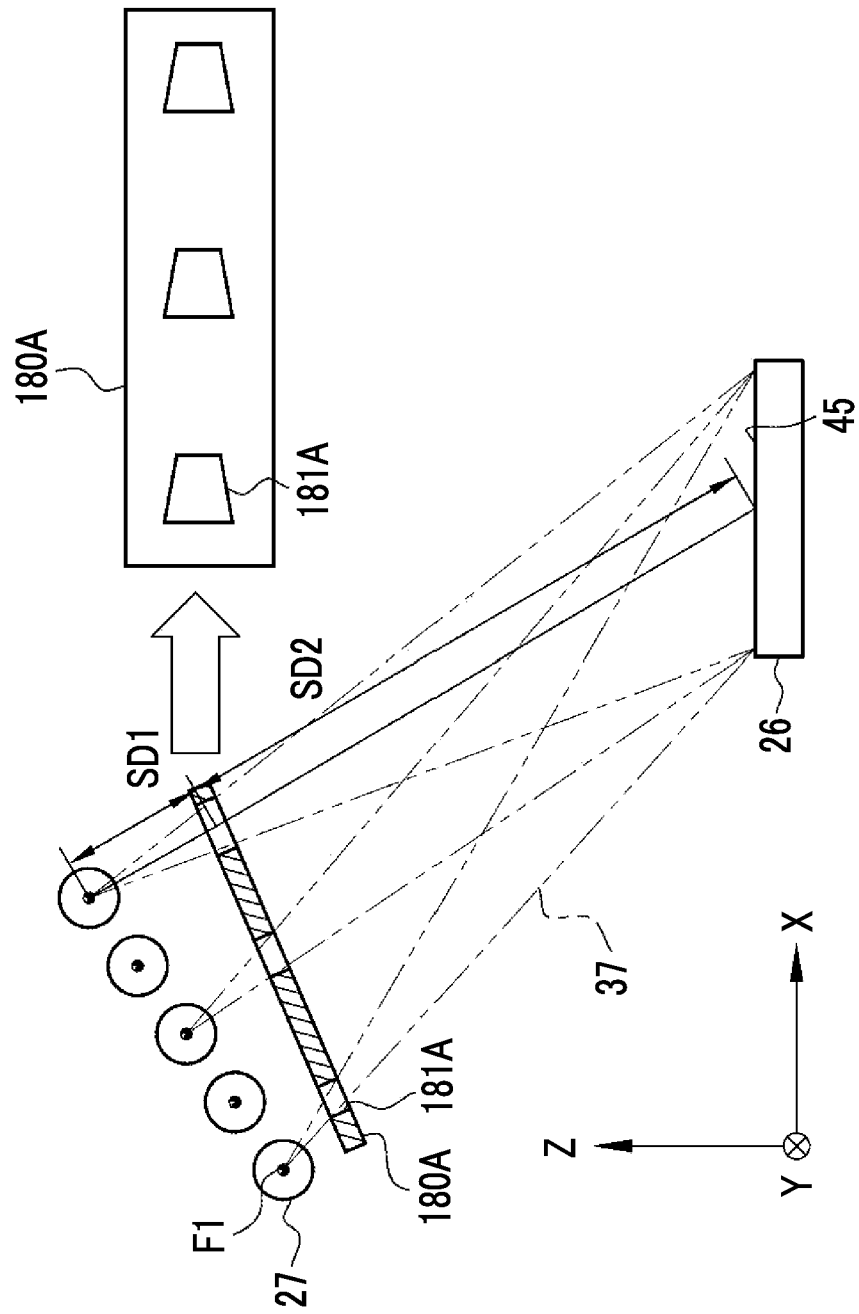
FIG. 46 is a diagram illustrating another example of the size and shape of the through holes of the plate-like member in the first group.

As illustrated in FIG. 46, in the first group, the radiation tubes 27 may be disposed so as to become further away from the plate-like member 180A as becoming closer to the center such that the ratio SD1/SD2 is the same for all of the radiation tubes 27 forming the group. In this case, the through holes 181A have the same trapezoidal shape as those in the case illustrated in FIG. 45 and have the same size. In this case, in the third group, similarly, the radiation tubes 27 are disposed so as to become further away from the plate-like member 180C as becoming closer to the center such that the ratio SD1/SD2 is the same for all of the radiation tubes 27 forming the group, which is not illustrated.

As such, a plurality of radiation tubes 27 may be divided into a plurality of groups, each group may be regarded as one radiation source, and the plate-like members 180A to 180C may be arranged in each group.

Figure 47:
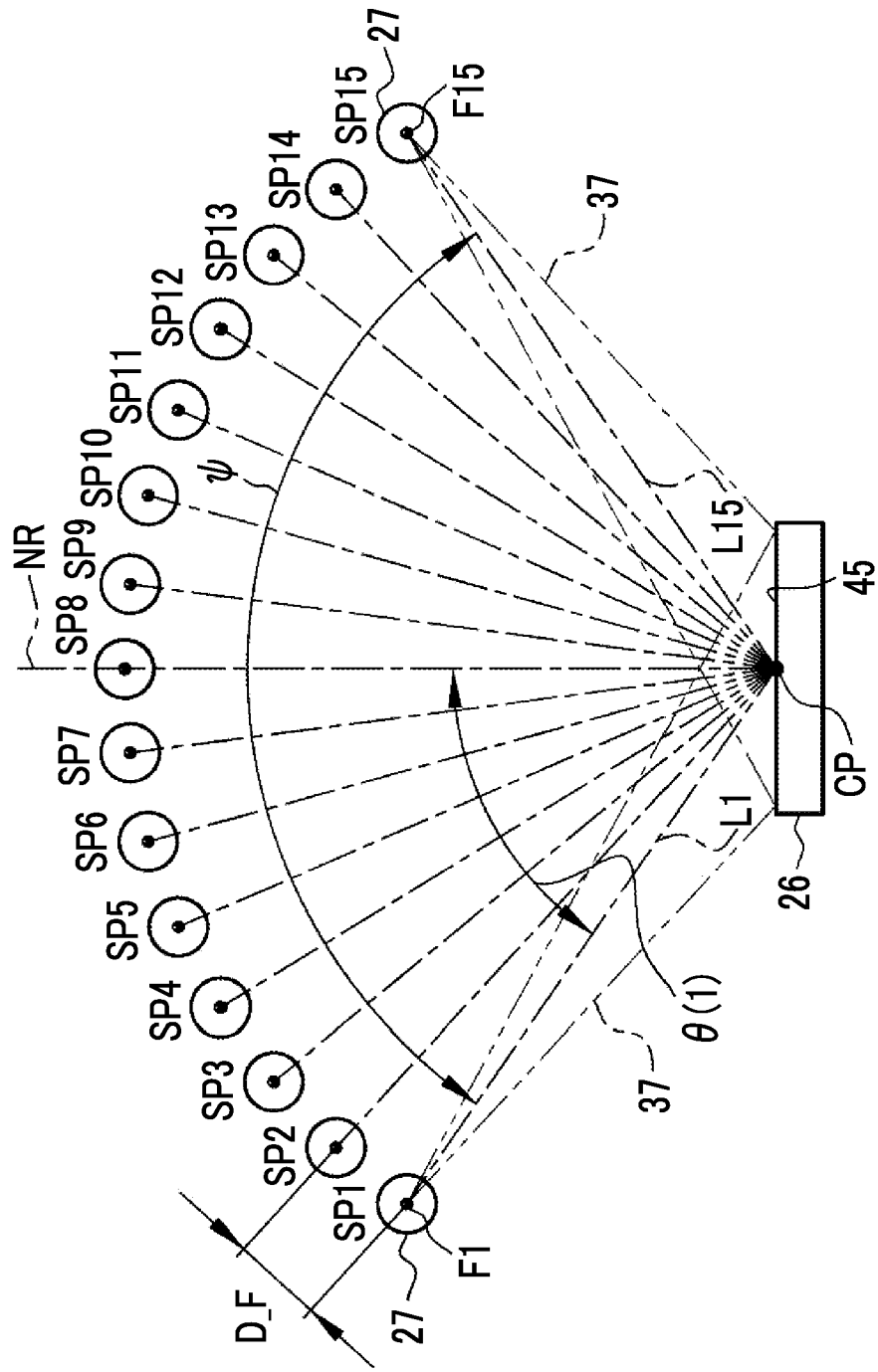
FIG. 47 is a diagram illustrating an example in which the radiation tubes are disposed at a plurality of positions where the focuses of radiation are set so as to be arranged in an arc shape at equal intervals.
Figure 48:
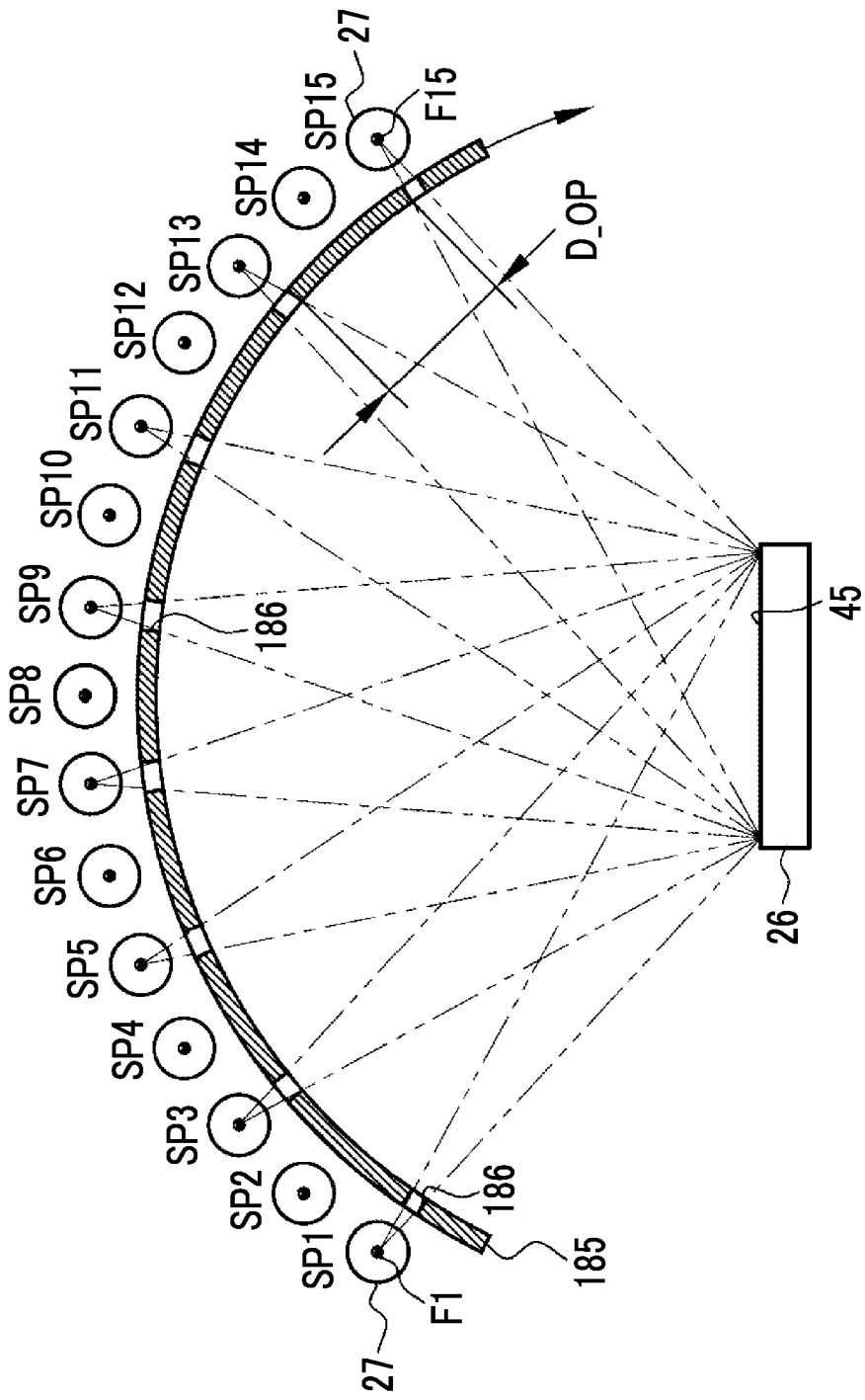
FIG. 48 is a diagram illustrating a first set position of a plate-like member in the example illustrated in FIG. 47.
Figure 49:
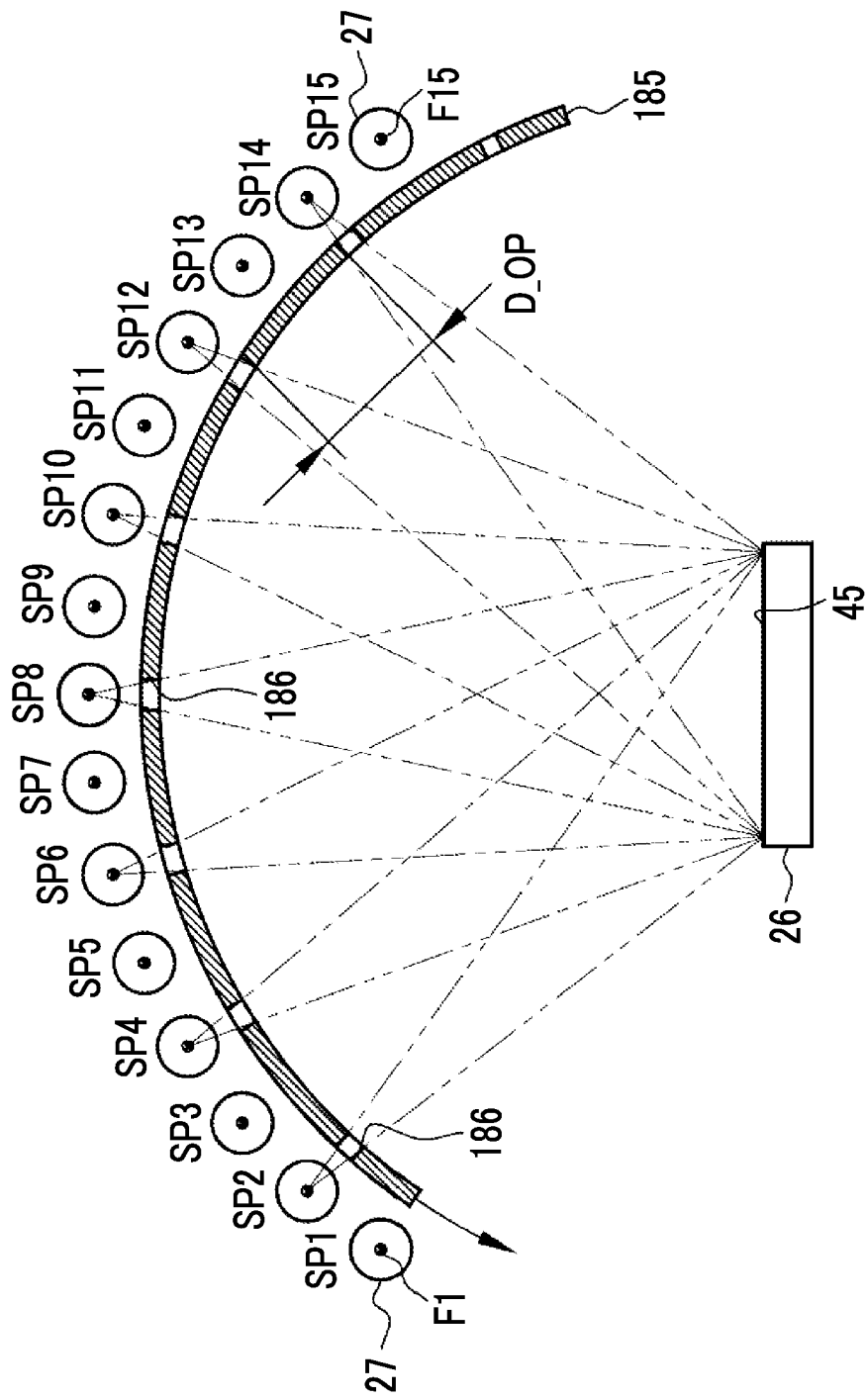
FIG. 49 is a diagram illustrating a second set position of the plate-like member in the example illustrated in FIG. 47.

In each of the above-described embodiments, the positions where the focuses F are disposed are arranged in a straight line. However, the invention is not limited thereto. As illustrated in FIG. 47, the plurality of positions SP1 to SP15 where the focuses F1 to F15 are disposed may be arranged in an arc shape at equal intervals D_F. In this case, for example, one plate-like member 185 illustrated in FIGS. 48 and 49 is used. The plate-like member 185 has an arc shape following the positions SP1 to SP15. Through holes 186 that function as irradiation openings are formed in the plate-like member 185. The plate-like member 185 is moved in the arrangement direction of the radiation tubes 27.

As illustrated in FIG. 48, at the first set position, the through holes 186 of the plate-like member 185 function as irradiation openings for the radiation 37 emitted from the radiation tubes 27 disposed at the positions SP1, SP3, SP5, SP7, SP9, SP11, SP13, and SP15. In contrast, as illustrated in FIG. 49, at the second set position, the through holes 186 of the plate-like member 185 function as irradiation openings for the radiation 37 emitted from the radiation tubes 27 disposed at the positions SP2, SP4, SP6, SP8, SP10, SP12, and SP14. However, the through hole 186 corresponding to the radiation tube 27 at the position SP15 at the first set position is excluded. In this case, the interval D_OP between the irradiation openings defined by the through holes 186 is an interval of at least one radiation tube 27.

Figure 50:
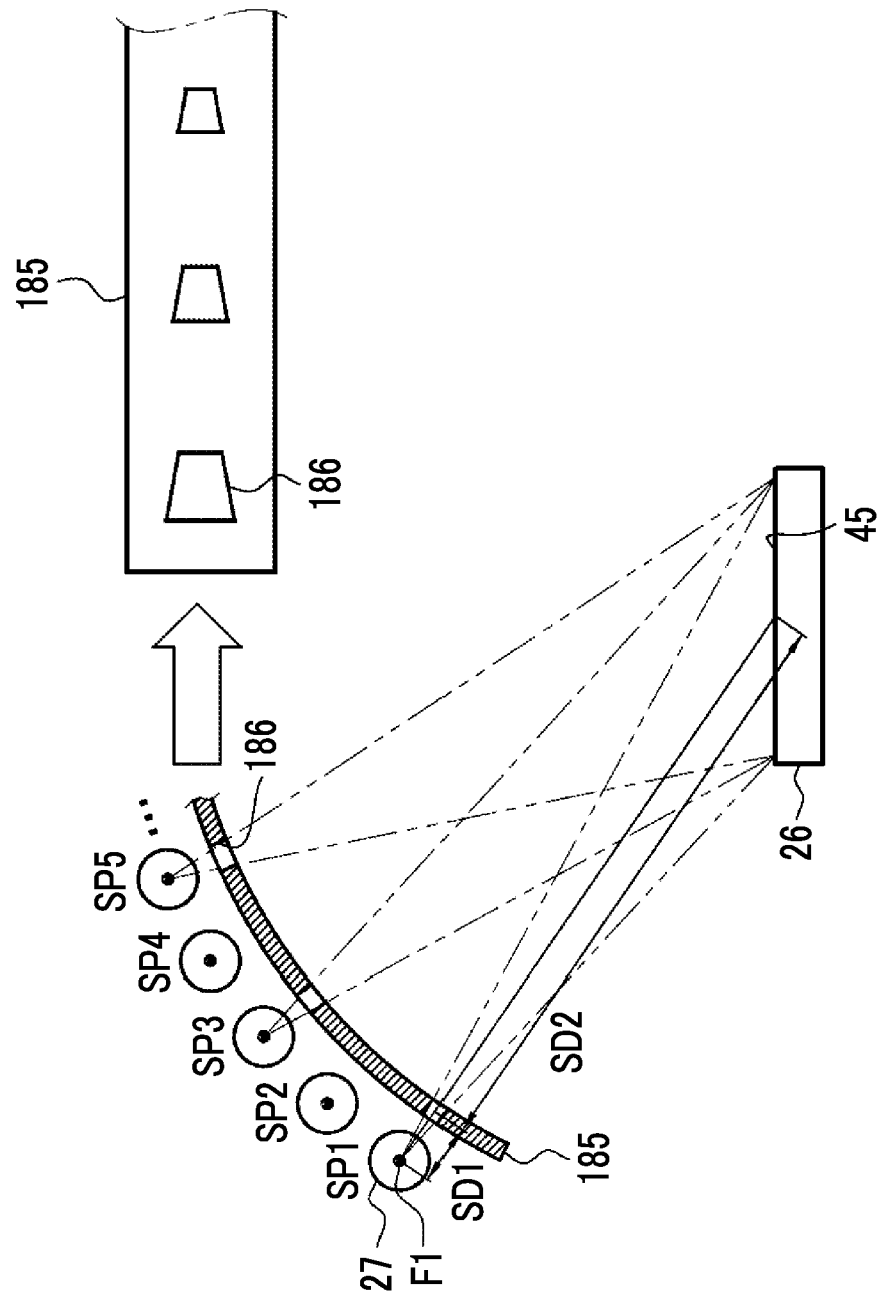
FIG. 50 is a diagram illustrating the size and shape of through holes of the plate-like member in the example illustrated in FIG. 47.

In this case, as illustrated in FIG. 50, the ratio SD1/SD2 varies depending on the radiation tube 27. Further, as described above, since the radiation tubes 27 are arranged in an arc shape, the side of the imaging surface 45 in the X direction is not parallel to the direction of the long side of the plate-like member 185. Therefore, the size of the through hole 186 increases toward the end. Further, the through hole 186 has a trapezoidal shape in which the base is widened toward the end.

As illustrated in FIG. 51, a plate-like member 187 with a linear shape may be used instead of the plate-like member 185 with an arc shape. In this case, the ratio SD1/SD2 varies depending on the radiation tube 27. However, the side of the imaging surface 45 in the X-direction is parallel to the direction of the long side of the plate-like member 187. Therefore, the size of the through hole 188 of the plate-like member 187 decreases toward the end. The shape of the through hole 188 is the same as a rectangular shape.

FIG. 52 is a table 189 summarizing the sizes and shapes of the through holes in the aspects illustrated in FIGS. 42 to 51. Patterns 1 to 3 indicate cases in which the radiation tubes 27 are arranged in a linear shape and patterns 4 and 5 indicate cases in which the radiation tubes 27 are arranged in an arc shape. Pattern 1 indicates an aspect of the plate-like member 180B illustrated in FIG. 44. In this case, the through holes 181B have the same size and have the same rectangular shape. Pattern 2 indicates an aspect of the plate-like member 180A illustrated in FIG. 45. In this case, the through holes 181A have different sizes and have the same trapezoidal shape. Pattern 3 indicates an aspect of the plate-like member 180A illustrated in FIG. 46. In this case, the through holes 181A have the same size and have the same trapezoidal shape.

Pattern 4 indicates an aspect of the plate-like member 185 illustrated in FIG. 50. In this case, the through holes 186 have different sizes and have the same trapezoidal shape. Pattern 5 indicates an aspect of the plate-like member 187 illustrated in FIG. 51. In this case, the through holes 188 have different sizes and have the same rectangular shape.

The irradiation openings may be arranged at an interval of two or more radiation tubes 27. However, in this case, since one irradiation opening is shared by two or more radiation tubes 27, the number of times that, for example, the plate-like member is moved is two or more.

For example, in the first embodiment, the rack and pinion is described as an example of the displacement mechanism. However, the displacement mechanism is not limited thereto. Other known displacement mechanisms may be used.

Instead of the simple imaging in which the CC imaging illustrated in FIG. 5 and the MLO imaging illustrated in FIG. 6 are independently performed, a composite radiographic image equivalent to the radiographic image obtained by the simple imaging may be generated. The composite radiographic image is generated by performing a known composite image generation process, such as a minimum intensity projection method, for at least one of a plurality of projection images P obtained by the tomosynthesis imaging or a plurality of tomographic images T generated by the generation unit 83.

In each of the above-described embodiments, the mammography apparatus 10 has been exemplified. In the related art, performing tomosynthesis imaging in the mammography apparatus 10 has been found to be useful as a method for easily finding lesions such as microcalcifications of the breast M. Therefore, it is preferable to apply the technique of the present disclosure to the mammography apparatus 10.

Figure 53:
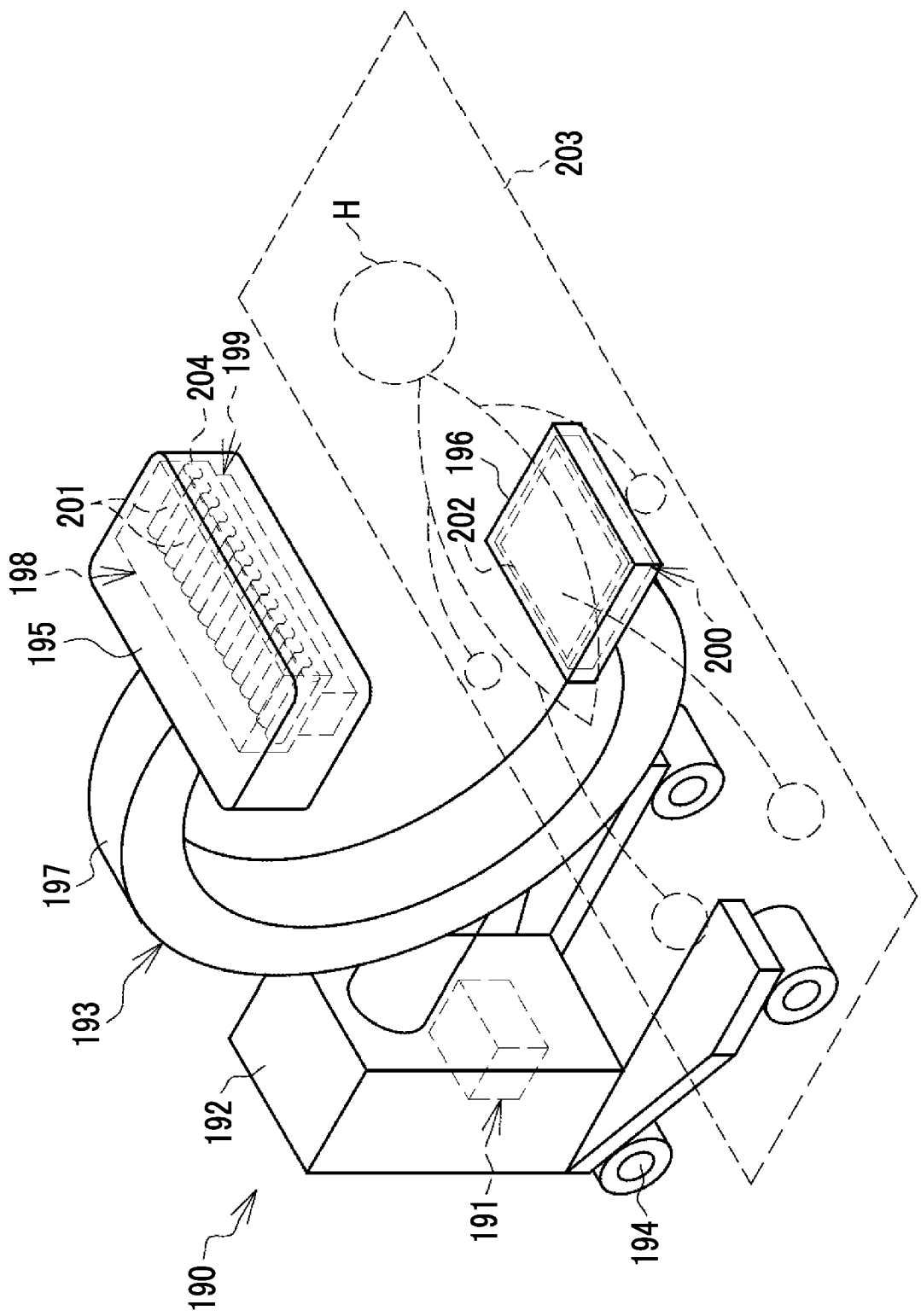
FIG. 53 is a diagram illustrating an imaging apparatus for surgery.

Of course, the technology of the present disclosure is not limited to the mammography apparatus 10 and may be applied to other imaging apparatuses. For example, the technology of the present disclosure may be applied to an imaging apparatus 190 illustrated in FIG. 53 which captures the image of the subject H during surgery.

The imaging apparatus 190 comprises an apparatus main body 192 having a control device 191 provided therein and an arm 193 having a substantially C-shape in a side view. A carriage 194 is attached to the apparatus main body 192 such that the apparatus main body 192 can be moved. The arm 193 includes a radiation source accommodation portion 195, a detector accommodation portion 196, and a main body portion 197. As in the mammography apparatus 10 illustrated in FIG. 1, the radiation source accommodation portion 195 accommodates a radiation source 198 and an irradiation field limiter 199. In addition, the detector accommodation portion 196 accommodates a radiation detector 200. The radiation source accommodation portion 195 and the detector accommodation portion 196 are held by the main body portion 197 at a posture where they face each other.

The radiation source 198 and the radiation detector 200 have the same basic configurations as the radiation source 25 and the radiation detector 26 illustrated in FIG. 1, respectively. However, the imaging apparatus 190 captures an image of an object, such as the entire chest of the subject H, which is larger than the breast M. Therefore, a radiation tube 201 forming the radiation source 198 has a larger diameter than each radiation tube 27 of the mammography apparatus 10. In addition, the radiation detector 200 has an imaging surface 202 whose area is larger than that of the imaging surface 45 of the radiation detector 26. The number of radiation tubes 201 arranged may increase in order to respond to the capture of the image of a large object.

The detector accommodation portion 196 is inserted below a bed 203 on which the subject H lies supine. The bed 203 is made of a material that transmits the radiation 37. The radiation source accommodation portion 195 is disposed above the subject H at a position that faces the detector accommodation portion 196 with the subject H interposed therebetween.

The irradiation field limiter 199 of the imaging apparatus 190 has a plurality of irradiation openings for the radiation 37 which are arranged at an interval of at least one radiation tube 201, similarly to the irradiation field limiter 29 of the mammography apparatus 10. The position of the irradiation openings is moved to at least two set positions including a first set position in a case in which the radiation 37 is emitted from first radiation tubes which are some of three or more radiation tubes 201 and a second set position in a case in which the radiation 37 is emitted from second radiation tubes different from the first radiation tubes among the three or more radiation tubes 27. The imaging apparatus 190 can also perform simple imaging using one radiation tube 201, in addition to the tomosynthesis imaging. In addition, instead of the simple imaging, the imaging apparatus may generate a composite radiographic image. Further, the imaging apparatus 190 may capture both still radiographic images and moving radiographic images. Furthermore, reference numeral 204 indicates a housing for the radiation source 198.

The technology of the present disclosure may be applied to a general radiography apparatus configured by combining a ceiling-suspended radiation source and an upright imaging table or a decubitus imaging table in which a radiation detector is set, in addition to the imaging apparatus 190 for surgery. Further, the technology of the present disclosure may be applied to, for example, a cart-type mobile radiography apparatus which is moved to each hospital room and is used to capture the image of the subject H.

In each of the above-described embodiments, the radiation tube 27 having one focus F is given as an example. However, the technology of the present disclosure is not limited thereto. A radiation tube having a plurality of focuses F may be used.

In the technology of the present disclosure, the above-described various embodiments and/or various modification examples may be combined with each other. In addition, the present disclosure is not limited to the above-described embodiments and various configurations can be used without departing from the scope and spirit of the present disclosure.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the scope and spirit of the technology of the present disclosure. In addition, in the above-described content and the above-illustrated content, the description of, for example, common technical knowledge that does not need to be particularly described to enable the implementation of the technology of the present disclosure are omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the publications, the patent applications, and the technical standards described in the specification are incorporated by reference herein to the same extent as each individual document, each patent application, and each technical standard are specifically and individually stated to be incorporated by reference.

What is claimed is:

1. A tomosynthesis imaging apparatus comprising:
   a radiation source in which three or more radiation tubes emitting radiation are arranged to perform tomosynthesis imaging which irradiates an object with the radiation at a plurality of different irradiation angles; and
   an irradiation field limiter in which a plurality of irradiation openings for the radiation that define an irradiation field of the radiation are arranged along an arrangement direction of the radiation tubes at an interval of at least one radiation tube and a position of the irradiation openings is moved to at least two set positions including a first set position in a case in which the radiation is emitted from first radiation tubes which are some of the three or more radiation tubes and a second set position in a case in which the radiation is emitted from second radiation tubes different from the first radiation tubes among the three or more radiation tubes, wherein
   the irradiation field limiter comprises a plate-like member in which a plurality of through holes, functioning as the irradiation opening, are formed,
   a plane on which the radiation tubes are arranged and a plane of the plate-like member are respectively inclined with respect to an imaging surface, and
   each of the through holes has a trapezoidal shape, when viewed from an irradiation direction of the radiation source, in which the base is widened toward one short side of the plate-like member.

2. The tomosynthesis imaging apparatus according to claim 1, wherein
   the plate-like member is moved along the arrangement direction of the radiation tubes to move the position of the irradiation openings to the at least two set positions.

3. The tomosynthesis imaging apparatus according to claim 2, wherein
   the plate-like member is moved in a direction in which an interval between the radiation tube and the through hole changes.

4. The tomosynthesis imaging apparatus according to claim 1, wherein
   a plurality of the radiation tubes are arranged at equal intervals in a linear shape or an arc shape.

5. The tomosynthesis imaging apparatus according to claim 1, further comprising
   a first positional relationship between the plane of the plate-like member and the imaging surface and a second positional relationship between the plane of the plate-like member and the plane on which the radiation tubes are arranged, wherein
   one of the first positional relationship and the second positional relationship is not parallel, and the other is parallel, and
   the plurality of through holes have different sizes.

6. A tomosynthesis imaging apparatus comprising:
   a radiation source in which three or more radiation tubes emitting radiation are arranged to perform tomosynthesis imaging which irradiates an object with the radiation at a plurality of different irradiation angles; and
   an irradiation field limiter in which a plurality of irradiation openings for the radiation that define an irradiation field of the radiation are arranged along an arrangement direction of the radiation tubes at an interval of at least one radiation tube and a position of the irradiation openings is moved to at least two set positions including a first set position in a case in which the radiation is emitted from first radiation tubes which are some of the three or more radiation tubes and a second set position in a case in which the radiation is emitted from second radiation tubes different from the first radiation tubes among the three or more radiation tubes, wherein
   the irradiation field limiter includes a plate-like member in which a through hole functioning as the irradiation opening is formed,
   the plate-like member is moved along the arrangement direction of the radiation tubes to move the position of the irradiation openings to the at least two set positions, and
   the plate-like member has a flat shape and a convex portion that protrudes from a flat plane of the plate-like member toward the radiation tube between the through holes adjacent to each other.

7. A tomosynthesis imaging apparatus comprising:
   a radiation source in which three or more radiation tubes emitting radiation are arranged to perform tomosynthesis imaging which irradiates an object with the radiation at a plurality of different irradiation angles; and
   an irradiation field limiter in which a plurality of irradiation openings for the radiation that define an irradiation field of the radiation are arranged along an arrangement direction of the radiation tubes at an interval of at least one radiation tube and a position of the irradiation openings is moved to at least two set positions including a first set position in a case in which the radiation is emitted from first radiation tubes which are some of the three or more radiation tubes and a second set position in a case in which the radiation is emitted from second radiation tubes different from the first radiation tubes among the three or more radiation tubes, wherein
   the irradiation field limiter includes a plate-like member in which a through hole functioning as the irradiation opening is formed,
   the plate-like member includes a plurality of parts of the plate-like member that are arranged in the arrangement direction of the radiation tubes, and each of the parts is rotated about a rotating shaft which is provided at one end side of each of the plurality parts and between the radiation tube and an imaging surface of a radiation detector that detects the radiation and outputs a radiographic image to move the irradiation opening to the at least two set positions, and the rotating shaft extends in a direction that is orthogonal to an arrangement direction of the radiation tubes and that is parallel to the imaging surface of the radiation detector.

8. A tomosynthesis imaging apparatus comprising:

a radiation source in which three or more radiation tubes emitting radiation are arranged to perform tomosynthesis imaging which irradiates an object with the radiation at a plurality of different irradiation angles; and an irradiation field limiter in which a plurality of irradiation openings for the radiation that define an irradiation field of the radiation are arranged along an arrangement direction of the radiation tubes at an interval of at least one radiation tube and a position of the irradiation openings is moved to at least two set positions including a first set position in a case in which the radiation is emitted from first radiation tubes which are some of the three or more radiation tubes and a second set position in a case in which the radiation is emitted from second radiation tubes different from the first radiation tubes among the three or more radiation tubes, wherein the irradiation field limiter has an adjustment member that adjusts widths of the plurality of irradiation openings at once, the adjustment member is moved in a direction intersecting the arrangement direction of the radiation tubes to adjust the widths of the plurality of irradiation openings at once, and the plurality of irradiation openings of the irradiation field limiter are arranged adjacently on a plane thereof that intersects an irradiation direction of the radiation.

9. The tomosynthesis imaging apparatus according to claim 8, wherein the irradiation field limiter has a configuration in which plate-like members, in which a through hole at least one side of which functions as an opening edge of the irradiation opening is formed, are stacked in a direction normal to an imaging surface of a radiation detector that detects the radiation and outputs a radiographic image, and each of a plurality of the plate-like members is moved along the arrangement direction of the radiation tubes to move the position of the irradiation openings to the at least two set positions.

10. The tomosynthesis imaging apparatus according to claim 9, wherein the irradiation field limiter has one actuator that moves two of the plate-like members, which are adjacent to each other in a stacking direction, along the arrangement direction of the radiation tubes at the same time.

11. The tomosynthesis imaging apparatus according to claim 8, wherein the irradiation field limiter includes a sheet-like member in which a through hole functioning as the irradiation opening is formed, and the sheet-like member is sent along the arrangement direction of the radiation tubes and is rolled to move the irradiation opening.

12. The tomosynthesis imaging apparatus according to claim 11, wherein a plurality of types of the through holes having different sizes are formed in the sheet-like member.

13. The tomosynthesis imaging apparatus according to claim 8, wherein the irradiation field limiter comprises a pair of plate-like members that have line-symmetric shapes with respect to the arrangement direction of the radiation tubes.

14. The tomosynthesis imaging apparatus according to claim 13, wherein each of the pair of plate-like members comprises a comb shape in which a plurality of rectangular plate-like protruding portions protrude, from long portions that are long in the arrangement direction of the radiation tubes, in a direction intersecting the arrangement direction of the radiation tubes at intervals, and the pair of plate-like members are disposed so as to deviate from each other in the direction intersecting the arrangement direction of the radiation tubes.

15. The tomosynthesis imaging apparatus according to claim 13, wherein the pair of plate-like members are moved obliquely upward or obliquely downward in the direction intersecting the arrangement direction of the radiation tubes.

16. A tomosynthesis imaging apparatus comprising:

a radiation source in which three or more radiation tubes emitting radiation are arranged to perform tomosynthesis imaging which irradiates an object with the radiation at a plurality of different irradiation angles; and an irradiation field limiter in which a plurality of irradiation openings for the radiation that define an irradiation field of the radiation are arranged along an arrangement direction of the radiation tubes at an interval of at least one radiation tube and a position of the irradiation openings is moved to at least two set positions including a first set position in a case in which the radiation is emitted from first radiation tubes which are some of the three or more radiation tubes and a second set position in a case in which the radiation is emitted from second radiation tubes different from the first radiation tubes among the three or more radiation tubes, wherein the irradiation field limiter comprises a plate-like member in which a plurality of through holes, functioning as the irradiation opening, are formed, a plane on which the radiation tubes are arranged and a plane of the plate-like member are respectively inclined with respect to an imaging surface, each of the plurality of through holes has a trapezoidal shape in which the base is widened toward one short side of the plate-like member, the plane on which the radiation tubes is arranged and the plane of the plate-like member are each inclined with respect to the imaging surface at different angles so that a ratio of a distance between the radiation tube and the plate-like member to a distance between the plate-like member and the imaging surface is the same, and the plurality of through holes have the same size.

* * * * *